United States Patent
Owens

(10) Patent No.: US 9,688,676 B2
(45) Date of Patent: Jun. 27, 2017

(54) TYROSINE KINASE INHIBITORS

(71) Applicant: PRINCIPIA BIOPHARMA INC., South San Francisco, CA (US)

(72) Inventor: Timothy D. Owens, Redwood City, CA (US)

(73) Assignee: PRINCIPIA BIOPHARMA INC., South San Francisco, CA (US)

( * ) Notice: Subject to any disclaimer, the term of this patent is extended or adjusted under 35 U.S.C. 154(b) by 0 days.

(21) Appl. No.: 15/410,716

(22) Filed: Jan. 19, 2017

(65) Prior Publication Data

US 2017/0129890 A1    May 11, 2017

Related U.S. Application Data

(63) Continuation of application No. PCT/US2016/035588, filed on Jun. 2, 2016.

(60) Provisional application No. 62/170,547, filed on Jun. 3, 2015, provisional application No. 62/271,689, filed on Dec. 28, 2015.

(51) Int. Cl.
*C07D 471/04* (2006.01)

(52) U.S. Cl.
CPC ................. *C07D 471/04* (2013.01)

(58) Field of Classification Search
None
See application file for complete search history.

(56) References Cited

FOREIGN PATENT DOCUMENTS

| | | |
|---|---|---|
| CN | 101610676 A | 12/2009 |
| CN | 104640861 A | 5/2015 |
| CN | 105753863 A | 7/2016 |
| EP | 2 578 585 A1 | 4/2013 |
| WO | WO 03/037890 A2 | 5/2003 |
| WO | WO 2006/086634 A2 | 8/2006 |
| WO | WO 2007/142755 A2 | 12/2007 |
| WO | WO 2008/039218 A2 | 4/2008 |
| WO | WO 2012/158764 A1 | 11/2012 |
| WO | WO 2013/116382 A1 | 8/2013 |
| WO | WO 2017/041536 A1 | 3/2017 |
| WO | WO 2017/066014 A1 | 4/2017 |

OTHER PUBLICATIONS

Arora, Amit. JPET 315:971-979, 2005.*
Auto-immune Diseases:Medlineplus (2014). Web: <https://www.nlm.nih.gov/medlineplus/autoimmunediseases.html>.*
MedicineNet.com. (2004). Web<http://www.medterms.com>.*
WebMD. Multiple Sclerosis (MS)-Prevention. (2015) Web: < http://www.webmd.com/multiple-sclerosis/tc/multiple-sclerosis-ms-prevention>.*
WebMD. 10 Ways to Prevent Psoriasis Flare-Ups. (2016) Web < http://www.webmd.com/skin-problems-and-treatments/psoriasis/prevent-flare-ups>.*
American Cancer Society. Can Non-Hodgkins Lymphoma Be Prevented? (2016) Web: <https://www.cancer.org/cancer/non-hodgkin-lymphoma/causes-risks-prevention/prevention.html>.*
Patani, George. Chem. Rev. 1996, 96, 3147-3176.*
Certified English translation of CN 105753863 A.
International Search Report from the European Patent Office, in corresponding Application No. PCT/US2016/035588, mailing date Aug. 16, 2016 (3 pages).
Written Opinion of the International Searching Authority from the European Patent Office in corresponding Application No. PCT/US2016/035588, mailing date Aug. 16, 2016 (5 pages).
Pennington et al., "The Necessary Nitrogen Atom: A Versatile High-Impact Design Element for Multiparameter Optimization," *J. Med. Chem.*, ePub Feb. 8, 2017, 28 pages, DOI: 10.1021/acs.jmedchem.6b01807.
English Translation of PCT International Search Report for International Application No. PCT/CN2016/084057, mailed Sep. 2, 2016 (4 pages).

* cited by examiner

*Primary Examiner* — Deepak Rao
*Assistant Examiner* — Laura Daniel
(74) *Attorney, Agent, or Firm* — Finnegan, Henderson, Farabow, Garrett & Dunner, LLP

(57) ABSTRACT

The present disclosure provides compounds that are tyrosine kinase inhibitors, in particular Bruton tyrosine kinase ("BTK") inhibitors, and are therefore useful for the treatment of diseases treatable by inhibition of BTK such as cancer, autoimmune, inflammatory, and thromboembolic diseases. Also provided are pharmaceutical compositions containing such compounds and processes for preparing such compounds.

3 Claims, No Drawings

TYROSINE KINASE INHIBITORS

The present application is a continuation of PCT International Patent Application No. PCT/US2016/035588 filed Jun. 2, 2016, which claims the benefit of U.S. Provisional Application Ser. No. 62/170,547 filed Jun. 3, 2015 and U.S. Provisional Application Ser. No. 62/271,689 filed Dec. 28, 2015, each of which is incorporated herein by reference in its entirety.

The present disclosure provides compounds that are tyrosine kinase inhibitors, in particular Bruton tyrosine kinase ("BTK") inhibitors, and are therefore useful for the treatment of diseases such as cancer, autoimmune, inflammatory, and thromboembolic diseases. Also provided are pharmaceutical compositions containing such compounds and processes for preparing such compounds.

BTK, a member of the Tec family non-receptor tyrosine kinases, is essential for B cell signaling downstream from the B-cell receptor. It is expressed in B cells and other hematopoietic cells such as monocytes, macrophages and mast cells. It functions in various aspects of B cell function that maintain the B cell repertoire (see Gauld S. B. et al., B cell antigen receptor signaling: roles in cell development and disease. Science, 296:1641-2. 2002.) B cells pay a role in rheumatoid arthritis (see Perosa F., et al., CD20-depleting therapy in autoimmune diseases: from basic research to the clinic. *J Intern Med.* 267:260-77. 2010 and Dörner T, et al. Targeting B cells in immune-mediated inflammatory disease: a comprehensive review of mechanisms of action and identification of biomarkers. *Pharmacol Ther.* 125:464-75. 2010 and Honigberg, L., et. al., The selective BTK inhibitor PCI-32765 blocks B cell and mast cell activation and prevents mouse collagen indiced arthritis. *Clin. Immunol.* 127 S1:S111. 2008) and in other autoimmune diseases such as systemic lupus erythematosus and cancers (see Shlomchik M. J., et. al., The role of B cells in lpr/lpr-induced autoimmunity. *J. Exp Med.* 180:1295-1306. 1994; Honigberg L. A., The Bruton tyrosine kinase inhibitor PCI-32765 blocks B-cell activation and is efficacious in models of autoimmune disease and B-cell malignancy. *Proc. Natl. Acad Sci.* 107:13075-80. 2010; and Mina-Osorio P, et al., Suppression of glomerulonephritis in lupus-prone NZB× NZW mice by RN486, a selective inhibitor of Bruton's tyrosine kinase. *Arthritis Rheum.* 65: 2380-91. 2013).

There is also potential for BTK inhibitors for treating allergic diseases (see Honigberg, L., et. al., The selective BTK inhibitor PCI-32765 blocks B cell and mast cell activation and prevents mouse collagen indiced arthritis. *Clin. Immunol.* 127 S1:S111. 2008). It was noted that the irreversible inhibitor suppresses passive cutaneous anaphylaxis (PCA) induced by IgE antigen complex in mice. These findings are in agreement with those noted with BTK-mutant mast cells and knockout mice and suggest that BTK inhibitors may be useful for the treatment of asthma, an IgE-dependent allergic disease of the airway.

Accordingly, compounds that inhibit BTK would be useful in treatment for diseases such as autoimmune diseases, inflammatory diseases, and cancer.

In a first aspect, this disclosure is directed to a compound of Formula (I):

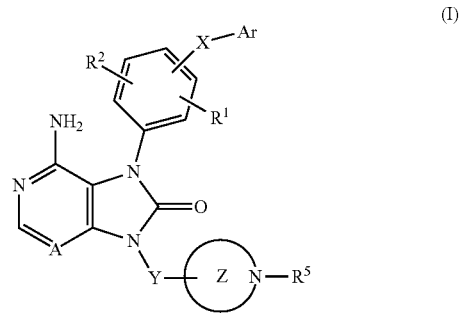

wherein:
$R^1$ and $R^2$ are independently hydrogen, alkyl, alkoxy, halolakyl, or halo;
X is —O—, —CONR—, —NRCO—, or —NR—CO—NR' where R and R' are independently hydrogen or alkyl;
Ar is heteroaryl or phenyl where heteroaryl and phenyl are optionally substituted with one, two, or three substituents independently selected from alkyl, halo, haloalkyl, alkoxy, and hydroxy;
A is —N— or —CR$^3$— wherein $R^3$ is hydrogen, alkyl, cyclopropyl, halo, haloalkyl, haloalkoxy, alkoxy, or cyano;
Y is bond or alkylene;
ring Z is heterocycloamino optionally substituted with one or two substituents independently selected from alkyl, hydroxy, alkoxy, and fluoro;
$R^5$ is a group of formula (i), (ii), (iii) or (iv):

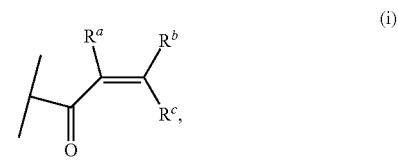

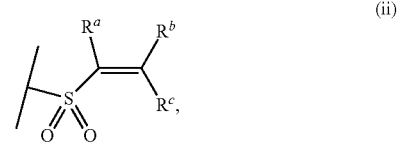

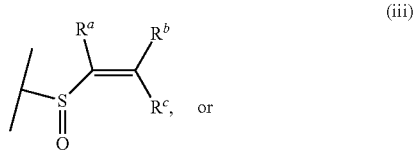

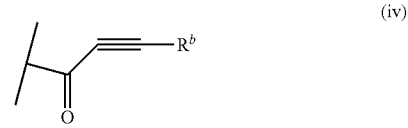

wherein:
$R^a$ is hydrogen, fluoro, or cyano; provided that when $R^a$ is cyano then $R^b$ is hydrogen and $R^c$ is not hydrogen;
$R^b$ is hydrogen or alkyl; and
$R^c$ is hydrogen, hydroxyalkyl, alkoxyalkyl, alkyl (optionally substituted with one or two substituents independently selected from hydroxy, hydoxyalkyl, heteroaryl (optionally substituted with one or two substituents independently selected from alkyl and heterocyclyl wherein heterocyclyl is optionally substituted with one or two substituents independently selected from halo and alkyl), and —CONR⁹R¹⁰ (where R⁹ and R¹⁰ are independently hydrogen or alkyl, or R⁹ and R¹⁰ together with the nitrogen atom to which they are attached form a heterocyclyl optionally substituted with one or two substituents selected from alkyl and heterocyclyl)), cycloalkyl (optionally substituted with one or two substituents independently selected from halo, alkyl, alkoxyalkyl and aryl; or wherein two adjacent substituents of the cycloalkyl together with the carbon atoms to which they are attached form a heterocyclyl group), heterocyclylalkyl, heterocyclyl (wherein heterocyclyl and heterocyclyl in heterocyclylalkyl are optionally substituted with one, two, or three substituents where two of the optional substituents are independently selected from alkyl, alkoxy, hydroxy, halo, amino, and oxo, and one of the optional substituent is alkyl, hydroxyalkyl, alkoxy, alkoxyalkyl, acyl, haloalkyl, alkylsulfonyl, alkoxycarbonyl, or heterocyclyl wherein the heterocyclyl is substituted with one or two substituents independently selected from hydrogen, alkyl, halo, hydroxy, and alkoxy), or -(alkylene)-NR⁶R⁷ (where R⁶ and R⁷ are independently hydrogen, alkyl, haloalkyl, hydroxyalkyl, alkoxyalkyl, cycloalkyl, or heterocyclyl wherein the heterocyclyl is optionally substituted with one or two substituents independently selected from alkyl, halo, hydroxy, hydroxyalkyl, alkoxyalkyl, acyl, and alkoxycarbonyl; or R⁶ and R⁷ together with the nitrogen atom to which they are attached form

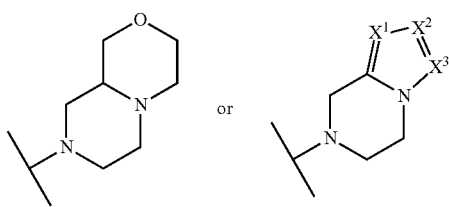

where one or two of X¹, X² and X³ are nitrogen and the rest are carbon and the ring is optionally substituted with one or two substituents independently selected from alkyl, haloalkyl, and halo); and/or a pharmaceutically acceptable salt thereof provided that:
when A is —N—, then Rᵃ is cyano and Rᶜ is heterocycloaminoalkyl wherein the heterocycloamino in heterocycloaminoalkyl is optionally substituted with one or two substituents independently selected from alkyl, alkoxy, hydroxy, halo, amino, and oxo, and the nitrogen atom of heterocycloamino is substituted with heterocyclyl wherein the heterocyclyl is substituted with one or two substituents independently selected from hydrogen, alkyl, halo, hydroxy, and alkoxy.

In one embodiment, when R⁵ in the compounds of Formula (I) and/or a pharmaceutically acceptable salt thereof (and any embodiments thereof disclosed herein) is a group of formula (i), (ii), or (iii) wherein Rᵃ is cyano, the compounds of the disclosure are reversible covalent inhibitors of BTK, i.e., they can form a reversible covalent bond with a thiol group of a cysteine residue, in particular with Cys481 of BTK.

In another embodiment, when R⁵ in the compounds of Formula (I) and/or a pharmaceutically acceptable salt thereof (and any embodiments thereof disclosed herein) is a group of formula (i), (ii), or (iii) where Rᵃ is hydrogen or fluoro, or R⁵ is a group of formula (iv), the compounds of the disclosure are irreversible covalent inhibitors of BTK, i.e., they can form an irreversible covalent bond with a thiol group of a cysteine residue, in particular with Cys481 of BTK.

In a second aspect, this disclosure is directed to a pharmaceutical composition comprising a compound of Formula (I) (or any of the embodiments thereof described herein), and/or a pharmaceutically acceptable salt thereof; and a pharmaceutically acceptable excipient.

(a) In embodiment (a) of the second aspect, the formulation is a solid oral formulation comprising:
(i) a compound of Formula (I) and/or a pharmaceutically acceptable salt thereof (or any embodiment thereof disclosed herein): and
(ii) means for release of said compound and/or a pharmaceutically acceptable salt thereof in the intestine.

(b) In embodiment (b) of the second aspect, the formulation is a solid oral formulation comprising means for release of a therapeutically effective amount of a compound of Formula (I) and/or a pharmaceutically acceptable salt thereof (or any embodiment thereof disclosed herein) from said oral formulation in the intestine.

Within embodiment (a) or (b), in one embodiment the compound of Formula (I) and/or a pharmaceutically acceptable salt thereof (or any embodiment thereof disclosed herein) is released in the small intestine.

In yet another embodiment of embodiment (a) or (b) and embodiments contained therein, wherein (i) the compound of Formula (I) and/or a pharmaceutically acceptable salt thereof (or embodiments thereof disclosed herein); and/or (ii) the dosage form comprising a compound of Formula (I) (or embodiments thereof disclosed herein); and/or a pharmaceutically acceptable salt thereof; is coated with at least one coating wherein the said coating is independently chosen from (when more than one coating is present) enteric coating and a non-enteric time-delayed release coating, preferably the coating is one or more enteric coating.

In one embodiment, when the compound of Formula (I) and/or a pharmaceutically acceptable salt thereof (or embodiments thereof disclosed herein) and/or the dosage form comprising the compound of Formula (I) and/or a pharmaceutically acceptable salt thereof (or embodiments thereof disclosed herein) is coated with an enteric coating, the enteric coating is a polymer. In another embodiment, when the compound of Formula (I) and/or a pharmaceutically acceptable salt thereof and/or the dosage form comprising the compound of Formula (I) and/or a pharmaceutically acceptable salt thereof is coated with an enteric coating, the enteric coating is an anionic polymer selected from polymethacrylates (e.g., methacrylic acid ethacrylate poly, methacrylic acid methyl methacrylate poly); cellulose-based polymers (e.g., cellulose acetate phthalate CAP, cellulose acetate trimellitate CAT, cellulose acetate succinate CAS, hydroxypropylmethyl-cellulose phthalate HPMCP, hydroxypropylmethylcellulose acetate succinate HPM-CAS), and polyvinyl derivatives such as polyvinyl acetate phthalate PVAP. In yet another embodiment, the enteric coating erodes in the gastrointestinal track having a pH from about 4.5 to about 7 or from about 5 or 5.5 to about 7 to release the compound of Formula (I) and/or a pharmaceutically acceptable salt thereof (or embodiments thereof disclosed herein).

When a non-enteric coating is employed, the non-enteric time-delayed release dosage forms can be administered in fasted state and the time-delayed release coating can be designed to erode, burst, or become highly permeable in about 0.3 to about 3 hours or in about 0.5 to about 2 hours after administration to release the compound of Formula (I) (or embodiments thereof disclosed herein) and/or a pharmaceutically acceptable salt thereof.

In a third aspect, this disclosure is directed to a method of treating a disease treatable by inhibition of BTK in a mammal in need thereof which method comprises administering to the mammal in need thereof, a pharmaceutical composition comprising a therapeutically effective amount of a compound of Formula (I) (or any of the embodiments thereof described herein) and/or a pharmaceutically acceptable salt thereof, and a pharmaceutically acceptable excipient. In one embodiment the disease is cancer, autoimmune, inflammatory, or thromboembolic diseases. In one embodiment, the disease is acute necrotizing hemorrhagic leukoencephalitis, acute disseminated encephalomyelitis, Addison's disease, agammaglobulinemia, alopecia areata, alopecia universalis, amyloidosis, ankylosing spondylitis, anti-GBM/Anti-TBM nephritis, antiphospholipid syndrome (APS), antiphospholipid antibody syndrome, aplastic anemia, arthritis, autoimmune angioedema, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticaria, autoimmune hemolytic anemia, axonal & neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, coeliac disease, Cogans syndrome, cold agglutinin disease, congenital heart block, coxsackie myocarditis, CREST disease, Crohn's disease, demyelinating neuropathies, dermatitis herpetiformis, dermatomyositis, Devic's disease (neuromyelitis optica), diabetes, discoid lupus, Dressler's syndrome, dry eye, dysautonomia, endometriosis, eosinophilic esophagitis, eosinophilic fasciitis, erythema nodosum, essential mixed cryoglobulinemia, Evans syndrome, experimental allergic encephalomyelitis, fibromyalgia, fibrosing alveolitis, giant cell arteritis (temporal arteritis), giant cell myocarditis, glomerulonephritis, Goodpasture's syndrome, granulomatosis with polyangiitis (GPA) (formerly called Wegener's Granulomatosis), Graves' disease, Guillain-Barre syndrome, Hashimoto's thyroiditis, hemolytic anemia, Henoch-Schonlein purpura, herpes gestationis, hypogammaglobulinemia, idiopathic pulmonary fibrosis, idiopathic thrombocytopenic purpura (ITP), IgA nephropathy, IgG4-related sclerosing disease, immunoregulatory lipoproteins, inclusion body myositis, inflammatory bowel disease, interstitial cystitis, juvenile arthritis, juvenile diabetes (Type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (SLE), lupus including lupus nephritis, lyme disease, chronic, Meniere's disease, microscopic polyangiitis, mixed connective tissue disease (MCTD), mooren's ulcer, Mucha-Habermann disease, mucous membrane pemphigoid, multiple sclerosis, myasthenia gravis, myositis, narcolepsy, neuromyotonia, neutropenia, ocular cicatricial pemphigoid, opsoclonus-myoclonus syndrome, optic neuritis, Ord's thyroiditis, osteoarthritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, pars planitis (peripheral uveitis), Parsonnage-Turner syndrome, peripheral neuropathy, perivenous encephalomyelitis, pernicious anemia, pemphigus such as pemphigus vulgaris, pemphigus foliaceus, POEMS syndrome, polyarteritis nodosa, polymyalgia rheumatica, polymyositis, postmyocardial infarction syndrome, postpericardiotomy syndrome, primary biliary cirrhosis, primary sclerosing cholangitis, primary biliary cirrhosis, progesterone dermatitis, psoriasis, psoriatic arthritis, psoriaticarthritis, pure red cell aplasia, pyoderma gangrenosum, raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, Still's disease, subacute bacterial endocarditis (SBE), Susac's syndrome, sympathetic ophthalmia, Takayasu's arteritis, temporal arteritis/Giant cell arteritis, thrombocytopenic purpura (TTP), Tolosa-Hunt syndrome, transverse myelitis, Type I, II, & III autoimmune polyglandular syndromes, ulcerative colitis, undifferentiated connective tissue disease (UCTD), uveitis, vasculitis, vesiculobullous dermatosis, vitiligo, vulvodynia, or lupus.

In one embodiment of the third aspect, the mammal is suffering from an autoimmune disease, e.g., inflammatory bowel disease, arthritis, lupus including Lupus Nephritis, rheumatoid arthritis, psoriatic arthritis, osteoarthritis, Still's disease, juvenile arthritis, diabetes, myasthenia gravis, granulomatosis with polyangiitis, Hashimoto's thyroiditis, Ord's thyroiditis, Graves' disease, Sjogren's syndrome, dry eye (including Sjogren's dry eye and non-Sjogren's dry eye), multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, pemphigus such as pemphigus vulgaris and/or foliaceus, bullous pemphigoid, age-related macular degeneration (wet and dry), diabetic macular edema, corneal transplantation, abdominal aortic aneurysm, mucous membrane pemphigoid, or vulvodynia.

In another embodiment, the autoimmune disease is lupus, pemphigus vulgaris, myasthenia gravis, Sjogren's syndrome, dry eye, multiple sclerosis, Wegener's granulomatosis, autoimmune hemolytic anemia, idiopathic thrombocytopenic purpura, Granulomatosis with Polyangiitis, or rheumatoid arthritis.

In another embodiment of the third aspect, the mammal is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis. In another embodiment, the disease is atopic dermatitis.

In yet another embodiment of the third aspect, the mammal is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis. In another embodiment of this aspect, the mammal is suffering from inflammatory skin disease which includes, by way of example, dermatitis, contact dermatitis, eczema, urticaria, rosacea, and scarring psoriatic lesions in the skin, joints, or other tissues or organs. In another embodiment, the inflammatory disease is asthma or dermatitis.

In yet another embodiment of the third aspect, the mammal is suffering from inflammatory and/or autoimmune disease, including acute inflammatory and/or autoimmune disease, where corticosteroid therapy is used as the first or second line therapy or first or second line maintenance therapy. In one embodiment, the compound of Formula (I) (or any embodiments thereof disclosed herein) is used for the treatment of:

Endocrine Disorders: Primary or secondary adrenocortical insufficiency (hydrocortisone or cortisone is the first choice: synthetic analogs may be used in conjunction with mineralocorticoids where applicable; in infancy mineralocorticoid supplementation is of particular importance); congenital adrenal hyperplasia; nonsuppurative thyroiditis; hypercalcemia associated with cancer.

Rheumatic Disorders: As adjunctive therapy for short-term administration (to tide the patient over an acute episode or exacerbation) in: psoriatic arthritis, rheumatoid arthritis, including juvenile rheumatoid arthritis (selected cases may require low-dose maintenance therapy), ankylosing spondylitis, acute and subacute bursitis, acute nonspecific tenosynovitis, gout, acute gouty arthritis, post-traumatic osteoarthritis, synovitis of osteoarthritis, epicondylitis.

Collagen Diseases: During an exacerbation or as maintenance therapy in selected cases of: systemic lupus erythematosus, systemic dermatomyositis (polymyositis), acute rheumatic carditis.

Dermatologic Diseases: Pemphigus; bullous dermatitis herpetiformis; severe erythema multiforme (Stevens-Johnson syndrome); exfoliative dermatitis; mycosis fungoides; severe psoriasis; severe seborrheic dermatitis.

Allergic States: Control of severe or incapacitating allergic conditions intractable to adequate trials of conventional treatment: seasonal or perennial allergic rhinitis; bronchial asthma; contact dermatitis; atopic dermatitis; serum sickness; drug hypersensitivity reactions.

Ophthalmic Diseases: Severe acute and chronic allergic and inflammatory processes involving the eye and its adnexa such as: allergic corneal marginal ulcers, herpes zoster ophthalmicus, anterior segment inflammation, diffuse posterior uveitis and choroiditis, sympathetic ophthalmia, allergic conjunctivitis, keratitis, chorioretinitis, optic neuritis, iritis and iridocyclitis.

Respiratory Diseases: Symptomatic sarcoidosis; Loeffler's syndrome not manageable by other means; berylliosis; aspiration pneumonitis, fulminating or disseminated pulmonary tuberculosis when used concurrently with appropriate antituberculous chemotherapy Hematologic Disorders: Idiopathic thrombocytopenic purpura in adults; secondary thrombocytopenia in adults; acquired (autoimmune) hemolytic anemia; erythroblastopenia (RBC anemia); congenital (erythroid) hypoplastic anemia.

Neoplastic Diseases: For palliative management of: leukemias and lymphomas in adults, acute leukemia of childhood.

Edematous States: To induce a diuresis or remission of proteinuria in the nephrotic syndrome, without uremia, of the idiopathic type or that due to lupus erythematosus.

Gastrointestinal Diseases: To tide the patient over a critical period of the disease in: ulcerative colitis, regional enteritis.

Miscellaneous: Tuberculous meningitis with subarachnoid block or impending block when used concurrently with appropriate antituberculous chemotherapy; trichinosis with neurologic or myocardial involvement.

The compound of Formula (I) and/or a pharmaceutically acceptable salt thereof can be used for the treatment of above listed diseases optionally in combination with a corticosteroid, noncorticosteroidal, immunosupressive, and/or antiinflammatory agents. In one embodiment, the immunosuppressive agent is selected from interferon alpha, interferon gamma, cyclophosphamide, tacrolimus, mycophenolate mofetil, methotrexate, dapsone, sulfasalazine, azathioprine, an anti-CD20 agent (such as rituximab, ofatumumab, obinutuzumab, or veltuzumab, or a biosimilar version thereof), anti-TNFalpha agent (such as entanercept, infliximab, golilumab, adalimumab, or certolizumab pegol or a biosimilar version thereof), anti-IL6 agent toward ligand or its receptors (such as tocilizumab, sarilumab, olokizumab, elsililumab, or siltuximab), anti-IL17 agent to ligand or its receptors (such as secukinumab, ustekinumab, brodalumab, or ixekizumab), anti-IL1 agent to ligand or its receptors (such as with rilonacept, canakinumab, or anakinra), anti-IL2 agent to ligand or its receptors (such as basiliximab or daclizumab), anti-CD2 agent such as alefacept, anti-CD3 agent such as muromonab-cd3, anti-CD80/86 agent such as abatacept or belatacept, anti-sphingosine-1-phosphate receptor agent such as fingolimod, anti-C5 agent such as eculizumab, anti-integrin alpha4 agent such as natalizumab, anti-$\alpha_4\beta_7$ agent such as vedolizumab, anti-mTOR agent such as sirolimus or everolimus, anti-calcineurin agent such as tacrolimus, and anti-BAFF/BlyS agent (such as belimumab, VAY736, or blisibimod), leflunomide and teriflunomide. Preferably, the immunosuppressive agent is rituximab, ofatumumab, obinutuzumab, or veltuzumab, or a biosimilar version thereof.

In yet another embodiment of tht third aspect, the mammal is suffering from a cancer. In one embodiment, the cancer is a B-cell proliferative disorder, e.g., diffuse large B cell lymphoma, follicular lymphoma, chronic lymphocytic lymphoma (CLL), chronic lymphocytic leukemia, chromic myleogenous leukemia, B-cell acute lymphoblastic leukemia (B-ALL), Philadelphia chromosome positive B-ALL, B-cell prolymphocytic leukemia, small lymphocytic lymphoma (SLL), multiple myeloma, B-cell non-Hodgkin lymphoma, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis.

In yet another embodiment of the third aspect, the mammal is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a fourth aspect, the disclosure is directed a compound of Formula (I) (and any embodiments thereof described herein) and/or a pharmaceutically acceptable salt thereof for use as a medicament. In one embodiment, the use of the compound of Formula (I) and/or a pharmaceutically acceptable salt thereof is for treating a disease mediated by BTK, for example, the disease is an inflammatory disease, autoimmune disease, cancer, or thromboembolic diseases described in the third aspect and embodiments therein.

In a fifth aspect is the use of a compound of Formula (I) (or any of the embodiments thereof described herein) and/or a pharmaceutically acceptable salt thereof, in the manufacture of a medicament for treating a disease in a mammal in which BTK contributes to the pathology and/or symptoms of the disease. In one embodiment of this aspect, the disease is cancer, autoimmune, inflammatory, or thromboembolic disease described in the third aspect and embodiments therein.

In any of the aforementioned aspects involving the treatment of cancer, are further embodiments comprising administering the compound of Formula (I) (or any of the embodiments thereof described herein) and/or a pharmaceutically acceptable salt thereof, in combination with an anticancer agent. When combination therapy is used, the agents can be administered simultaneously (such as a fixed combination drug product) or sequentially.

In a sixth aspect, this disclosure is directed to an intermediate of Formula (II):

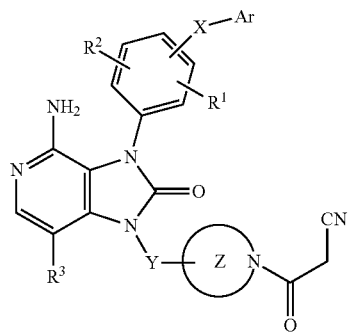

(II)

wherein:
$R^1$, $R^2$, $R^3$, X, Ar, Y, and ring Z are as defined in the first aspect above;
or a salt thereof.

In a seventh aspect, provided is a process of preparing:
(1). a compound of Formula (I) where $R^a$ is cyano, A is —$CR^3$— and other groups are as defined above; or
a pharmaceutically acceptable salt thereof;
comprising:
(a) reacting a compound of Formula (II):

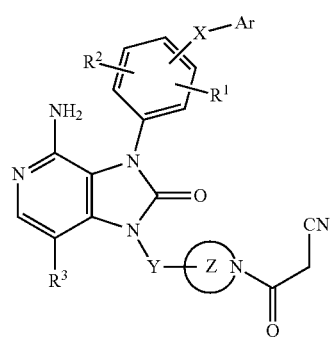

(II)

wherein:
$R^1$, $R^2$, $R^3$, X, Ar, Y, and ring Z are as defined in the first aspect above;
with an aldehyde of formula $R^cCHO$ where $R^c$ is as defined in the first aspect above; or
(b) reacting a compound of formula (III):

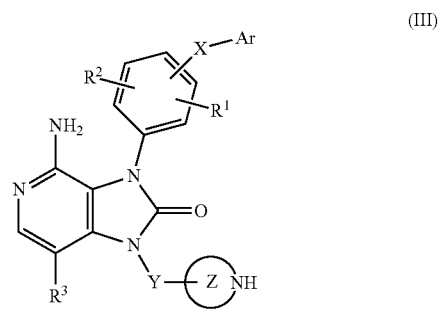

(III)

wherein:
$R^1$, $R^2$, $R^3$, X, Ar, Y, and Z are as defined in the first aspect above;
with a compound of formula $R^cCH=C(CN)COL$ where L is a leaving group under acylation reaction conditions where $R^c$ is as defined in the first aspect above; or
(2). a compound of Formula (I) where $R^a$ is hydrogen, A is —$CR^3$— and other groups are as defined in the first aspect above: or a pharmaceutical salt thereof; comprising reacting a compound of formula (III):

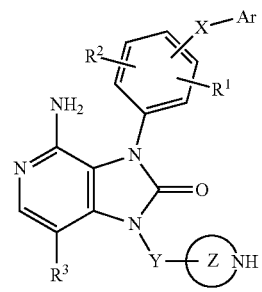

(III)

wherein
$R^1$, $R^2$, $R^3$, X, Ar, Y, and ring Z are as defined in the first aspect above;
with a compound of formula $R^cR^bC=CHCOL$ where L is a leaving group under acylation reaction conditions where $R^b$ and $R^c$ are as defined in the first aspect above;
(c) optionally making an acid addition salt of a compound obtained from Step (1) or (2) above;
(d) optionally making a free base of a compound obtained from Step (1) or (2) above.

Definitions:

Unless otherwise stated, the following terms used in the specification and claims are defined for the purposes of this disclosure and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylsulfonyl" means a —SO$_2$R radical where R is alkyl as defined above, e.g., methylsulfonyl, ethylsulfonyl, and the like.

"Amino" means a —NH$_2$.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with an alkoxy group, (in one embodiment one or two alkoxy groups), as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Acyl" means a —COR radical where R is alkyl, haloalkyl, or cycloalkyl, e.g., acetyl, propionyl, cyclopropylcarbonyl, and the like. When R is alkyl, the radical is also referred to herein as alkylcarbonyl.

"Cycloalkyl" means a cyclic saturated monovalent hydrocarbon radical of three to ten carbon atoms wherein one or two carbon atoms may be replaced by an oxo group, e.g., cyclopropyl, cyclobutyl, cyclopentyl, or cyclohexyl, and the like.

"Carboxy" means —COOH.

"Halo" means fluoro, chloro, bromo, or iodo; in one embodiment fluoro or chloro.

"Haloalkyl" means alkyl radical as defined above, which is substituted with one or one to five halogen atoms (in one embodiment fluorine or chlorine) including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can referred to in this disclosure as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it can referred to in this disclosure as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl. Further examples include, but are not limited to, 2-hydroxyethyl, 2,3-dihydroxypropyl, and 1-(hydroxymethyl)-2-hydroxyethyl.

"Heterocyclyl" means a saturated or unsaturated monovalent monocyclic or bi-cyclic group (fused bi-cyclic or bridged bi-cyclic) of 4 to 10 ring atoms in which one or two ring atoms are heteroatom selected from N, O, and S(O)$_n$, where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, oxetanyl, pyrrolidino, piperidino, homopiperidino, 2-oxopyrrolidinyl, 2-oxopiperidinyl, morpholino, piperazino, tetrahydropyranyl, thiomorpholino, hexahydropyrrolo[1,2-a]pyrazin-6(2H)-one-yl, tetrahydro-1H-oxazolo[3,4-a]pyrazin-3(5H)-one-yl, 5,6,7,8-tetrahydro-[1,2,4]triazolo[4,3-a]pyrazine-yl, 3-oxa-8-azabicyclo[3.2.1]octane-yl, and the like. When the heterocyclyl ring is unsaturated it can contain one or two ring double bonds provided that the ring is not aromatic.

"Heterocyclylalkyl" means a -(alkylene)-R radical where R is heterocyclyl ring as defined above e.g., tetraydrofuranylmethyl, piperazinylmethyl, morpholinylethyl, and the like.

"Heterocycloamino" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C provided that at least one of the ring atoms is N. Additionally, one or two ring carbon atoms in the heterocycloamino ring can optionally be replaced by a —CO— group. When the heterocycloamino ring is unsaturated it can contain one or two ring double bonds provided that the ring is not aromatic.

"Heterocycloamninoalkyl" means a -(alkylene)-R radical where R is heterocycloamino as described above.

"Heteroaryl" means a monovalent monocyclic or bicyclic aromatic radical of 5 to 10 ring atoms where one or more, (in one embodiment one, two, or three), ring atoms are heteroatom selected from N, O, and S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

"Mammal" as used herein means domesticated animals (such as dogs, cats, and horses), and humans. In one embodiment, mammal is a human.

The present disclosure also includes the prodrugs of compounds of Formula (I) (or any of the embodiments thereof described herein) and/or a pharmaceutically acceptable salt thereof. The term prodrug is intended to represent covalently bonded carriers, which are capable of releasing the active ingredient of Formula (I) (or any of the embodiments thereof described herein) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vive or by routine manipulation. Prodrugs of compounds of Formula (I) (or any of the embodiments thereof described herein) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) (or any of the embodiments thereof described herein) and/or a pharmaceutically acceptable salt thereof are also within the scope of this disclosure.

The present disclosure also includes polymorphic forms (amorphous as well as crystalline) and deuterated forms of compounds of Formula (I) (or any of the embodiments thereof described herein) and/or a pharmaceutically acceptable salt thereof.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, racemic forms, as individual forms and mixtures thereof, are within the scope of this disclosure, unless the specific stereochemistry or isomeric form is specifically indicated.

Certain compounds of Formula (I) (or any of the embodiments thereof described herein) and/or a pharmaceutically acceptable salt thereof can exist as tautomers and/or geometric isomers. All possible tautomers and cis and trans isomers, as individual forms and mixtures thereof, are within the scope of this disclosure. Additionally, as used herein the term alkyl includes all the possible isomeric forms of said alkyl group albeit only a few examples are set forth. Furthermore, when the cyclic groups such as heteroaryl, heterocyclyl are substituted, they include all the positional isomers albeit only a few examples are set forth. Furthermore, all hydrate forms of a compound of Formula (I) (or any of the embodiments thereof described herein) and/or a pharmaceutically acceptable salt thereof are within the scope of this disclosure.

"Oxo" or "carbonyl" means =(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The phrase "where two of the optional substituents are independently selected from alkyl, alkoxy, hydroxy, halo, and oxo, and one of the optional substituent is alkyl, cycloalkyl, hydroxyalkyl, alkoxyalkyl, acyl, haloalkyl, alkylsulfonyl, alkoxycarbonyl, or heterocyclyl" in the definition of heterocyclyl for $R^c$ in Formula (I) (and similar phrases elsewhere in the claim and/or specification) means that when heterocyclyl is substituted with one substituent, the substituent can be any of the optional substituents listed. When heterocyclyl ring is substituted with two substituents, then either both substituents can be selected from alkyl, alkoxy, hydroxy, halo, and oxo or one of the two substituent is selected from alkyl, alkoxy, hydroxy, halo, and oxo and the other substituent is selected from alkyl, cycloalkyl, hydroxyalkyl, alkoxyalkyl, acyl, haloalkyl, alkylsulfonyl, alkoxycarbonyl, and heterocyclyl. And when heterocyclyl ring is substituted with three substituents, then two substituents are selected from alkyl, alkoxy, hydroxy, halo, and oxo and the third substituent is selected from alkyl, cycloalkyl, hydroxyalkyl, alkoxyalkyl, acyl, haloalkyl, alkylsulfonyl, alkoxycarbonyl, and heterocyclyl.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula (I) (or any of the embodiments thereof described herein), that, when administered to a mammal for treating a disease, is sufficient to effect such treatment for the disease. The "therapeutically effective amount" will vary depending on the compound, the disease and its severity and the age, weight, etc., of the mammal to be treated.

EMBODIMENTS

In embodiments 1-24 below and embodiments or subembodiments contained therein, the present disclosure includes:

1. A compound of Formula (I) as defined in the first embodiment of the first aspect above, including an E or Z isomer thereof, and/or a pharmaceutically acceptable salt thereof.

2. The compound of embodiment 1 and/or a pharmaceutically acceptable salt thereof wherein: $R^1$ and $R^2$ are independently hydrogen, alkyl, alkoxy, halolakyl, or halo;

X is —O—, —CONR—, —NRCO—, or —NR—CO—NR' where R and R' are independently hydrogen or alkyl;

Ar is heteroaryl or phenyl where heteroaryl and phenyl are optionally substituted with one, two, or three substituents independently selected from alkyl, halo, haloalkyl, alkoxy, and hydroxy;

A is —N— or —CR³— wherein R³ is hydrogen, alkyl, cyclopropyl, halo, haloalkyl, haloalkoxy, alkoxy, or cyano;

Y is bond or alkylene;

ring Z is heterocycloamino optionally substituted with one or two substituents independently selected from alkyl, hydroxy, alkoxy, and fluoro;

R⁵ is a group of formula (i), (ii), (iii) or (iv):

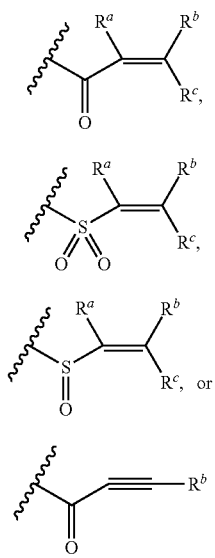

wherein:

R$^a$ is hydrogen, fluoro, or cyano; provided that when R$^a$ is cyano then R$^b$ is hydrogen and R$^c$ is not hydrogen;

R$^b$ is hydrogen or alkyl; and

R$^c$ is hydrogen, alkyl optionally substituted with one or two substituents independently selected from OH, heteroaryl (optionally substituted with one or two substituents independently selected from alkyl and heterocyclyl wherein heterocyclyl is optionally substituted with one or two substituents independently selected from halo and alkyl), and —CONR⁹R¹⁰ (where R⁹ and R¹⁰ are independently hydrogen or alkyl, or R⁹ and R¹⁰ together with the nitrogen atom to which they are attached form a heterocyclyl optionally substituted with one or two substituents selected from alkyl and heterocyclyl), cycloalkyl optionally substituted with one or two substituents independently selected from halo, alkyl and aryl, hydroxyalkyl, alkoxyalkyl, heterocyclylalkyl, heterocyclyl (wherein heterocyclyl and heterocyclyl in heterocyclylalkyl are optionally substituted with one, two, or three substituents where two of the optional substituents are independently selected from alkyl, alkoxy, hydroxy, halo, amino, and oxo, and one of the optional substituent is alkyl, hydroxyalkyl, alkoxy, alkoxyalkyl, acyl, haloalkyl, alkylsulfonyl, alkoxycarbonyl, or heterocyclyl wherein the heterocyclyl is substituted with one or two substitutents independently selected from hydrogen, alkyl, halo, hydroxy, and alkoxy), or -(alkylene)-NR⁶R⁷ (where R⁶ and R⁷ are independently hydrogen, alkyl, haloalkyl, hydroxyalkyl, alkoxyalkyl, cycloalkyl, or heterocyclyl wherein the heterocyclyl is optionally substituted with one or two substituents independently selected from alkyl, halo, hydroxy, hydroxyalkyl, alkoxyalkyl, acyl, and alkoxycarbonyl; or R⁶ and R⁷ together with the nitrogen atom to which they are attached form

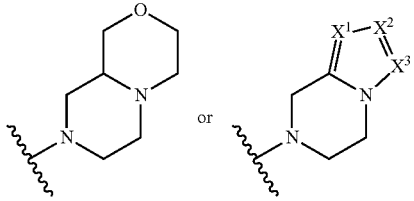

where one or two of X¹, X² and X³ are nitrogen and the rest are carbon and the ring is optionally substituted with one or two substituents independently selected from alkyl, haloalkyl, and halo);

and/or a pharmaceutically acceptable salt thereof provided that:

when A is —N—, then R$^a$ is cyano and R$^c$ is heterocycloaminolalkyl wherein the heterocycloamino in heterocycloaminoalkyl is optionally substituted with one or two substituents independently selected from alkyl, alkoxy, hydroxy, halo, amino, and oxo, and the nitrogen atom of heterocycloamino is substituted with heterocyclyl wherein the heterocyclyl is substituted with one or two substituents independently selected from hydrogen, alkyl, halo, hydroxy, and alkoxy.

3. The compound of embodiments 1 to 2 and/or a pharmaceutically acceptable salt thereof wherein A is —N—.

4. The compound of embodiments 1 to 2 and/or a pharmaceutically acceptable salt thereof wherein A is —CR³—. In one embodiment of embodiment 4, R³ is hydrogen, methyl, ethyl, isopropyl, fluoro, or chloro. In a second embodiment of embodiment 3, R³ is hydrogen.

5. The compound of any of embodiments 1 to 4 and embodiments contained therein and/or a pharmaceutically acceptable salt thereof wherein —X—Ar is attached to carbon at the 4-position of the phenyl ring, the carbon of the phenyl ring attached to N of the cyclic urea ring being position 1.

6. The compound of any of embodiments 1 to 5 and embodiments contained therein and/or a pharmaceutically acceptable salt thereof wherein X is —O—. Within embodiment 6, in a fourth embodiment, Ar is heteroaryl or phenyl where heteroaryl and phenyl are optionally substituted with one, two, or three substituents independently selected from alkyl, halo, haloalkyl, alkoxy, and hydroxy. Within embodiment 6, in a fifth embodiment, Ar is pyridinyl, pyrimidinyl, thienyl, or pyrazinyl, optionally substituted with one, two, or three substituents independently selected from alkyl, halo, haloalkyl, alkoxy, and hydroxy. Within embodiment 6, in a sixth embodiment, Ar is phenyl where phenyl is optionally substituted with one, two, or three substituents independently selected from alkyl, halo, haloalkyl, alkoxy, and hydroxy, preferably substituted with one or two fluoro.

7. The compound of any of embodiments 1 to 6 and embodiments contained therein and/or a pharmaceutically acceptable salt thereof wherein X is —CONR— or —NRCO—. Within embodiment 6, in a fourth embodiment, Ar is heteroaryl or phenyl where heteroaryl and phenyl are optionally substituted with one, two, or three substituents independently selected from alkyl, halo, haloalkyl, alkoxy, and hydroxy. Within embodiment 7, in a fifth embodiment, Ar is pyridinyl, pyrimidinyl, thienyl, or pyrazinyl, optionally substituted with one, two, or three substituents independently selected from alkyl, halo, haloalkyl, alkoxy, and hydroxy. Within embodiment 7, in a sixth embodiment, Ar is phenyl where phenyl is optionally substituted with one, two, or three substituents independently selected from alkyl, halo, haloalkyl, alkoxy, and hydroxy, preferably one or two fluoro.

8. The compound of any of embodiments 1 to 7 and embodiments contained therein and/or a pharmaceutically acceptable salt thereof wherein $R^1$ and $R^2$ are independently hydrogen or halo, preferably hydrogen or fluoro, more preferably $R^1$ and $R^2$ are hydrogen or $R^1$ is hydrogen and $R^2$ is fluoro.

9. The compound of any of embodiments 1 to 8 and embodiments contained therein and/or a pharmaceutically acceptable salt thereof wherein Y is alkylene and ring Z is pyrrolidinyl, and in one embodiment, pyrrolidin-2-yl or azetidin-3-yl. Within embodiment 9, in one embodiment, Y is methylene. Within embodiment 9, in a second embodiment, the pyrrolidinyl ring ring attached at C2 and the stereochemistry at carbon of the pyrrolidinyl ring attached to Y is (R) or (S). Within embodiment 9, is another embodiment, wherein $R^5$ is a group of formula (i) or (iv).

10. The compound of any of embodiments 1 to 9 and embodiments contained therein and/or a pharmaceutically acceptable salt thereof wherein Y is a bond and ring Z is pyrrolidinyl or piperidinyl and is attached to the cyclic urea nitrogen at the C-3 carbon, the nitrogen atom of pyrrolidinyl or piperidinyl being position C-1. In one embodiment, the stereochemistry at carbon of the pyrrolidinyl or piperidinyl attached to the cyclic urea nitrogen is (R).

11. The compound of any of embodiments 1 to 10 and embodiments contained therein and/or a pharmaceutically acceptable salt thereof wherein $R^a$ is hydrogen. Within embodiment 11, in one embodiment, $R^5$ is a group of formula (i). Within embodiment 11, in a second embodiment, $R^5$ is a group of formula (ii) or (iii). Within embodiment 11, in a third embodiment, $R^5$ is a group of formula (iv). Within the embodiments one to three in embodiment 11, in one subembodiment $R^b$ and $R^c$ are hydrogen. Within the embodiments one to three in embodiment 11, in another subembodiment $R^b$ is hydrogen and $R^c$ is alkyl or or -(alkylene)-$NR^6R^7$ (where $R^6$ and $R^7$ are independently hydrogen, alkyl, haloalkyl, hydroxyalkyl, alkoxyalkyl, cycloalkyl, or heterocyclyl wherein the heterocyclyl ring is optionally substituted with one or two substituents independently selected from alkyl, halo, hydroxy, hydroxyalkyl, alkoxyalkyl, acyl, and alkoxycarbonyl), preferably $R^6$ and $R^7$ are independently hydrogen or alkyl.

12. The compound of any of embodiments 1 to 11 and embodiments contained therein or a pharmaceutically acceptable salt thereof wherein $R^a$ is cyano. Within embodiment 12, in one embodiment, $R^5$ is a group of formula (i). Within embodiment 12, in a second embodiment, $R^5$ is a group of formula (ii) or (iii).

(a) Within the embodiments one and two in embodiment 12, in one subembodiment $R^c$ is cycloalkyl, which is optionally substituted with one or two substituents independently selected from halo, alkyl, alkoxyalkyl and aryl; or wherein two adjacent substituents of the cycloalkyl together with the carbon atoms to which they are attached form a heterocyclyl group. In one embodiment $R^c$ is cyclopropyl, 1-methylcyclobutyl, 1-phenylcyclopropyl, 1-methylcyclopropyl, 2,2-difluorocyclopropyl,

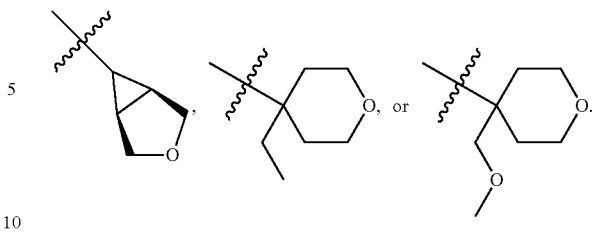

(b). Within the embodiments one and two in embodiment 12, in a second subembodiment $R^c$ is unsubstituted alkyl. In one embodiment $R^c$ is isopropyl or tert-butyl.

(c). Within the embodiments one and two in embodiment 11, in one subembodiment $R^c$ is -(alkylene)-$NR^6R^7$ (where $R^6$ and $R^7$ are independently hydrogen, alkyl, haloalkyl, hydroxyalkyl, alkoxyalkyl, cycloalkyl, or heterocyclyl. In another subembodiment $R^c$ is —$C(CH_3)_2NH_2$, —$C(CH_3)_2NHCH_3$, —$C(CH_3)_2N(CH_3)_2$, —$C(CH_3)_2$—$NHCH_2CH_3$, —$C(CH_3)_2NHCH(CH_3)_2$, —$C(CH_3)_2NHcyclopropyl$, —$C(CH_3)_2NH(CH_2)_2OCH_3$, —$C(CH_3)_2OCH_2CH_3$, —$C(CH_3)_2N(CH_2CH_3)(oxetan-3-yl)$, —$C(CH_3)_2N(CH_3)(oxetan-3-yl)$, or —$C(CH_3)_2NH(oxetan-3-yl)$.

(d) Within the embodiments one and two in embodiment 12, in another subembodiment $R^c$ is heterocyclylalkyl wherein the heterocyclyl in heterocyclylalkyl is optionally substituted with one, two, or three substituents where two of the optional substituents are independently selected from alkyl, alkoxy, hydroxy, halo, amino, and oxo, and one of the optional substituent is alkyl, hydroxyalkyl, alkoxyalkyl, acyl, haloalkyl, alkylsulfonyl, alkoxycarbonyl, or heterocyclyl wherein the heterocyclyl is optionally substituted with one or two substitutents independently selected from alkyl, halo, hydroxy, and alkoxy.

In one subembodiment of subembodiment (d), $R^c$ is —$C(CH_3)_2morpholine-4-yl$, —$C(CH_3)_2$-4-(2,2,2-trifluoroethyl)piperazin-1-yl, —$C(CH_3)_2$-4-(1-methyl)piperidin-1-yl,

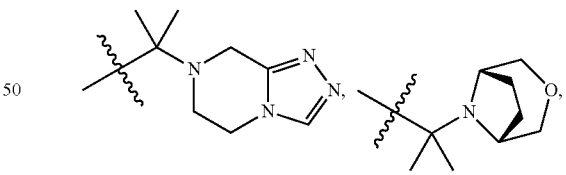

—$C(CH_3)_2$-4-ethyl-3-oxopiperazin-1-yl, $C(CH_3)_2$tetrahydropyran-4-yl, —$C(CH_3)_2$-4-methoxycarbonylpiperazin-1-yl, —$C(CH_3)_2$-4-(oxetan-4-yl)piperazin-1-yl, —$C(CH_3)_2$-4-(3-methyloxetan-4-yl)piperazin-1-yl, —$C(CH_3)_2$-4-t-butoxycarbonylpiperazin-1-yl, —$C(CH_3)_2$-4-acetylpiperazin-1-yl, —$C(CH_3)_2$-4-methoxycarbonylpiperazin-1-yl, —$C(CH_3)_2$-piperazin-1-yl, —$C(CH_3)_2$-3,3-difluoropyrrolidin-1-yl, —$C(CH_3)_2$—(S)-3-methoxypyrrolidin-1-yl, —$C(CH_3)_2$—(R)-3-methoxypyrrolidin-1-yl, —$C(CH_3)_2$—(S)-2-(methoxymethyl)pyrrolidin-1-yl, —$C(CH_3)_2$—(R)-2-(methoxymethyl)pyrrolidin-1-yl,

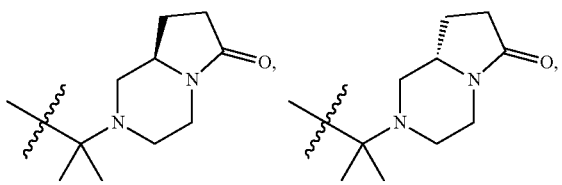 [SMILES: *C(C)(C)N1CCN2C(=O)CC[C@@H]2C1 ; *C(C)(C)N1CCN2C(=O)CC[C@H]2C1] 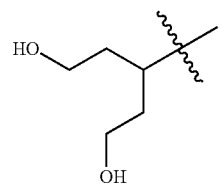

—C(CH₃)₂-4-methylpiperazin-1-yl, —C(CH₃)₂-4-ethylpiperazin-1-yl, —C(CH₃)₂-4-isopropylpiperazin-1-yl, —C(CH₃)₂-4-(2-methoxyethyl)piperazin-1-yl, —C(CH₃)₂-4-acetylpiperazin-1-yl, —C(CH₃)₂-4-(3R,5S)-3,4,5-trimethylpiperazin-1-yl, —C(CH₃)₂-4-(3R,5S)-3,5-dimethylpiperazin-1-yl, —C(CH₃)₂-4-(3R,5S)-dimethylmorpholin-4-yl, —C(CH₃)₂-piperidin-1-yl, —C(CH₃)₂-pyrrolidin-1-yl, —C(CH₃)₂₋₃-oxo-piperazin-1-yl, or —C(CH₃)₂-(3-oxo-4-methylpiperazin-1-yl). In a second subembodiment of subembodiment (d), $R^c$ is heterocyclylalkyl wherein the heterocyclyl in heterocyclylalkyl is substituted with another heterocyclyl wherein the another heterocyclyl is substituted with alkyl on a carbon of the another heterocyclyl.

(e). Within the embodiments one and two in embodiment 12, in yet another subembodiment $R^c$ is heterocyclyl optionally substituted with one, two, or three substituents where two of the optional substituents are independently selected from alkyl, alkoxy, hydroxy, halo, amino, and oxo, and one of the optional substituent is alkyl, hydroxyalkyl, alkoxyalkyl, acyl, or heterocyclyl. In one subembodiment of subembodiment (e), $R^c$ is 3-methyloxetan-3-yl, 3-ethyloxetan-3-yl, 3-fluorooxetan-3-yl, 3-aminooxetan-3-yl, 4-methylpiperidin-4-yl, 3-methylazetidin-3-yl, 1-methylazetidin-3-yl, 4-methyl-4-tetrahydropyranyl or 1,3-dimethylazetidin-3-yl. In another subembodiment (f), $R^c$ is

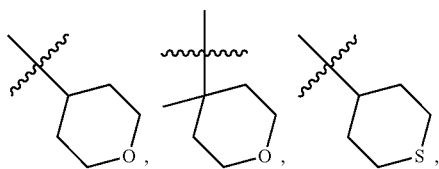

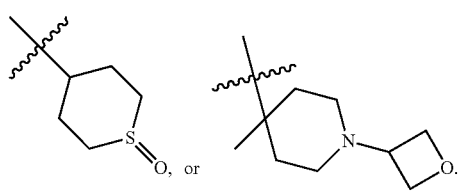

(g) In another subembodiment of embodiment 12, $R^c$ is alkyl which is optionally substituted with one or two substituents independently selected from hydroxy, hydoxyalkyl, and heteroaryl which is substituted with one or two substituents independently selected from alkyl and heterocyclyl wherein heterocyclyl is optionally substituted with one or two substituents independently selected from halo and alkyl. In another embodiment, $R^c$ is alkyl which is substituted with one or two hydroxy substituents. In another embodiment, $R^c$ is In a subembodiment, $R^c$ is alkyl which is substituted with a heteroaryl that is optionally substituted with one or two substituents independently selected from alkyl and heterocyclyl wherein heterocyclyl is optionally substituted with one or two substituents independently selected from halo and alkyl. Within this subembodiment, in another embodiment, $R^c$ is

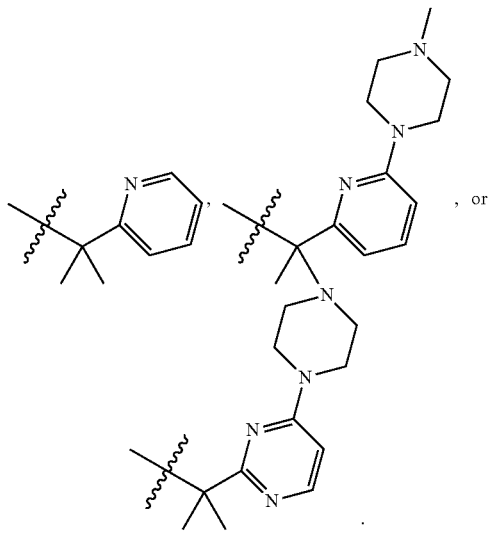

In another subembodiment, $R^c$ is alkyl that is substituted with —CONR⁹R¹⁰, where $R^9$ and $R^{10}$ are independently hydrogen or alkyl, or $R^9$ and $R^{10}$ together with the nitrogen atom to which they are attached form a heterocyclyl optionally substituted with one or two substituents selected from alkyl and heterocyclyl. Within this subembodiment is an embodiment wherein $R^9$ and $R^{10}$ are both hydrogen or alkyl. In another embodiment, $R^c$ is —C(CH₃)₂—CONH₂ or —C(CH₃)₂—CON(CH₃)₂.

In another subembodiment, $R^c$ is alkyl that is substituted with —CONR⁹R¹⁰, wherein $R^9$ and $R^{10}$ together with the nitrogen atom to which they are attached form a heterocyclyl optionally substituted with one or two substituents selected from alkyl and heterocyclyl. Within this subembodiment is an embodiment wherein the heterocyclyl formed by $R^9$ and $R^{10}$ together with the nitrogen atom to which they are attached is 4-methylpiperazinyl, or 4-(oxetan-3-yl)piperazin-1-yl.

13. The compounds of any of the embodiments 3, 5, 6, and 8-10 (i.e., A is —N—; —X—Ar is attached to carbon at the 4-position of the phenyl ring, the carbon of the phenyl ring attached to N of the cyclic urea ring being position 1; X is O; Y is a bond; ring Z is pyrrolidinyl or piperidinyl and is attached to the cyclic urea nitrogen at the C-3 carbon, the nitrogen atom of pyrrolidinyl or piperidinyl ring being C-1; the stereochemistry at carbon of the pyrrolidinyl or piperidinyl attached to the cyclic nitrogen being (R)), wherein $R^5$ is a group of formula (i), $R^a$ is cyano, $R^b$ is hydrogen and $R^c$ is heterocyclylalkyl, wherein heterocyclyl in heterocyclylalkyl is optionally substituted with one, two, or three substituents where two of the optional substituents are independently selected from alkyl, alkoxy, hydroxy, halo, amino, and oxo, and one of the optional substituent is alkyl, hydroxyalkyl, alkoxy, alkoxyalkyl, acyl, haloalkyl, alkylsulfonyl, alkoxycarbonyl, or heterocyclyl wherein the heterocyclyl is substituted with one or two substitutents independently selected from hydrogen, alkyl, halo, hydroxy, and alkoxy.

In a subembodiment of this embodiment, $R^c$ is

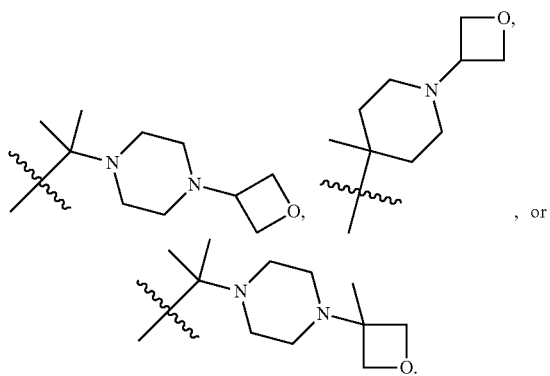

Representative compounds are listed in Table I below:

TABLE I

| Cpd # | Name | MS M + 1 |
|---|---|---|
| 1 | (R)-2-(3-(4-amino-2-oxo-3-(4-phenoxyphenyl)-2,3-dihydro-1H-imidazo[4,5-c]pyridin-1-yl)piperidine-1-carbonyl)-4,4-dimethylpent-2-enenitrile | 537.2 |
| 2 | (R)-2-(3-(4-amino-2-oxo-3-(4-phenoxyphenyl)-2,3-dihydro-1H-imidazo[4,5-c]pyridin-1-yl)piperidine-1-carbonyl)-3-(tetrahydro-2H-pyran-4-yl)acrylonitrile | 565.5 |
| 3 | (R)-2-(3-(4-amino-2-oxo-3-(4-phenoxyphenyl)-2,3-dihydro-1H-imidazo[4,5-c]pyridin-1-yl)piperidine-1-carbonyl)-3-(1-methylcyclobutyl)acrylonitrile | 549.4 |
| 4 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-morpholinopent-2-enenitrile | 608.3 |
| 5 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile | 663.3 |
| 6 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(4-(2,2,2-trifluoroethyl)piperazin-1-yl)pent-2-enenitrile | 689.3 |
| 7 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(1-methylpiperidin-4-yl)pent-2-enenitrile | 620.4 |
| 8 | (R)-2-(3-(4-amino-2-oxo-3-(4-phenoxyphenyl)-2,3-dihydro-1H-imidazo[4,5-c]pyridin-1-yl)piperidine-1-carbonyl)-3-cyclobutylacrylonitrile | 535.4 |
| 9 | (R)-2-(3-(4-amino-2-oxo-3-(4-phenoxyphenyl)-2,3-dihydro-1H-imidazo[4,5-c]pyridin-1-yl)piperidine-1-carbonyl)-4-(4-(2-methoxyethyl)piperazin-1-yl)-4-methylpent-2-enenitrile | 665.3 |
| 10 | (R)-methyl 4-(5-(3-(4-amino-2-oxo-3-(4-phenoxyphenyl)-2,3-dihydro-1H-imidazo[4,5-c]pyridin-1-yl)piperidin-1-yl)-4-cyano-2-methyl-5-oxopent-3-en-2-yl)piperazine-1-carboxylate | 665.3 |
| 11 | (R)-2-(3-(4-amino-2-oxo-3-(4-phenoxyphenyl)-2,3-dihydro-1H-imidazo[4,5-c]pyridin-1-yl)piperidine-1-carbonyl)-6-hydroxy-4-(2-hydroxyethyl)hex-2-enenitrile | 583.2 |
| 12 | (S)-2-(2-((4-amino-2-oxo-3-(4-phenoxyphenyl)-2,3-dihydro-1H-imidazo[4,5-c]pyridin-1-yl)methyl)pyrrolidine-1-carbonyl)-4,4-dimethylpent-2-enenitrile | 537.0 |
| 13 | (S)-2-(2-((4-amino-2-oxo-3-(4-phenoxyphenyl)-2,3-dihydro-1H-imidazo[4,5-c]pyridin-1-yl)methyl)pyrrolidine-1-carbonyl)-4-methyl-4-(4-(oxetan-3-yl)piperazin-1-yl)pent-2-enenitrile | 662.8 |
| 14 | (S)-2-(2-((4-amino-2-oxo-3-(4-phenoxyphenyl)-2,3-dihydro-1H-imidazo[4,5-c]pyridin-1-yl)methyl)pyrrolidine-1-carbonyl)-4-methyl-4-morpholinopent-2-enenitrile | 607.8 |
| 15 | (S)-methyl 4-(5-(2-((4-amino-2-oxo-3-(4-phenoxyphenyl)-2,3-dihydro-1H-imidazo[4,5-c]pyridin-1-yl)methyl)pyrrolidin-1-yl)-4-cyano-2-methyl-5-oxopent-3-en-2-yl)piperazine-1-carboxylate | 665.7 |
| 16 | (R)-1-(1-acryloylpiperidin-3-yl)-4-amino-3-(4-phenoxyphenyl)-1H-imidazo[4,5-c]pyridin-2-(3H)-one | 456.2 |
| 17 | (R)-4-amino-1-(1-(but-2-ynoyl)piperidin-3-yl)-3-(4-phenoxyphenyl)-1H-imidazo[4,5-c]pyridin-2(3H)-one | 468.2 |
| 18 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(4-methyl-3-oxopiperazin-1-yl)pent-2-enenitrile | 635.3 |
| 19 | 2-((R)-3-(4-amino-2-oxo-3-(4-phenoxyphenyl)-2,3-dihydro-1H-imidazo[4,5-c]pyridin-1-yl)piperidine-1-carbonyl)-4-((3R,5S)-3,5-dimethylpiperazin-1-yl)-4-methylpent-2-enenitrile | 635.3 |
| 20 | (R)-2-(3-(4-amino-2-oxo-3-(4-phenoxyphenyl)-2,3-dihydro-1H-imidazo[4,5-c]pyridin-1-yl)piperidine-1-carbonyl)-3-(tetrahydro-2H-thiopyran-4-yl)acrylonitrile | 581.2 |
| 21 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(3-oxopiperazin-1-yl)pent-2-enenitrile | 621.3 |
| 22 | (S)-1-((1-acryloylpyrrolidin-2-yl)methyl)-4-amino-3-(4-phenoxyphenyl)-1H-imidazo[4,5-c]pyridin-2(3H)-one | 455.9 |
| 23 | (S)-4-amino-1-((1-(but-2-ynoyl)pyrrolidin-2-yl)methyl)-3-(4-phenoxyphenyl)-1H-imidazo[4,5-c]pyridin-2(3H)-one | 467.9 |
| 24 | (R)-2-(3-(4-amino-3-(4-(2,6-difluorophenoxy)phenyl)-2-oxo-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile | 699.3 |
| 25 | (R)-2-(3-(4-amino-3-(4-(2,3-difluorophenoxy)phenyl)-2-oxo-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile | 699.2 |
| 26 | (R)-2-(3-(4-amino-3-(3-fluoro-4-phenoxyphenyl)-2-oxo-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile | 681.4 |
| 27 | (R)-2-(3-(4-amino-3-(2-fluoro-4-phenoxyphenyl)-2-oxo-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile | 681.3 |
| 28 | (R)-2-(3-(4-amino-3-(3-methyl-4-phenoxyphenyl)-2-oxo-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile | 677.3 |
| 29 | (R)-2-(3-(4-amino-2-oxo-3-(4-phenoxyphenyl)-2,3-dihydro-1H-imidazo[4,5-c]pyridin-1-yl)piperidine-1-carbonyl)-4-(5,6-dihydro-[1,2,4]triazolo[4,3-a]pyrazin-7(8H)-yl)-4-methylpent-2-enenitrile | 645.3 |
| 30 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(4-(3-methyloxetan-3-yl)piperazin-1-yl)pent-2-enenitrile | 677.3 |
| 31 | (R)-2-(3-(6-amino-8-oxo-7-(4-phenoxyphenyl)-7H-purin-9(8H)-yl)piperidine-1-carbonyl)-4-methyl-4-(4-(oxetan-3-yl)piperazin-1-yl)pent-2-enenitrile | 663.8 |
| 32 | (R)-2-(3-(6-amino-8-oxo-7-(4-phenoxyphenyl)-7H-purin-9(8H)-yl)piperidine-1-carbonyl)-3-(4-methyl-1-(oxetan-3-yl)piperidin-4-yl)acrylonitrile | 635.0 |
| 33 | (R)-2-(3-(6-amino-8-oxo-7-(4-phenoxyphenyl)-7H-purin-9(8H)-yl)piperidine-1-carbonyl)-4-methyl-4-(4-(3-methyloxetan-3-yl)piperazin-1-yl)pent-2-enenitrile | |

TABLE I-continued

| Cpd # | Name | MS M + 1 |
|---|---|---|
| 34 | (S)-2-(2-((4-amino-2-oxo-3-(4-phenoxyphenyl)-2,3-dihydro-1H-imidazo[4,5-c]pyridin-1-yl)methyl)pyrrolidine-1-carbonyl)-4-methyl-4-(4-methylpiperazin-1-yl)pent-2-enenitrile | 620.9 |
| 35 | (S)-2-(2-((4-amino-2-oxo-3-(4-phenoxyphenyl)-2,3-dihydro-1H-imidazo[4,5-c]pyridin-1-yl)methyl)pyrrolidine-1-carbonyl)-4-methyl-4-(4-methyl-3-oxopiperazin-1-yl)pent-2-enenitrile | 635.0 |
| 36 | (S)-2-(2-((4-amino-2-oxo-3-(4-phenoxyphenyl)-2,3-dihydro-1H-imidazo[4,5-c]pyridin-1-yl)methyl)pyrrolidine-1-carbonyl)-4-methyl-4-(methyl(oxetan-3-yl)amino)pent-2-enenitrile | 607.9 |
| 37 | (R)-2-(3-(4-amino-2-oxo-3-(4-phenoxyphenyl)-2,3-dihydro-1H-imidazo[4,5-c]pyridin-1-yl)piperidine-1-carbonyl)-3-(4-methyltetrahydro-2H-pyran-4-yl)acrylonitrile | 579.2 |
| 38 | (R)-2-(3-(4-amino-3-(4-(2-fluorophenoxy)phenyl)-2-oxo-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile | 681.3 |
| 39 | (R)-2-(3-(4-amino-2-oxo-3-(4-phenoxyphenyl)-2,3-dihydro-1H-imidazo[4,5-c]pyridin-1-yl)piperidine-1-carbonyl)-3-(1-oxidotetrahydro-2H-thiopyran-4-yl)acrylonitrile | 597.2 |
| 40 | (R)-2-(3-(4-amino-2-oxo-3-(4-phenoxyphenyl)-2,3-dihydro-1H-imidazo[4,5-c]pyridin-1-yl)piperidine-1-carbonyl)-4-(4-ethyl-3-oxopiperazin-1-yl)-4-methylpent-2-enenitrile | 649.3 |
| 41 | (R)-2-(3-(4-amino-2-oxo-3-(4-phenoxyphenyl)-2,3-dihydro-1H-imidazo[4,5-c]pyridin-1-yl)piperidine-1-carbonyl)-3-cyclopropylacrylonitrile | 521.2 |
| 42 | (R)-2-(3-(4-amino-2-oxo-3-(4-phenoxyphenyl)-2,3-dihydro-1H-imidazo[4,5-c]pyridin-1-yl)piperidine-1-carbonyl)-3-(4-methyl-1-(oxetan-3-yl)piperidin-4-yl)acrylonitrile | 635.3 |
| 43 | (R)-tert-butyl 4-(5-(3-(4-amino-2-oxo-3-(4-phenoxyphenyl)-2,3-dihydro-1H-imidazo[4,5-c]pyridin-1-yl)piperidin-1-yl)-4-cyano-2-methyl-5-oxopent-3-en-2-yl)piperazine-1-carboxylate | 707.5 |
| 44 | (R)-4-(4-acetylpiperazin-1-yl)-2-(3-(4-amino-2-oxo-3-(4-phenoxyphenyl)-2,3-dihydro-1H-imidazo[4,5-c]pyridin-1-yl)piperidine-1-carbonyl)-4-methylpent-2-enenitrile | 649.3 |
| 45 | 2-((R)-3-(4-amino-2-oxo-3-(4-phenoxyphenyl)-2,3-dihydro-1H-imidazo[4,5-c]pyridin-1-yl)piperidine-1-carbonyl)-4-((1R,5S)-3-oxa-8-azabicyclo[3.2.1]octan-8-yl)-4-methylpent-2-enenitrile | 634.5 |
| 46 | (R)-2-(3-(4-amino-2-oxo-3-(4-phenoxyphenyl)-2,3-dihydro-1H-imidazo[4,5-c]pyridin-1-yl)piperidine-1-carbonyl)-3-(1-phenylcyclopropyl)acrylonitrile | 597.4 |
| 47 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(piperazin-1-yl)pent-2-enenitrile | 607.4 |
| 48 | (R)-2-(3-(4-amino-2-oxo-3-(4-phenoxyphenyl)-2,3-dihydro-1H-imidazo[4,5-c]pyridin-1-yl)piperidine-1-carbonyl)-3-(1-methylcyclopropyl)acrylonitrile | 535.3 |
| 49 | (R)-2-(3-(4-amino-2-oxo-3-(4-phenoxyphenyl)-2,3-dihydro-1H-imidazo[4,5-c]pyridin-1-yl)piperidine-1-carbonyl)-4,4-dimethyl-5-(4-methylpiperazin-1-yl)-5-oxopent-2-enenitrile | 648.7 |
| 50 | (R)-5-(3-(4-amino-2-oxo-3-(4-phenoxyphenyl)-2,3-dihydro-1H-imidazo[4,5-c]pyridin-1-yl)piperidin-1-yl)-4-cyano-N,N,2,2-tetramethyl-5-oxopent-3-enamide | 593.9 |
| 51 | (R)-2-(3-(4-amino-2-oxo-3-(4-phenoxyphenyl)-2,3-dihydro-1H-imidazo[4,5-c]pyridin-1-yl)piperidine-1-carbonyl)-4,4-dimethyl-5-(4-(oxetan-3-yl)piperazin-1-yl)-5-oxopent-2-enenitrile | 690.7 |
| 52 | (R)-2-(3-(4-amino-2-oxo-3-(4-phenoxyphenyl)-2,3-dihydro-1H-imidazo[4,5-c]pyridin-1-yl)piperidine-1-carbonyl)-3-(2,2-difluorocyclopropyl)acrylonitrile | 557.2 |
| 53 | 2-((R)-3-(4-amino-2-oxo-3-(4-phenoxyphenyl)-2,3-dihydro-1H-imidazo[4,5-c]pyridin-1-yl)piperidine-1-carbonyl)-3-((1R,5S)-3-oxabicyclo[3.1.0]hexan-6-yl)acrylonitrile | 563.2 |
| 54 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(6-(4-methylpiperazin-1-yl)pyridin-2-yl)pent-2-enenitrile | 698.0 |
| 55 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(pyridin-2-yl)pent-2-enenitrile | 599.7 |
| 56 | (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(4-(4-methylpiperazin-1-yl)pyrimidin-2-yl)pent-2-enenitrile | 698.9 |
| 57 | (R)-4-amino-2-(3-(4-amino-2-oxo-3-(4-phenoxyphenyl)-2,3-dihydro-1H-imidazo[4,5-c]pyridin-1-yl)piperidine-1-carbonyl)-4-methylpent-2-enenitrile | 538.3 |
| 58 | (R)-2-(3-(4-amino-2-oxo-3-(4-phenoxyphenyl)-2,3-dihydro-1H-imidazo[4,5-c]pyridin-1-yl)piperidine-1-carbonyl)-4-(3,3-difluoropyrrolidin-1-yl)-4-methylpent-2-enenitrile | 628.3 |
| 59 | 2-((R)-3-(4-amino-2-oxo-3-(4-phenoxyphenyl)-2,3-dihydro-1H-imidazo[4,5-c]pyridin-1-yl)piperidine-1-carbonyl)-4-((S)-3-methoxypyrrolidin-1-yl)-4-methylpent-2-enenitrile | 622.2 |
| 60 | 2-((R)-3-(4-amino-2-oxo-3-(4-phenoxyphenyl)-2,3-dihydro-1H-imidazo[4,5-c]pyridin-1-yl)piperidine-1-carbonyl)-4-((R)-3-methoxypyrrolidin-1-yl)-4-methylpent-2-enenitrile | 622.3 |
| 61 | 2-((R)-3-(4-amino-2-oxo-3-(4-phenoxyphenyl)-2,3-dihydro-1H-imidazo[4,5-c]pyridin-1-yl)piperidine-1-carbonyl)-4-methyl-4-((R)-6-oxohexahydropyrrolo[1,2-a]pyrazin-2(1H)-yl)pent-2-enenitrile | 661.4 |
| 62 | 2-((R)-3-(4-amino-2-oxo-3-(4-phenoxyphenyl)-2,3-dihydro-1H-imidazo[4,5-c]pyridin-1-yl)piperidine-1-carbonyl)-4-((R)-2-(methoxymethyl)pyrrolidin-1-yl)-4-methylpent-2-enenitrile | 636.4 |
| 63 | 2-((R)-3-(4-amino-2-oxo-3-(4-phenoxyphenyl)-2,3-dihydro-1H-imidazo[4,5-c]pyridin-1-yl)piperidine-1-carbonyl)-4-((S)-2-(methoxymethyl)pyrrolidin-1-yl)-4-methylpent-2-enenitrile | 636.3 |
| 64 | 2-((R)-3-(4-amino-2-oxo-3-(4-phenoxyphenyl)-2,3-dihydro-1H-imidazo[4,5-c]pyridin-1-yl)piperidine-1-carbonyl)-4-methyl-4-((S)-6-oxohexahydropyrrolo[1,2-a]pyrazin-2(1H)-yl)pent-2-enenitrile | 661.3 |
| 65 | (R)-2-(3-(4-amino-2-oxo-3-(4-phenoxyphenyl)-2,3-dihydro-1H-imidazo[4,5-c]pyridin-1-yl)piperidine-1-carbonyl)-3-(4-ethyltetrahydro-2H-pyran-4-yl)acrylonitrile | 593.2 |
| 66 | (R)-2-(3-(4-amino-2-oxo-3-(4-phenoxyphenyl)-2,3-dihydro-1H-imidazo[4,5-c]pyridin-1-yl)piperidine-1-carbonyl)-3-(4-(methoxymethyl)tetrahydro-2H-pyran-4-yl)acrylonitrile | 609.3 |
| 67 | (R)-4-amino-1-(1-(2-fluoroacryloyl)piperidin-3-yl)-3-(4-phenoxyphenyl)-1H-imidazo[4,5-c]pyridin-2(3H)-one | 474.1 |

E or Z isomer of any of the compounds of Table 1, and/or a pharmaceutically acceptable salt of any of these compounds are also included within the scope of the present invention The present invention is also directed to the following compounds:

4-amino-1-((3S)-1-(oxirane-2-carbonyl)piperidin-3-yl)-3-(4-phenoxyphenyl)-1H-imidazo[4,5-c]pyridin-2(3H)-one;

4-amino-1-((3S)-1-(2,3-dihydroxypropanoyl)piperidin-3-yl)-3-(4-phenoxyphenyl)-1H-imidazo[4,5-c]pyridin-2(3H)-one;

4-amino-1-((3 S)-1-(2-hydroxypropanoyl)piperidin-3-yl)-3-(4-phenoxyphenyl)-1H-imidazo[4,5-c]pyridin-2(3H)-one;

(S)-4-amino-1-(1-(3-hydroxypropanoyl)piperidin-3-yl)-3-(4-phenoxyphenyl)-1H-imidazo[4,5-c]pyridin-2(3H)-one;

4-amino-1-(((2R)-1-(oxirane-2-carbonyl)pyrrolidin-2-yl)methyl)-3-(4-phenoxyphenyl)-1H-imidazo[4,5-c]pyridin-2(3H)-one;

4-amino-1-(((2R)-1-(2,3-dihydroxypropanoyl)pyrrolidin-2-yl)methyl)-3-(4-phenoxyphenyl)-1H-imidazo[4,5-c]pyridin-2(3H)-one;

4-amino-1-(((2R)-1-(2-hydroxypropanoyl)pyrrolidin-2-yl)methyl)-3-(4-phenoxyphenyl)-1H-imidazo[4,5-c]pyridin-2(3H)-one; and (R)-4-amino-1-((1-(3-hydroxypropanoyl)pyrrolidin-2-yl)methyl)-3-(4-phenoxyphenyl)-1H-imidazo[4,5-c]pyridin-2(3H)-one;

and/or a pharmaceutically acceptable salt thereof.

These compounds may be prepared according to Scheme 4 set forth below and have the same utility as the compounds of formula (I).

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., or from about 0° C. to about 125° C. or at about room (or ambient) temperature, e.g., about 20° C.

Compounds of Formula (I) where $R^5$ is a group of formula (i) and other groups as defined in the Summary can be prepared as illustrated and described in Scheme 1 below.

Scheme 1

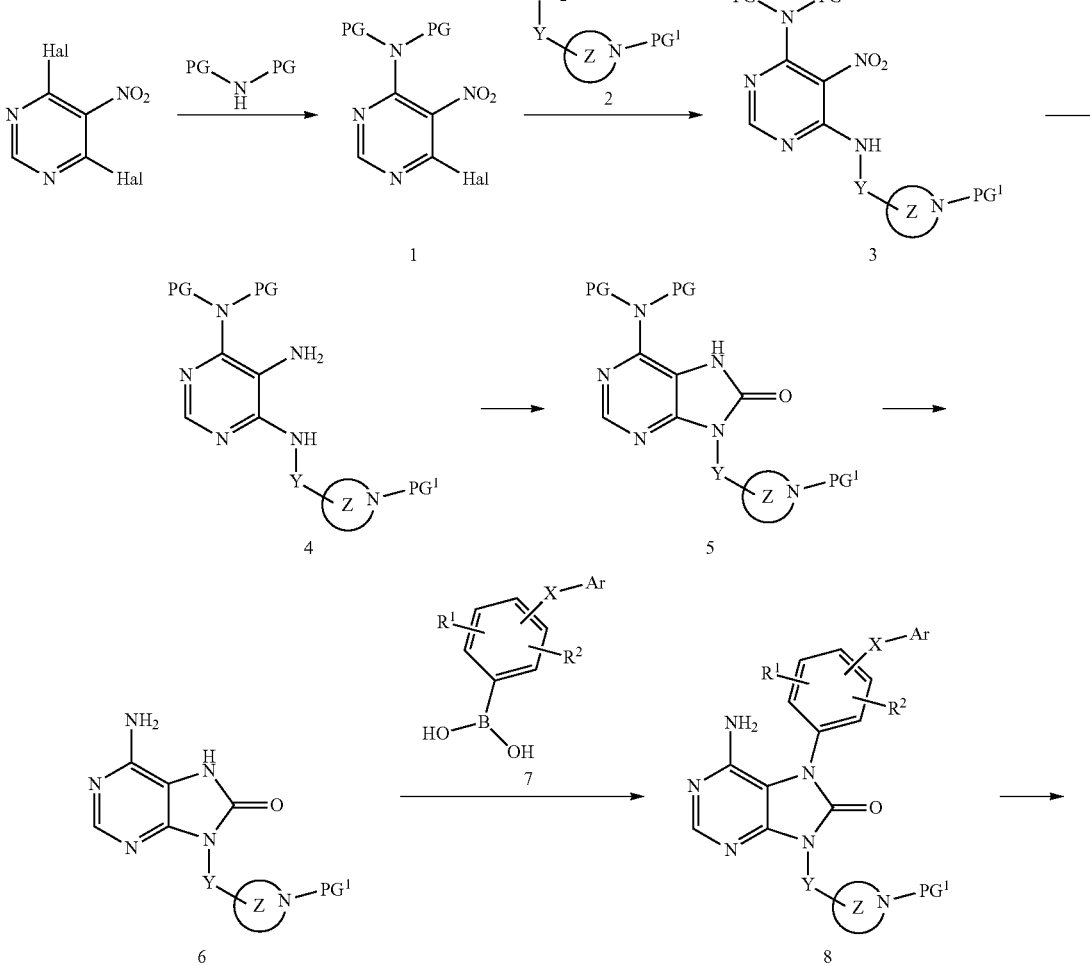

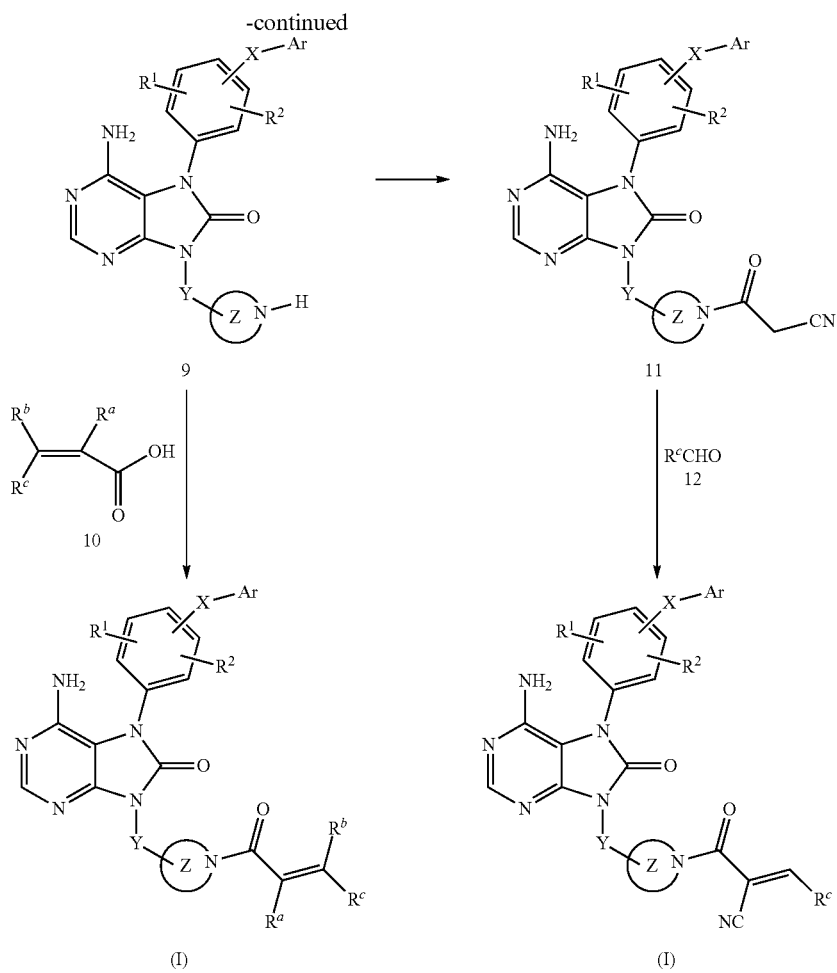

Reaction of a dihaloheteroaryl compound such as 4,6-dichloro-5-nitropyrimidine with an amine of formula NH(PG)$_2$ where PG is a suitable amino protecting group such as benzyl provides a compound of formula 1. The reaction is carried out in a suitable organic solvent such as dioxane, dichloromethane, and the like. Displacement of the second halo group by an amino compound of formula 2 where Y and ring Z are as defined in the Summary and PG$^1$ is a suitable amino protecting group such as Boc, yields a compound of formula 3. The reaction is carried out in dichloromethane, dioxane, tetrahydrofuran, and the like with additional base such as triethylamine. Compounds of formula 2 such as (R)-tert-butyl 3-aminopiperidine-1-carboxylate, (S)-tert-butyl 3-aminopiperidine-1-carboxylate, (R)-tert-butyl 3-(aminomethyl)pyrrolidine-1-carboxylate, (S)-tert-butyl 3-(aminomethyl)pyrrolidine-1-carboxylate, (R)-tert-butyl 2-(aminomethyl)azetidine-1-carboxylate, and (S)-tert-butyl 2-(aminomethyl)azetidine-1-carboxylate, are commercially available or can be prepared by methods well known in the art. The nitro group of compounds of formula 3 can be reduced with reagents such as Zn and ammonium chloride in EtOAc or with Fe or SnCl in a solvent such as acetic acid in EtOH to afford compounds of formula 4.

Compounds of formula 4 can be cyclized to form the benzimidazolones of formula 5 by heating 4 in an organic solvent such as dichloroethane and the like, with carbonyl diimidazole, phosgene or a phosgene equivalent (e.g., diphosgene or triphosgene), in the presence of a base such as triethyl amine, diisopropylethyl amine, and the like. Removal of the amino protecting group PG provides compound of formula 6. The reaction conditions utilized are based on the nature of the amino protecting group. For example, when PG is a benzyl group it can be removed via hydrogenation using a Pd/C catalyst and the like with an additive such as acetic acid to afford a compound of formula 6. Reaction of 6 with an aryl boronic acid of formula 7 where R$^1$, R$^2$, Ar, and X are as defined in the Summary via a copper mediated coupling (Chan-Lam coupling) using, for example, Cu(OAc)2 as a catalyst in a solvent such as DCM, with an additive such TEMP or oxygen and a base such as pyridine or triethylamine affords a compound of formula 8. Compounds of formula 7, e.g (4-phenoxyphenyl)boronic acid, 2-[4-(3-fluorophenoxy)-phenyl]-4,4,5,5-tetramethyl-1,3,2-dioxaborolane, 4-(4-fluorophenoxy)phenylboronic acid, 4-(3-fluorophenoxy)phenylboronic acid, 4-(3,5-difluorophenoxy)-phenylboronic acid, 4-(4-chloro-2-fluorophenoxy)phenyl-boronic acid, and 4-(3-(trifluoromethyl)phenoxy)phenyl boronic acid are either commercially available or can be prepared from the phenyl halide by lithium halogen exchange and quenching with triisopropyl borate.

Alternatively, compound 8 can be prepared by reacting compound 5 first with boronic acid 7, followed by removal of the amino protecting group under conditions described above. Removal of the amino protecting group PG$^1$ in compound 8 provides compound of formula 9. The reaction conditions utilized are based on the nature of the amino protecting group. For example, when PG¹ is Boc it can be removed under acid hydrolysis reaction conditions such as treatment with an acid such TFA, HCl, and the like.

Compound 9 can be then converted to a compound of Formula (I) by methods well known in the art. For example, compounds of Formula (I) can be prepared by coupling compound 9 with an acid of formula 10 or an acid derivative of compound 10 such as acid chloride, where $R^a$, $R^b$, and $R^c$ are as described in the Summary to give a compound of Formula (I). When compound 10 is used, the reaction is carried out under standard amide coupling conditions such as in the presence of HATU, DCC, carbon diimidazole (CDI) and the like. Compounds of formula 10 or acid chloride derivatives thereof are commercially available (e.g. acryloyl chloride) or they can be prepared by methods well known in the art, such as the condensation product of cyanoacetic acid and an aldehyde such as isobutyraldeyde or pivaldehyde.

Compound of Formula (I) where $R^a$ is cyano also be prepared by first condensing compound 9 with 2-cyano-acetic acid under standard amide coupling conditions such as carbon diimidazole (CDI) and the like to give a compound of formula 11. Condensation of a compound of formula 11 with an aldehyde of formula $R^cCHO$ where $R^c$ is as defined in the Summary under standard condensation reaction conditions such as using a base such as piperidine and the like, in the presence or absence of acetic acid and the like, in solvents such as ethanol and the like at temperatures ranging from room temperature to reflux then provides a compound of Formula (I). Compounds of formula $R^cCHO$ are commercially available or they can be prepared by methods well known in the art, e.g., acetaldehyde, cyclopropylaldehyde, isobutyraldehyde, 3-methyloxetane-3-carbaldehyde, 2-(di-methylamino)-2-methylpropanal, 2-methyl-2-(1-piperidyl)propanal, tert-butyl (2S)-2-formylpyrrolidine-1-carboxylate and 2-methyl-2-(morpholin-4-yl)propanal are commercially available. Ethoxy-2-methylpropanal was prepared from isobutyraldehyde as described in PCT Int. Appl., 2007142576. Compounds $R^cCHO$ where $R^c$ is -(alkylene)-$NR^6R^7$ can be prepared by treatment of isobutryaldehyde with bromine to form bromoisobutyraldehyde followed displacement of the bromide by addition of $HNR^6R^7$.

Alternatively, compound 11 can also be condensed with a precursor group of $R^cCHO$ and then converted to a compound of Formula (I). For example, compound 11 can be condensed with tert-butyl 2-methyl-1-oxopropan-2-ylcarbamate followed by removal of the amino protecting group to give a compound of Formula (I) where $R^c$ is 2-aminopropan-2-yl. The condensation reaction can be also be carried out by adding the desired aldehyde $R^cCHO$ with a base such as pyrrolidine or piperidine with or without chlorotrimethylsilane in dichloromethane or other suitable solvent (e.g. dioxane and ethanol). Compounds of Formula (I) where $R^5$ is a group of formula (ii)-(iv) can be prepared as described in scheme 2. By following the procedure described above and substituting compound 9 with suitable starting materials, such as 2-butynoic acid, vinylsulfonyl chloride, (E)-prop-1-ene-1-sulfonyl chloride, 1-propyne-1-sulfonyl chloride, compounds of formula (I) can be obtained.

Alternatively, to prepare compounds of formula (I) where $R^5$ is a group of formula (ii), compounds of formula 11 can be reacted with cyanomethanesulfonyl chloride, available commercially, to afford a cyanomethylsulfonamide which can be condensed with aldehydes of formula 12 with TMSCl and pyrrolidine to afford structures of formula (I).

Scheme 2

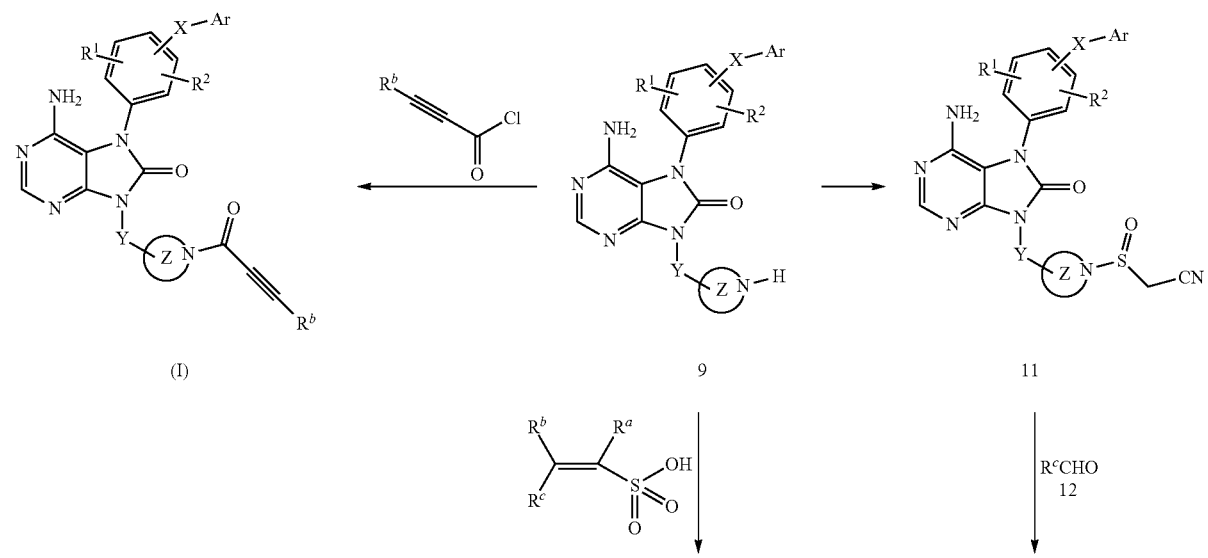

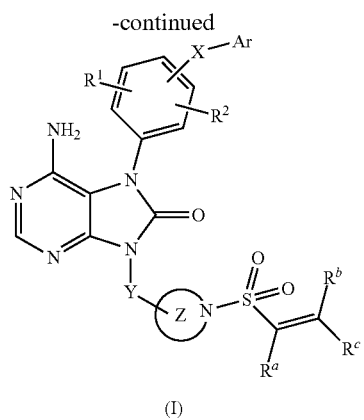

(I)

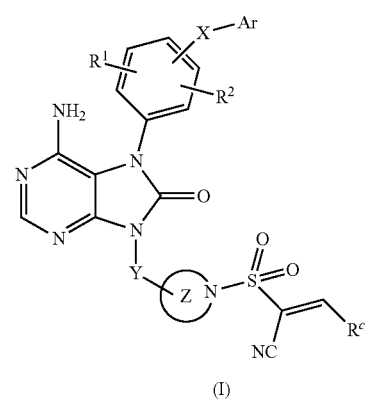

(I)

Compounds of formula (I) where A=CH can be prepared as described in scheme 3. 2,4-dichloro-3-nitropyridine can first be reacted with an amino compound of formula 2 where Y and ring Z are as defined in the Summary and PG$^1$ is a suitable amino protecting group such as Boc. Subsequent reaction with an amine of formula NH(PG)$_2$ where PG is a suitable amino protecting group such as 4-methoxybenzyl in a solvent such as DMF afford a compound of formula 14. Reduction of the nitro group by hydrogenation with Pd/C or by reduction with Zn, Fe, or SnCl under standard conditions, affords a compound of formula 15. Condensation with carbonyldiimidazole or a phosgene equivalent affords the cyclic urea 16. Chan-Lam coupling can be performed at this stage and the syntheses of compounds (I) completed as described in Scheme 1.

Alternatively, compound 17 can be prepared by treating first with an acid such as TFA to remove both protecting groups and subsequently installing the PG$^1$ (e.g. Boc) group. Subsequent treatment with dimethylformamide dimethyl acetal affords a compound of formula 18. Reacting under Chan-Lam conditions as described above then affords compound 19. Subsequent deprotection by treatment of 19 with an acid such as HCl or TFA in solvents such as Dichloromethane, dioxane, MeOH, or EtOH affords a compound of formula 20. Preparation of compounds of formula (I) are then prepared in analogous fashion to the methods described in Schemes 1 and 2.

Scheme 3

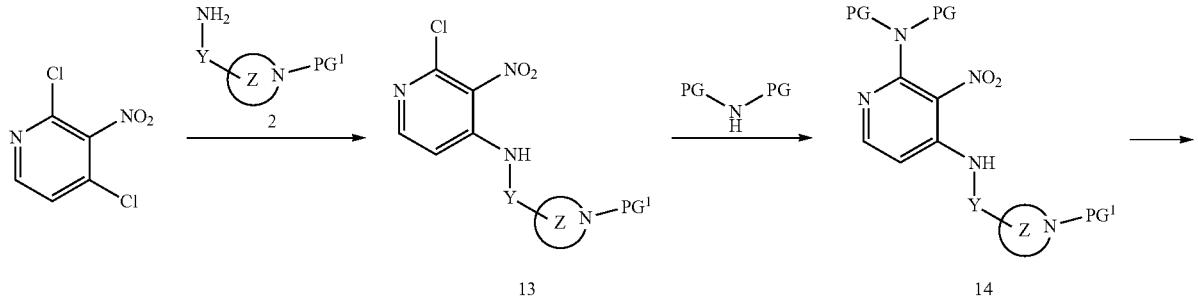

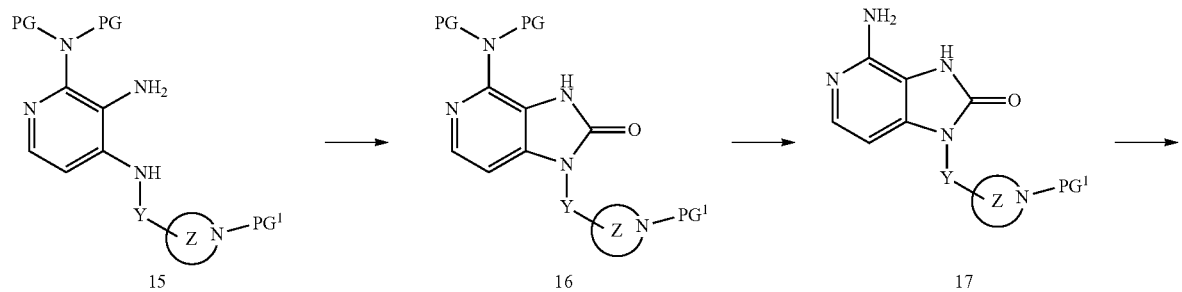

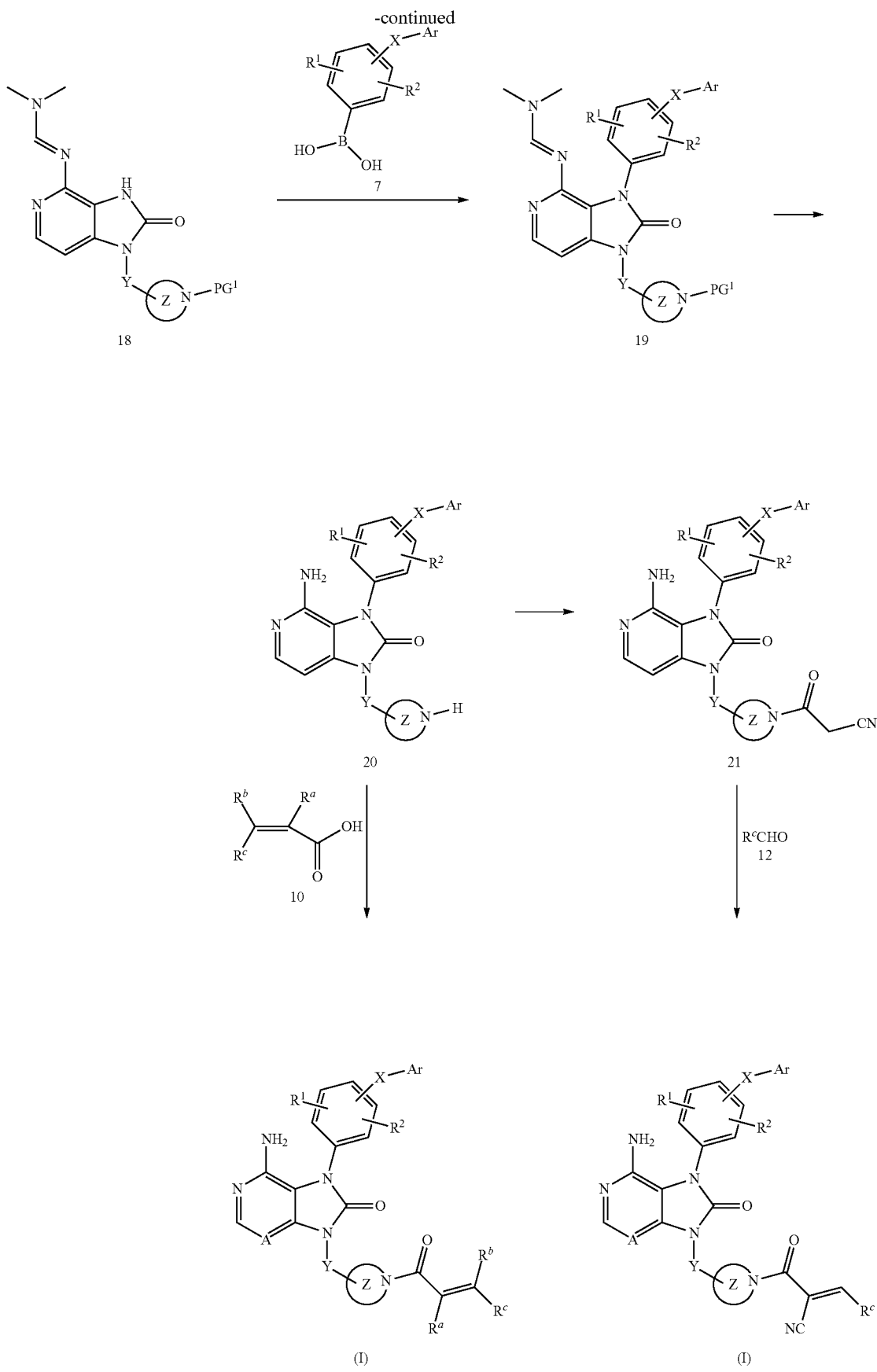

scheme 4 below shows the preparation of the compounds of formula 21, 22, 24, and 25. Coupling of a commercially available acid such as 3-hydroxypropanoic acid or 2-hydroxypropanoic acid (as a racemate or as the (S) or (R) isomer) with compound 20 from scheme 2 using a reagent such as HATU in a solvent such as DMF affords compounds of formula 21 and 22 respectively. Acryloyl chloride may be added to compound 20 in a solvent such as DMF with a base such as trimethylamine or diisopropylethylamine to afford a compound of formula 23. Oxidation with reagents such as osmium tetroxide and N-methyl morpholine oxide (NMO) in a mixture of acetone and water affords diols of formula 24. Compound 25 can be prepared from a compound of formula 23 by oxidation with an oxidant such as mCPBA in a solvent such as toluene or dichloromethane or by tert-butyl hydrogen peroxide (TBHP) and a cinchona alkaloid catalyst (Sharpless epoxidation).

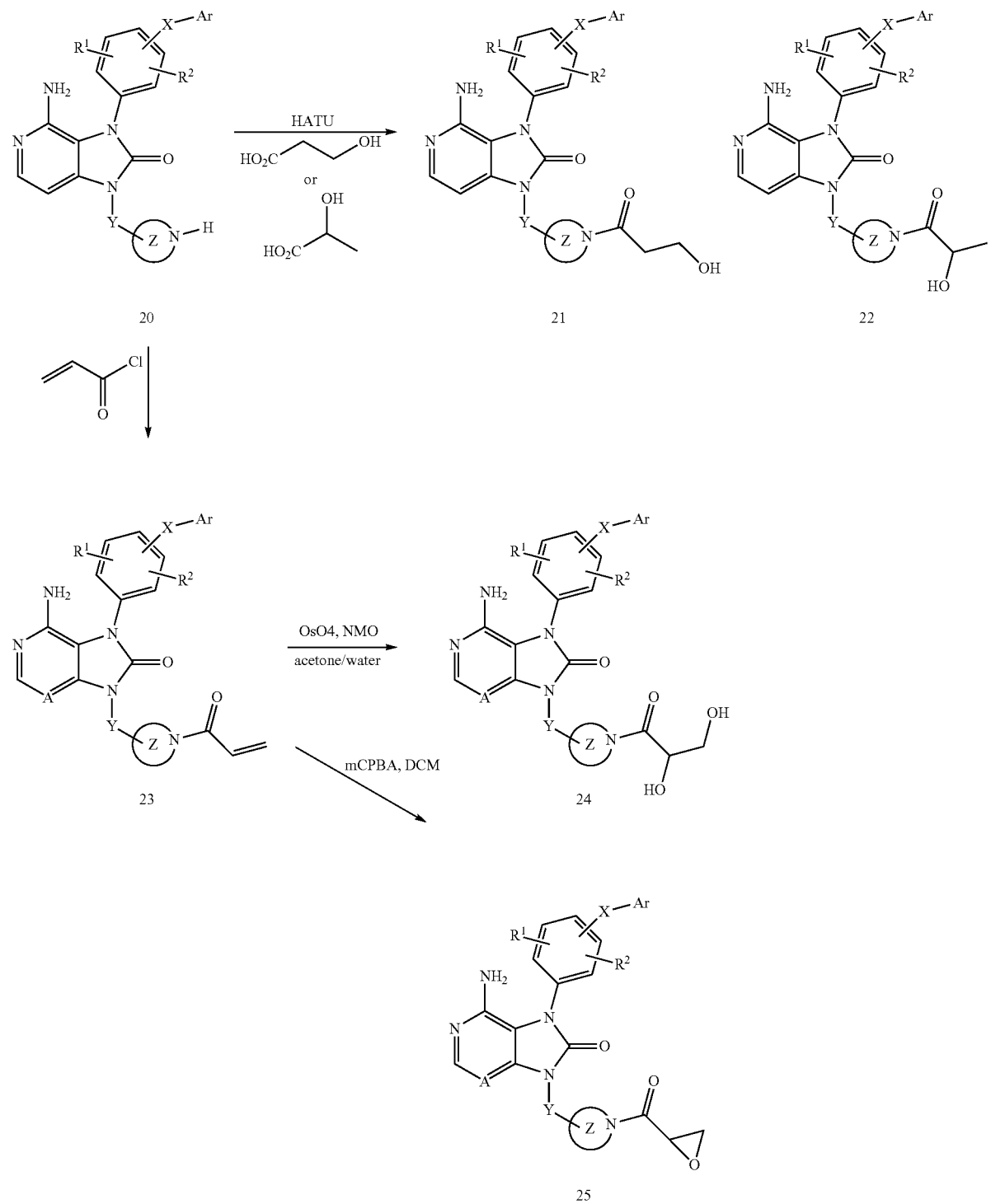

Scheme 4

General Method A

Some other compounds can be prepared using the general method shown below.

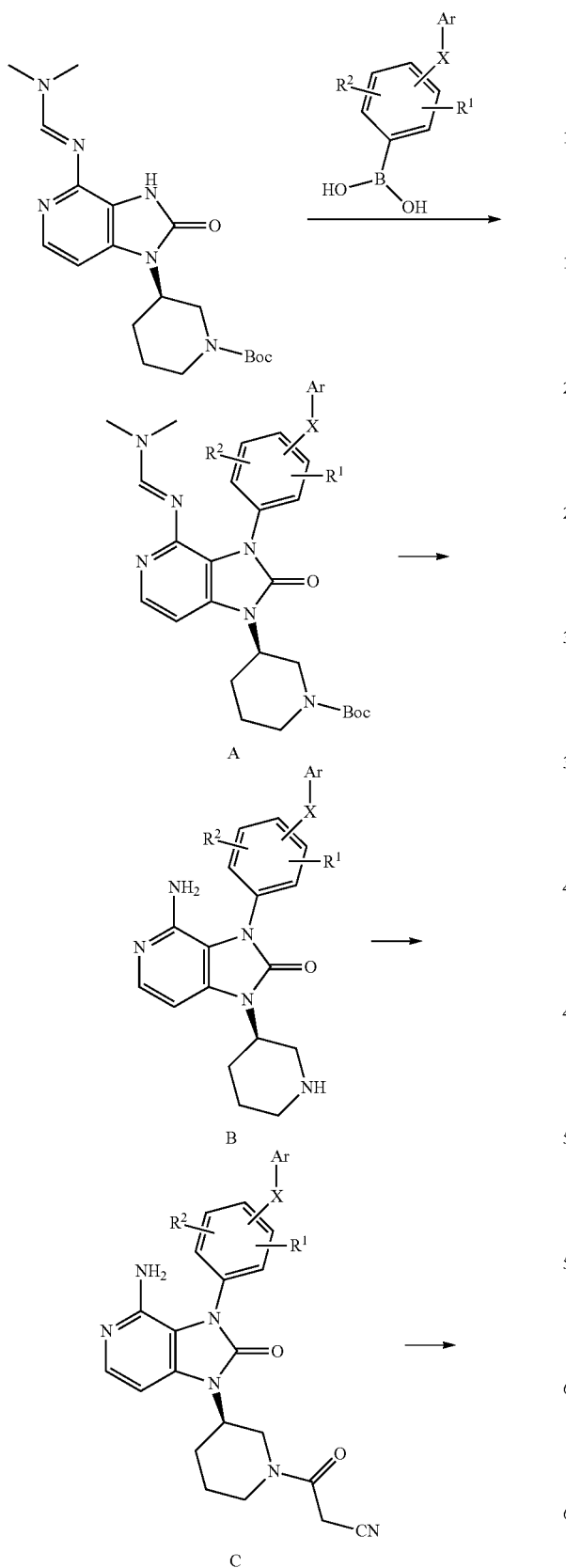

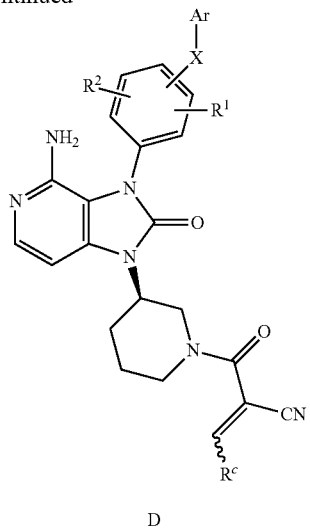

Step 1

Into a 100-mL round-bottom flask purged and maintained with an atmosphere of O2, was placed the aryl boronic acid (1.0 equiv), TEA (4.0 equiv), Cu(OAc)2 (0.50 equiv), TEMPO (1.10 equiv) and mol sieves (4 A) (500 mg) in dichloromethane (0.1 mM). The resulting solution was stirred for 30 min and then the arylboronic acid (2.00 equiv) was added. The resulting solution was stirred overnight at rt. The resulting mixture was concentrated under vacuum. The residue was applied onto a silica gel column eluting with dichloromethane/methanol to afford the desired product A.

Step 2

To a solution of A (1.0 equiv) in dioxane was added hydrogen chloride (12M). The resulting solution was stirred for 3 h at 85° C. in an oil bath. The reaction was then quenched by the addition of sodium bicarbonate(sat.). The resulting solution was extracted with DCM/MeOH (10:1) and the organic layers combined. The resulting mixture was washed with saturated sodium chloride. The mixture was dried over anhydrous sodium sulfate and concentrated under vacuum. This resulted in 360 mg (100%) of B.

Step 3

Into a 50-mL round-bottom flask, was placed B (1.0 equiv), 2-cyanoacetic acid (1.0 equiv), HATU (1.5 equiv), TEA (3.0 equiv) and N,N-dimethylformamide (0.1 mMol). The resulting solution was stirred for 2 h at it. The resulting solution was extracted with dichloromethane and the organic layers combined. The resulting mixture was washed with 6×100 mL of water. The mixture was dried over anhydrous sodium sulfate and concentrated under vacuum. The residue was applied onto a silica gel column with dichloromethane/methanol to afford compound C.

Step 4

Into a round bottomed flask was placed C (1.0 equiv) which was dissolved in DCM to a concentration of 0.2M. The solution was cooled to 0° C., and the aldehyde (3.0 equiv) was added followed by pyrrolidine (6.0 equiv) and TMSCl (4.0 equiv). The reaction was warmed to rt and stirred for 3 h or until the sm was consumed. Water was added and the layers separated. The organic layer was dried over sodium sulfate, filtered and the solvent removed in vacuo. Purification by either silica gel chromatography or preparative HPLC afforded the desired compounds D. Aldehydes were either purchased commercially, by the method shown below or by methods known in the literature (i.e. oxidation of an alcohol via Swern conditions or with an oxidant such as PCC or Dess-Martin periodinane).

General Method B

Preparation of aldehydes from isobutyraldehyde

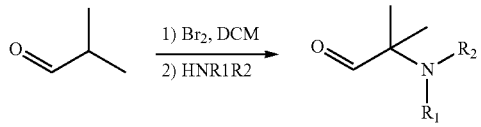

To a solution of 2-methylpropanal (1.0 equiv) in DCM (0.2M) cooled with an ice bath was added bromine (1.0 equiv) dropwise. After 1 hr, most solvent was removed from the resulting 2-bromo-2-methylpropanal solution in vacuo. This material was diluted in DCM (8 ml) at rt and amine (2.0 equiv) was added. After stirring overnight, the mixture was diluted with brine (30 mL) and the layers separated. The organic layer is dried (MgSO$_4$), filtered and concentrated to isolate the desired aldehyde which is either used directly in the next step or purified by silica gel chromatography prior to use.

Testing

The BTK inhibitory activity, residence time of the inhibitor BTK bound complex, and the ability of the of the compounds of the present disclosure to form an irreversible covalent bond or a reversible covalent bond with Cys 481 (UniprotKB Sequence ID Q06187) of BTK can be tested using the in vitro and/or in vivo assays described in Biological Examples below.

The BTK inhibitory activity of the compound of Formula (I) and/or a pharmaceutically acceptable salt thereof of the present disclosure can be tested using the in vitro and/or in vivo assays described in Biological Examples 1, 3, 4, and 5 below. A determination of kinase inhibitory activity by any of those assays is considered to be kinase inhibitory activity within the scope of this disclosure even if any or all of the other assays do not result in a determination of kinase inhibitory activity.

Without being bound to any specific mechanistic theory, in those embodiments where the compound of the present disclosure is a reversible covalent inhibitor, it is believed that the cysteine sulfhydryl group and a carbon atom forming part of the carbon-carbon double bond in the $R^5$ group in a compound of Formula (I) where $R^5$ is a group of formula (i), (ii) or (iii) where $R^a$ is cyano, (see Formula (I)) can form a reversible, i.e., labile, covalent bond, such as wherein Cys 481 of BTK attacks an electron deficient carbon atom of the carbon-carbon double bond in the above listed $R^5$ groups in the compound of present disclosure to form a thiol adduct.

In some embodiments, the electron deficient carbon atom of the olefin is distal to the carbon attached to the $R^a$ group (where $R^a$ is cyano) i.e., the carbon atom attached to the $R^b$ and $R^c$ group (see Formula (I) in the compounds of the present disclosure). Therefore, the combination of the $R^a$ group (where $R^a$ is cyano) and the "—N—CO—, —NSO$_2$ or —N—SO—" moieties and the olefinic moiety to which they are bonded in the compounds of the present disclosure can increase the reactivity of the olefin to form a thiol adduct with the active site cysteine residue in BTK.

The compounds of the present disclosure which are reversible covalent inhibitors can bind with BTK in two different manners. In addition to the labile covalent binding, discussed above, they are believed to also form non-covalent binding (e.g., via van der Waals binding, hydrogen binding, hydrophobic binding, hydrophilic binding, and/or electrostatic charge binding) with BTK, the non-covalent binding sufficient to at least partially inhibit the kinase activity of the BTK.

As disclosed herein, the labile covalent binding occurs between the olefin in the inhibitor and the cysteine 481 residue thiol side chain at or near the site where the inhibitor has the aforementioned non-covalent binding with the BTK.

As is evident, the compounds of the present disclosure which are reversible covalent inhibitors have both a cysteine-mediated covalent binding and a non-covalent binding with the BTK. This is in contrast with non-covalent reversible inhibitors which inhibit the BTK only via non-covalent binding and lack the cysteine-mediated covalent binding.

The binding of the compounds of the present disclosure with BTK in the two different manners mentioned above provides a reversible covalent inhibitor having a slow off-rate and a protracted duration of action, in some instances comparable to an irreversible covalent inhibitor without forming permanent irreversible protein adducts. The difference between irreversible and reversible covalent inhibitors, particularly the compounds disclosed herein, can be ascertained utilizing assays disclosed herein.

In general, the binding involved an inhibitor that forms a reversible covalent bond with BTK which is stable when the BTK is in certain configurations and susceptible to being broken when the BTK is in different configurations (in both cases under physiologic conditions), whereas the interaction between an inhibitor that forms an irreversible covalent bond with BTK is stable under physiologic conditions even when the BTK is in different configurations.

A reversible covalent bond often imparts unique properties related to the residence time of the compound within the cysteine-containing binding site. In this context, residence time refers to the temporal duration of the compound-target complex under different conditions (see Copeland R A, Pompliano D L, Meek T D. Drug-target residence time and its implications for lead optimization. *Nat. Rev. Drug Discov.* 5(9), 730-739 (2006).

The presence of a reversible covalent bond in a reversible covalent inhibitor as disclosed herein can lead to an extended residence time when compared to a compound that does not form a covalent bond with BTK. In one embodiment disclosed herein the compounds of the present disclosure that are reversible covalent inhibitors have a residence time of at least about 1 h. Residence time may be measured using an occupancy assay in a biochemical or cellular environment (see Biological Example 2 and 9 below). Additionally, residence time may be measured using a functional assay following a defined wash-out period.

Compounds that form an irreversible covalent bond in an irreversible covalent inhibitor share these extended residence time properties but may nonetheless be differentiated from reversible covalent inhibitor using a reversibility assay. The ability of the compound of the disclosure to form reversible or irreversible covalent bond with Cys481 of BTK, can be determined by the assays described in Biological Examples 2, 6-8 below. A determination of the binding reversibility of the covalent bond between the cysteine residue and the olefinic bond of the compound of the disclosure by any of Biological Examples 2, 6-8 below is considered to be reversible binding within the scope of this disclosure even if one or both of the other methods does not result in a determination of binding reversibility.

Administration and Pharmaceutical Composition

In general, the compounds of this disclosure will be administered in a therapeutically effective amount by any of the accepted modes of administration for agents that serve similar utilities. Therapeutically effective amounts of compounds of Formula (I) may range from about 0.01 to about 500 mg per kg patient body weight per day, which can be administered in single or multiple doses. In one embodiment, the dosage level will be about 0.1 to about 250 mg/kg per day. In another embodiment the dosage level will be about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions may be provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the subject, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. Bioavailablity of drugs that decompose at stomach pH can be increased by administration of such drugs in a formulation that releases the drug intraduodenally.

The compositions are comprised of in general, a compound of Formula (I) and/or a pharmaceutically acceptable salt thereof in combination with a pharmaceutically acceptable excipient such as binders, surfactants, diluents, buffering agents, antiadherents, glidants, hydrophilic or hydrophobic polymers, retardants, stabilizing agents or stabilizers, disintegrants or superdisintegrants, antioxidants, antifoaming agents, fillers, flavors, colors, lubricants, sorbents, preservatives, plasticizers, or sweeteners, or mixtures thereof, which facilitate processing of the compound of Formula (I) (or embodiments thereof disclosed herein) and/or a pharmaceutically acceptable salt thereof into preparations which can be used pharmaceutically. Any of the well-known techniques and excipients may be used as suitable and as understood in the art, see for example, Remington: The Science and Practice of Pharmacy, Twenty-first Ed., (Pharmaceutical Press, 2005); Liberman, H. A., Lachman, L., and Schwartz, J. B. Eds., Pharmaceutical Dosage Forms, Vol. 1-2 Taylor & Francis 1990; and R. I. Mahato, Ansel's Pharmaceutical Dosage Forms and Drug Delivery Systems, Second Ed. (Taylor & Francis, 2012).

In certain embodiments, the formulations may include one or more pH adjusting agents or buffering agents, for example, acids such as acetic, boric, citric, fumaric, maleic, tartaric, malic, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate, ammonium chloride, and the like. Such buffers used as bases may have other counterions than sodium, for example, potassium, magnesium, calcium, ammonium, or other counterions. Such acids, bases and buffers are included in an amount required to maintain pH of the composition in an acceptable range.

In certain embodiments, the formulations may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In certain embodiments, the formulations may also include one or more antifoaming agents to reduce foaming during processing which can result in coagulation of aqueous dispersions, bubbles in the finished film, or generally impair processing. Exemplary anti-foaming agents include silicon emulsions or sorbitan sesquoleate.

In certain embodiments, the formulations may also include one or more antioxidants, such as non-thiol antioxidants, for example, butylated hydroxytoluene (BHT), sodium ascorbate, ascorbic acid or its derivative, and tocopherol or its derivatives. In certain embodiments, antioxidants enhance chemical stability where required. Other agents such as citric acid or citrate salts or EDTA may also be added to slow oxidation.

In certain embodiments, the formulations may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide, and cetylpyridinium chloride.

In certain embodiments, the formulations may also include one or more binders. Binders impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinyl-pyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum mucilage of isapol husks, polyvinylpyrrolidone (e.g., Polyvidone® CL, Kollidon® CL, Polyplasdone® XL-10), larch arabogalactan, Veegum®, polyethylene glycol, polyethylene oxide, waxes, sodium alginate, and the like.

In certain embodiments, the formulations may also include dispersing agents and/or viscosity modulating agents. Dispersing agents and/or viscosity modulating agents include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween®60 or 80, PEG, polyvinylpyrrolidone (PVP; commercially known as Plasdone®), and the carbohydrate-based dispersing agents such as, for example, hydroxypropyl celluloses (e.g., HPC, H-PC-SL, and HPC-L), hydroxypropyl methylcelluloses (e.g., HPMC K100, RPMC K4M, HPMC K15M, and HPMC K100M), carboxymethylcellulose sodium, methylcellulose, hydroxyethyl-cellulose, hydroxypropyl-cellulose, hydroxypropylmethylcellulose phthalate, hydroxypropyl-methylcellulose acetate stearate (HPM-CAS), noncrystalline cellulose, polyethylene oxides, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F10®8, which are block copolymers of ethylene oxide and propylene oxide); and poloxamines (e.g., Tetronic 908®, also known as Poloxamine 908®, which is a tetrafonctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate. In general, binder levels of about 10 to about 70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 90% and more typically up to 70% in tablet formulations is common.

In certain embodiments, the formulations may also include one or more diluents which refer to chemical compounds that are used to dilute the compound of interest prior to delivery. Diluents can also be used to stabilize compounds because they can provide a more stable environment Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); hydroxypropyl-methylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In certain embodiments, the formulations may also include one or more disintegrant which includes both the dissolution and dispersion of the dosage form when contacted with gastrointestinal fluid. Disintegration agents or disintegrants facilitate the breakup or disintegration of a substance. Examples of disintegration agents include a starch, e.g., a natural starch such as corn starch or potato starch, a pregelatinized starch such as National 1551 or sodium starch glycolate such as Promogel® or Explotab®, a cellulose such as a wood product, methylcrystalline cellulose, e.g., Avicel®, Avicel® PH101, Avicel® PH 102, Avicel® PH105, Elceme® P100, Emcocel®, Vivacel®, and Solka-Floc®, methylcellulose, croscarmellose, or a cross-linked cellulose, such as cross-linked sodium carboxymethyl-cellulose (Ac-Di-Sol®), cross-linked carboxymethyl-cellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In certain embodiments, the formulations may also include erosion facilitators. Erosion facilitators include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

In certain embodiments, the formulations may also include one or more filling agents which include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

In certain embodiments, the formulations may also include one or more flavoring agents and/or sweeteners e.g., acacia syrup, acesulfame K, alitame, anise, apple, aspartame, banana, Bavarian cream berry, black currant, butterscotch, calcium citrate, camphor, caramel, cherry, cherry cream chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

In certain embodiments, the formulations may also include one or more lubricants and glidants which are compounds that prevent, reduce or inhibit adhesion or friction of materials. Exemplary lubricants include, e.g., stearic acid, calcium hydroxide, talc, sodium stearyl lumerate, a hydrocarbon such as mineral oil, or hydrogenated vegetable oil such as hydrogenated soybean oil, higher fatty acids and their alkali-metal and alkaline earth metal salts, such as aluminum, calcium, magnesium, zinc, stearic acid, sodium stearates, glycerol, talc, waxes, boric acid, sodium benzoate, sodium acetate, sodium chloride, leucine, a polyethylene glycol (e.g., PEG4000) or a methoxypolyethylene glycol such as Carbowax®, sodium oleate, sodium benzoate, glyceryl behenate, polyethylene glycol, magnesium or sodium lauryl sulfate, colloidal silica such as Syloid®, Cab-O-Sil®, a starch such as corn starch, silicone oil, a surfactant, and the like.

In certain embodiments, the formulations may also include one or more plasticizers which are compounds used to soften the enteric or delayed release coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl citrate, dibutyl sebacate, triethyl cellulose and triacetin. In some embodiments, plasticizers can also function as dispersing agents or wetting agents.

In certain embodiments, the formulations may also include one or more solubilizers which include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins for example Captisol®, ethanol, n-butanol, isopropyl alcohol, cholesterol, bile salts, polyethylene glycol 200-600, glycofurol, transcutol, propylene glycol, and dimethyl isosorbide and the like. In one embodiment, the solubilizer is vitamin E TPGS and/or Captisol® or β-hydroxypropylcyclodextrin.

In certain embodiments, the formulations may also include one or more suspending agents which include compounds such as polyvinylpyrrolidone, e.g., polyvinylpyrrolidone K112, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gun, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monoleate, povidone and the like.

In certain embodiments, the formulations may also include one or more surfactants which include compounds such as sodium lauryl sulfate, sodium docusate, Tween 20, 60 or 80, triacetin, vitamin E TPGS, sorbitan monooleate, polyoxyethylene sorbitan monooleate, polyoxyethylene sorbitan monolaurate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g. octoxynol 10, octoxynol 40. In some embodiments, surfactants may be included to enhance physical stability or for other purposes.

In certain embodiments, the formulations may also include one or more viscosity enhancing agents which include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol alginates, acacia, chitosans and combinations thereof.

In certain embodiments, the formulations may also include one or more wetting agents which include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Pharmaceutical preparations disclosed herein can be obtained by mixing one or more solid excipient such as carrier, binder, filling agent, suspending agent, flavoring agent, sweetening agent, disintegrating agent, dispersing agent, surfactant, lubricant, colorant diluent, solubilizer, moistening agent, plasticizer, stabilizer, penetration enhancer, wetting agent, anti-foaming agent, antioxidant, preservative, or one or more combination thereof with one or more of the compounds described herein, optionally grinding the resulting mixture, and processing the mixture of granules, after adding suitable excipients, if desired, to obtain tablets.

Pharmaceutical preparations disclosed herein also include capsules made of gelatin, as well as soft, sealed capsules made of gelatin and a plasticizer, such as glycerol or sorbitol. Capsules may also be made of polymers such as hypromellose. The capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, lipids, solubilizers, or liquid polyethylene glycols. In addition, stabilizers may be added. All formulations for oral administration should be in dosages suitable for such administration.

These formulations can be manufactured by conventional pharmacological techniques. Conventional pharmacological techniques include, e.g., one or a combination of methods: (1) dry mixing, (2) direct compression, (3) milling, (4) dry or non-aqueous granulation, (5) wet granulation, (6) fusion, or (7) extrusion. See, e.g., Lachman et al., The Theory and Practice of Industrial Pharmacy, 3 ed. (1986). Other methods include, e.g., spray drying, pan coating, melt granulation, granulation, fluidized bed spray drying or coating (e.g., wurster coating), tangential coating, top spraying, tableting, extruding, extrusion/spheronization, and the like.

It should be appreciated that there is considerable overlap between excipients used in the solid dosage forms described herein. Thus, the above-listed additives should be taken as merely exemplary, and not limiting, of the types of excipient that can be included in solid dosage forms described herein. The type and amounts of such excipient can be readily determined by one skilled in the art, according to the particular properties desired.

In some embodiments, the solid dosage forms described herein are enteric coated oral dosage forms, i.e., as an oral dosage form of a pharmaceutical composition as described herein which utilizes an enteric coating to effect the release of the compound in the intestine of the gastrointestinal tract. An "enterically coated" drug and/or tablet refers to a drug and/or tablet that is coated with a substance that remains intact in the stomach but dissolves and releases the drug once the intestine (in one embodiment small intestine) is reached. As used herein "enteric coating", is a material, such as a polymer material or materials which encase the therapeutically active agent core either as a dosage form or as particles. Typically, a substantial amount or all of the enteric coating material is dissolved before the therapeutically active agent is released from the dosage form, so as to achieve delayed dissolution of the therapeutically active agent core or particles in the small and/or large intestine. Enteric coatings are discussed, for example, Loyd, V. Allen, Remington: The Science and Practice of Pharmacy, Twenty-first Ed., (Pharmaceutical Press, 2005; and P. J. Tarcha, Polymers for Controlled Drug Delivery, Chapter 3, CRC Press, 1991. Methods for applying enteric coatings to pharmaceutical compositions are well known in the art, and include for example, U.S. Patent Publication No. 2006/0045822.

The enteric coated dosage form may be a compressed or molded or extruded tablet (coated or uncoated) containing granules, powder, pellets, beads or particles of the compound of Formula (I) (or any embodiments thereof) and/or a pharmaceutically acceptable salt thereof and/or other excipients, which are themselves coated or uncoated provided at least the tablet or the compound of Formula (I) is coated. The enteric coated oral dosage form may also be a capsule (coated or uncoated) containing pellets, beads or granules of the compound of Formula (I) (or any embodiments thereof) and/or a pharmaceutically acceptable salt thereof and/or other excipients, which are themselves coated or uncoated provided at least one of them is coated. Some examples of coatings that were originally used as enteric coatings are beeswax and glyceryl monostearate; beeswax, shellac and cellulose; and cetyl alcohol, mastic and shellac as well as shellac and stearic acid (U.S. Pat. No. 2,809,918); polyvinylacetate and ethyl cellulose (U.S. Pat. No. 3,835,221). More recently, the coatings used are neutral copolymers of polymethacrylic acid esters (Eudragit L30D). (F. W. Goodhart et al, *Pharm. Tech., p.* 64-71, April, 1984); copolymers of methacrylic acid and methacrylic acid methyl ester (Eudragit S), or a neutral copolymer of polymethacrylic acid esters containing metallic stearates (Mehta et al U.S. Pat. Nos. 4,728,512 and 4,794,001), cellulose acetate succinate, and hypromellose phthalate.

Any anionic polymer exhibiting a pH-dependent solubility profile can be used as an enteric coating in the methods and compositions described herein to achieve delivery to the intestine. In one embodiment, delivery to the small intestine. In another embodiment, delivery to the duodenum. In some embodiments the polymers described herein are anionic carboxylic polymers. In other embodiments, the polymers and compatible mixtures thereof, and some of their properties, include, but are not limited to:

Shellac:

Also called purified lac, it is a refined product obtained from the resinous secretion of an insect. This coating dissolves in media of pH>7;

Acrylic Polymers:

The performance of acrylic polymers (primarily their solubility in biological fluids) can vary based on the degree and type of substitution. Examples of suitable acrylic polymers include methacrylic acid copolymers and ammonium methacrylate copolymers. The Eudragit series L, S, and RS (manufactured Rohm Pharma and known as Evonik®) are available as solubilized in organic solvent, aqueous dispersion, or dry powders. The Eudragit series RL, NE, and RS are insoluble in the gastrointestinal tract but are permeable and are used primarily for colonic targeting. The Eudragit series L, L-30D and S are insoluble in stomach and dissolve in the intestine and may be selected and formulated to dissolve at a value of pH greater than 5.5 or as low as greater than 5 or as high as greater than 7;

Cellulose Derivatives:

Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP pseudolatex with particles <1 µm. Other components in Aquateric can include pluronics, Tweens, and acetylated monoglycerides. Other suitable cellulose derivatives include; cellulose acetate tritnellitate (Eastman); methylcellulose (Pharmacoat, Methocel); hydroxypropylmethyl cellulose phthalate (HP-MCP); hydroxypropylmethyl cellulose succinate (HPMCS); and hydroxypropylmethylcellulose acetate succinate (HPM-CAS e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP):

PVAP dissolves in pH>5, and it is much less permeable to water vapor and gastric fluids. Detailed description of above polymers and their pH-dependent solubility can be found at in the article titled "Enteric coated hard gelatin capsules" by Professor Karl Thoma and Karoline Bechtold at http://pop.www.capsugel.com/mediallibrary/enteric-coated-hard-gelatin-capsules.pdf. In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as fluid bed or Wurster coaters, or spray or pan coating are employed to apply coatings. The coating thickness must be sufficient to ensure that the oral dosage form remains intact until the desired site of topical delivery in the intestinal tract is reached.

Colorants, surfactants, anti-adhesion agents, antifoaming agents, lubricants (e.g., carnuba wax or PEG) and other additives may be added to the coatings besides plasticizers to solubilize or disperse the coating material, and to improve coating performance and the coated product.

To accelerate the dissolution of the enteric coat, a half-thickness, double coat of enteric polymer (for instance, Eudragit L30 D-55) may be applied, and the inner enteric coat may have a buffer up to pH 6.0 in the presence of 10% citric acid, followed by a final layer of standard Eudragit L 30 D-55. Applying two layers of enteric coat, each half the thickness of a typical enteric coat, Liu and Basit were able to accelerate enteric coating dissolution compared to a similar coating system applied, unbuffered, as a single layer (Liu, F. and Basit, A. Journal of Controlled Release. 147 (2010) 242-245.)

The intactness of the enteric coating may be measured, for example, by the degradation of the drug within the micropellets. The enteric coated dosage forms or pellets may be tested in dissolution testing first in gastric fluid and separately in intestinal fluid as described in USP to determine its function.

The enteric coated tablets and capsules formulation containing the disclosed compounds can be made by methods well known in the art. For example, tablets containing a compound disclosed herein can be enterically coated with a coating solution containing Eudragit®, diethylphthlate, isopropyl alcohol, talc, and water using a side vented coating pan (Freund Hi-Coater).

Alternatively, a multi-unit dosage form comprising enteric-coated pellets that can be incorporated into a tablet or into a capsule can be prepared as follows.

Core Material:

The core material for the individually enteric coating layered pellets can be constituted according to different principles. Seeds layered with the active agent (i.e., the compound of Formula (I) (including embodiments disclosed herein) and/or a pharmaceutically acceptable sale thereof), optionally mixed with alkaline substances or buffer, can be used as the core material for the further processing. The seeds which are to be layered with the active agent can be water insoluble seeds comprising different oxides, celluloses, organic polymers and other materials, alone or in mixtures or water-soluble seeds comprising different inorganic salts, sugars, non-pareils and other materials, alone or in mixtures. Further, the seeds may comprise the active agent in the form of crystals, agglomerates, compacts etc. The size of the seeds is not essential for the present invention but may vary between approximately 0.1 and 2 mm. The seeds layered with the active agent are produced either by powder or solution/suspension layering using for instance granulation or spray coating layering equipment.

Before the seeds are layered, active agent may be mixed with further components. Such components can be binders, surfactants, fillers, disintegrating agents, alkaline additives or other and/or pharmaceutically acceptable ingredients alone or in mixtures. The binders are for example polymers such as hydroxypropyl methylcellulose (HPMC), hydroxypropyl-cellulose (HPC), carboxymethylcellulose sodium, polyvinyl pyrrolidone (PVP), or sugars, starches or other pharmaceutically acceptable substances with cohesive properties. Suitable surfactants are found in the groups of pharmaceutically acceptable non-ionic or ionic surfactants such as for instance sodium lauryl sulfate.

Alternatively, the active agent optionally mixed with suitable constituents can be formulated into a core material. Said core material may be produced by extrusion/spheronization, balling or compression utilizing conventional process equipment. The size of the formulated core material is approximately between 0.1 and 4 mm and for example, between 0.1 and 2 mm. The manufactured core material can further be layered with additional ingredients comprising the active agent and/or be used for further processing.

The active agent is mixed with pharmaceutical constituents to obtain preferred handling and processing properties and a suitable concentration of the active agent in the final preparation. Pharmaceutical constituents such as fillers, binders, lubricants, disintegrating agents, surfactants and other pharmaceutically acceptable additives may be used.

Alternatively, the aforementioned core material can be prepared by using spray drying or spray congealing technique.

Enteric Coating Layer(s):

Before applying the enteric coating layer(s) onto the core material in the form of individual pellets, the pellets may optionally be covered with one or more separating layer(s) comprising pharmaceutical excipients optionally including alkaline compounds such as pH-buffering compounds. This/these separating layer(s), separate(s) the core material from the outer layers being enteric coating layer(s). This/these separating layer(s) protecting the core material of active agent should be water soluble or rapidly disintegrating in water.

A separating layer(s) can be optionally applied to the core material by coating or layering procedures in suitable equipments such as coating pan, coating granulator or in a fluidized bed apparatus using water and/or organic solvents for the coating process. As an alternative the separating layer(s) can be applied to the core material by using powder coating technique. The materials for the separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium, water soluble salts of enteric coating polymers and others, used alone or in mixtures. Additives such as plasticizers, colorants, pigments, fillers anti-tacking and anti-static agents, such as for instance magnesium stearate, titanium dioxide, talc and other additives may also be included into the separating layer(s).

When the optional separating layer is applied to the core material it may constitute a variable thickness. The maximum thickness of the separating layer(s) is normally only limited by processing conditions. The separating layer may serve as a diffusion barrier and may act as a pH-buffering zone. The optionally applied separating layer(s) is not essential for the invention. However, the separating layer(s) may improve the chemical stability of the active substance and/or the physical properties of the novel multiple unit tableted dosage form.

Alternatively, the separating layer may be formed in situ by a reaction between an enteric coating polymer layer applied on the core material and an alkaline reacting compound in the core material. Thus, the separating layer formed comprises a water soluble salt formed between the enteric coating layer polymer(s) and an alkaline reacting compound which is in the position to form a salt One or more enteric coating layers are applied onto the core material or onto the core material covered with separating layer(s) by using a suitable coating technique. The enteric coating layer material may be dispersed or dissolved in either water or in suitable organic solvents. As enteric coating layer polymers, one or more, separately or in combination, of the following can be used, e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating polymer(s).

The enteric coating layers contain pharmaceutically acceptable plasticizers to obtain the desired mechanical properties, such as flexibility and hardness of the enteric coating layers. Such plasticizers are for instance, but not restricted to triacetin, citric acid esters, phthalic acid esters, dibutyl sebacate, cetyl alcohol, polyethylene glycols, polysorbates or other plasticizers.

The amount of plasticizer is optimized for each enteric coating layer formula, in relation to the selected enteric coating layer polymer(s), selected plasticizer(s) and the applied amount of said polymer(s), in such a way that the mechanical properties, i.e. flexibility and hardness of the enteric coating layer(s), for instance exemplified as Vickers hardness, are adjusted so that if a tablet is desired the acid resistance of the pellets covered with enteric coating layer(s) does not decrease significantly during compression of pellets into tablets. The amount of plasticizer is usually above 5% by weight of the enteric coating layer polymer(s), such as 15-50% and further such as 20-50%. Additives such as dispersants, colorants, pigments polymers e.g. poly(ethylacrylate, methylmethacrylate), anti-tacking and anti-foaming agents may also be included into the enteric coating layer(s). Other compounds may be added to increase film thickness and to decrease diffusion of acidic gastric juices into the acid susceptible material. The maximum thickness of the applied enteric coating is normally only limited by processing conditions and the desired dissolution profile.

Over-Coating Layer:

Pellets covered with enteric coating layer(s) may optionally further be covered with one or more over-coating layer(s). The over-coating layer(s) should be water soluble or rapidly disintegrating in water. The over-coating layer(s) can be applied to the enteric coating layered pellets by coating or layering procedures in suitable equipments such as coating pan, coating granulator or in a fluidized bed apparatus using water and/or organic solvents for the coating or layering process. The materials for over-coating layers are chosen among pharmaceutically acceptable compounds such as, for instance sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and others, used alone or in mixtures. Additives such as plasticizers, colorants, pigments, fillers, anti-tacking and anti-static agents, such for instance magnesium stearate, titanium dioxide, talc and other additives may also be included into the over-coating layer(s). The over-coating layer may further prevent potential agglomeration of enteric coating layered pellets, further it may protect the enteric coating layer towards cracking during the compaction process and enhance the tableting process. The maximum thickness of the applied over-coating layer(s) is normally limited by processing conditions and the desired dissolution profile. The over-coating layer may also be used as a tablet film coating layer.

Enteric coating of soft gelatin capsules may contain an emulsion, oil, microemulsion, self-emulsifying system, lipid, triglycerides, polyethylene glycol, surfactants, other solubilizers and the like, and combinations thereof, to solubilize the active agent. The flexibility of the soft gelatin capsule is maintained by residual water and plasticizer. Moreover, for gelatin capsules the gelatin may be dissolved in water so that spraying must be accomplished at a rate with relatively low relative humidity such as can be accomplished in a fluid bed or Wurster. In addition, drying should be accomplished without removing the residual water or plasticizer causing cracking of the capsule shell. Commercially available blends optimized for enteric coating of soft gelatin capsules such as Instamodel EPD (Enteric Polymeric Dispersion), available from Ideal Cures, Pvt. Ltd. (Mumbai, India). On a laboratory scale enteric coated capsules may be prepared by: a) rotating capsules in a flask or dipping capsules in a solution of the gently heated enteric coating material with plasticizer at the lowest possible temperature or b) in a lab scale sprayer/fluid bed and then drying.

For aqueous active agents, it can be especially desirable to incorporate the drug in the water phase of an emulsion. Such "water-in-oil" emulsion provides a suitable biophysical environment for the drug and can provide an oil-water interface that can protect the drug from adverse effects of pH or enzymes that can degrade the drug. Additionally, such water-in-oil formulations can provide a lipid layer, which can interact favorably with lipids in cells of the body, and can increase the partition of the formulation onto the membranes of cells. Such partition can increase the absorption of drugs in such formulations into the circulation and therefore can increase the bioavailability of the drug.

In some embodiments the water-in-oil emulsion contains an oily phase composed of medium or long chain carboxylic acids or esters or alcohols thereof, a surfactant or a surface active agent, and an aqueous phase containing primarily water and the active agent.

Medium and long chain carboxylic acids are those ranging from $C_8$ to $C_{22}$ with up to three unsaturated bonds (also branching). Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain monocarboxylic acids. Examples of these are linoleic acid, ricinoleic acid, linolenic acid, arachidonic acid and behenolic acid. Useful branched acids include, for example, diacetyl tartaric acid. Unsaturated olefinic chains may also be hydroxylated or ethoxylated to prevent oxidation or to alter the surface properties.

Examples of long chain carboxylic acid esters include, but are not limited to, those from the group of: glyceryl monostearates; glyceryl monopalmitates; mixtures of glyceryl monostearate and glyceryl monopalmitate; glyceryl monolinoleate; glyceryl monooleate; mixtures of glyceryl monopalmitate, glyceryl monostearate, glyceryl monooleate and glyceryl monolinoleate; glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate; acetylated glycerides such as distilled acetylated monoglycerides; mixtures of propylene glycol monoesters, distilled monoglycerides, sodium steroyl lactylate and silicon dioxide; d-alpha tocopherol polyethylene glycol 1000 succinate; mixtures of mono- and di-glyceride esters such as Atmul; calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; stearyl octanoate; $C_8$-$C_{30}$ cholesterol/lavosterol esters; and sucrose long chain carboxylic acid esters. Examples of the self-emulsifying long chain carboxylic acid esters include those from the groups of stearates, pamitates, ricinoleates, oleates, behenates, ricinolenates, myristates, laurates, caprylates, and caproates. In some embodiments the oily phase may comprise a combination of 2 or more of the long chain carboxylic acids or esters or alcohols thereof. In some embodiments medium chain surfactants may be used and the oil phase may comprise a mixture of caprylic/capric triglyceride and $C_8$/$C_{10}$ to mono-/di-glycerides of caprylic acid, glyceryl caprylate or propylene glycol monocaprylate or their mixtures.

The alcohols that can be used are exemplified by the hydroxyl forms of the carboxylic acids exemplified above and also strearyl alcohol.

Surface active agents or surfactants are long chain molecules that can accumulate at hydrophilic/hydrophobic (water/oil) interfaces and lower the surface tension at the interface.

As a result they can stabilise an emulsion. In some embodiments of this invention, the surfactant may comprise: Tween® (polyoxyethylene sorbate) family of surfactants, Span® (sorbitan long chain carboxylic acid esters) family of surfactants, Pluronic® (ethylene or propylene oxide block copolymers) family of surfactants, Labrasol®, Labrafil® and Labrafac®(each polyglycolyzed glycerides) families of surfactants, sorbitan esters of oleate, stearate, laurate or other long chain carboxylic acids, poloxamers (polyethylene-polypropylene glycol block copolymers or Pluronic®), other sorbitan or sucrose long chain carboxylic acid esters, mono and diglycerides, PEG derivatives of caprylic/capric triglycerides and mixtures thereof or mixture of two or more of the above. In some embodiments the surfactant phase may comprise a mixture of Polyoxyethylene (20) sorbitan monooleate (Tween 80®) and sorbitan monooleate (Span 80®).

The aqueous phase may optionally comprise the active agent suspended in water and a buffer.

In some embodiments, such emulsions are coarse emulsions, microemulsions and liquid crystal emulsions. In other embodiments such emulsion may optionally comprise a permeation enhancer. In other embodiments, spray-dried dispersions or microparticles or nanoparticles containing encapsulated microemulsion, coarse emulsion or liquid crystal can be used.

In some embodiments, the solid dosage forms described herein are non-enteric time-delayed release dosage forms. The term "non-enteric time-delayed release" as used herein refers to the delivery so that the release of the drug can be accomplished at some generally predictable location in the intestinal tract more distal to that which would have been accomplished if there had been no delayed release alterations. In some embodiments the method for delay of release is a coating that becomes permeable, dissolves, ruptures, and/or is no longer intact after a designed duration. The coating in the time-delayed release dosage forms can have a fixed time to erode after which the drug is released (suitable coating include polymeric coating such as HPMC, PEO, and the like) or has a core comprised of a superdisinegrant(s) or osmotic agent(s) or water attractant such as a salt, hydrophilic polymer, typically polyethylene oxide or an alkylcellulose, salts such as sodium chloride, magnesium chloride, sodium acetate, sodium citrate, sugar, such as glucose, lactose, or sucrose, or the like, which draw water through a semi-permeable membrane or a gas generating agent such as citric acid and sodium bicarbonate with or without an acid such as citric acid or any of the aforementioned acids incorporated in dosage forms. The semi-permeable membrane, while mostly not permeable to the drug nor the osmotic agent, is permeable to water that permeates at a near constant rate to enter the dosage form to increase the pressure and ruptures after the swelling pressure exceeds a certain threshold over a desired delay time. The permeability through this membrane of the drug should be less than $\frac{1}{10}$ than water and in one embodiment less than $\frac{1}{100}$ the water permeability. Alternatively, a membrane could become porous by leaching an aqueous extractable over a desired delay time.

Osmotic dosage forms have been described in Theeuwes U.S. Pat. No. 3,760,984, and an osmotic bursting dosage form is described in Baker U.S. Pat. No. 3,952,741. This osmotic bursting dosage form can provide a single pulse of release or multiple pulses if different devices with different timings are employed. The timing of the osmotic burst may be controlled by the choice of polymer and the thickness or the area of the semipermeable membrane surrounding the core that contains both the drug and the osmotic agent or attractant. As the pressure in the dosage form increase with additional permeated water, the membrane elongates until its breaking point, and then the drug is released. Alternatively, specific areas of rupture can be created in the membrane by having a thinner, weaker area in the membrane or by adding a weaker material to an area of the coating membrane. Some preferred polymers with high water permeabilities that may be used as semipermeable membranes are cellulose acetate, cellulose acetate butyrate, cellulose nitrate, crosslinked polyvinyl, alcohol, polyurethanes, nylon 6, nylon 6.6, and aromatic nylon. Cellulose acetate is an especially preferred polymer.

In another embodiment, the time-delayed coating that begins its delay to releasing drug after the enteric coating is at least partially dissolved is comprised of hydrophilic, erodible polymers that upon contact with water begin to gradually erode over time. Examples of such polymers include cellulose polymers and their derivatives including, but not limited to, hydroxyalkyl celluloses, hydroxymethyl cellulose, hydroxyethyl cellulose, hydroxypropyl cellulose, hydroxypropylmethyl cellulose, carboxymethylcellulose, microcrystalline cellulose; polysaccharides and their derivatives; polyalkylene oxides, such as polyethylene oxide or polyethylene glycols, particularly high molecular weight polyethylene glycols; chitosan; poly(vinyl alcohol); xanthan gum; maleic anhydride copolymers; poly(vinyl pyrrolidone); starch and starch-based polymers; maltodextrins; poly (2-ethyl-2-oxazoline); poly(ethyleneimine); polyurethane; hydrogels; crosslinked polyacrylic acids; and combinations or blends of any of the foregoing.

Some preferred erodible hydrophilic polymers suitable for forming the erodible coating are poly(ethylene oxide), hydroxypropyl methyl cellulose, and combinations of poly (ethylene oxide) and hydroxypropyl methyl cellulose. Poly (ethylene oxide) is used herein to refer to a linear polymer of unsubstituted ethylene oxide. The molecular weight of the poly(ethylene oxide) polymers can range from about $10^5$ Daltons to about $10^7$. Daltons. A preferred molecular weight range of poly(ethylene oxide) polymers is from about 2 times $10^5$ to 2 times $10^6$ Daltons and is commercially available from The Dow Chemical Company (Midland, Mich.) referred to as SENTRY® POLYOX™ water-soluble resins, NF (National Formulary) grade. When higher molecular weights of polyethylene oxide are used, other hydrophilic agents, such as salts or sugars, like glucose, sucrose, or lactose, that promote erosion or disintegration of this coating, are also included.

The time-delayed dosage form can be a mechanical pill such as an Enterion® capsule or pH sensitive capsule which can release the drug after a pre-programmed time or when it receives a signal which can be transmitted or once it leaves the stomach.

The amount of the compound of the disclosure in a formulation can vary within the full range employed by those skilled in the art. Typically, the formulation will contain, on a weight percent (wt %) basis, from about 0.01-99.99 wt % of a compound of Formula (I) based on the total formulation, with the balance being one or more suitable pharmaceutical excipients. In one embodiment, the compound is present at a level of about 1-80 wt %.

The compounds of the present disclosure may be used in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of the present disclosure is used contemporaneously with one or more other drugs, a pharmaceutical composition in unit dosage form containing such other drugs and the compound of the present disclosure is preferred. However, the combination therapy may also include therapies in which the compound of the present disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound of the present disclosure.

The above combinations include combinations of a compound of the present disclosure not only with one other active compound, but also with two or more other active compounds. Likewise, compounds of the present disclosure may be used in combination with other drugs that are used in the prevention, treatment, control, amelioration, or reduction of risk of the diseases or conditions for which compounds of the present disclosure are useful. Such other drugs may be administered, by a route and in an amount commonly used therefore, contemporaneously or sequentially with a compound of the present disclosure. When a compound of the present disclosure is used contemporaneously with one or more other drugs, a pharmaceutical composition, such as a fixed-combination drug product, containing such other drugs in addition to the compound of the present disclosure is preferred. Accordingly, the pharmaceutical compositions of the present disclosure also include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used.

Where the subject is suffering from or at risk of suffering from an autoimmune disease, an inflammatory disease, or an allergy disease, a compound of Formula (I) and/or a pharmaceutically acceptable salt thereof can be used with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-.alpha. binding proteins (e.g., infliximab, etanercept, or adalimumab), abatacept, anakinra, interferon-.beta., interferon-.gamma., interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subject can be treated with a compound of Formula (I) and/or a pharmaceutically acceptable salt thereof in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel," which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of Formula (I) and/or a pharmaceutically acceptable salt thereof include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound of Formula (I) and/or a pharmaceutically acceptable salt thereof include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of Formula (I) and/or a pharmaceutically acceptable salt thereof include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of Formula (I) and/or a pharmaceutically acceptable salt thereof include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of Formula (I) and/or a pharmaceutically acceptable salt thereof include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of Formula (I) and/or a pharmaceutically acceptable salt thereof include, but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of Formula (I) and/or a pharmaceutically acceptable salt thereof include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an BTK inhibitor compound of the disclosure include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the subject is suffering from or at risk of suffering from a thromboembolic disorder (e.g., stroke), the subject can be treated with a compound of Formula (I) in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

EXAMPLES

The following preparations of compounds of Formula (I) and intermediates (References) are given to enable those skilled in the art to more clearly understand and to practice the present disclosure. They should not be considered as limiting the scope of the disclosure, but merely as being illustrative and representative thereof. The ⌇ line at the alkene carbon, in the compounds below denotes that the compounds are isolated as an undefined mixture of (E) and (Z) isomers.

Reference 1

Synthesis of tert-butyl (R,E)-3-(4-(((dimethylamino)methylene)amino)-2-oxo-2,3-dihydro-1H-imidazo[4,5-c]pyridin-1-yl)piperidine-1-carboxylate

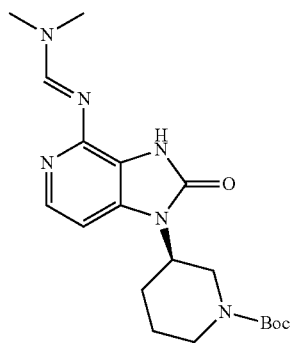 [SMILES: CN(C)/C=N/c1nccc2c1[nH]c(=O)n2[C@@H]1CCCN(C(=O)OC(C)(C)C)C1]

Step 1

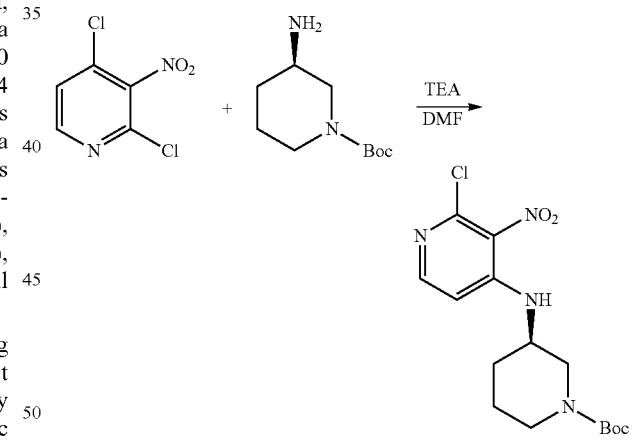

Into a 100-mL round-bottom flask, was placed 2,4-dichloro-3-nitropyridine (8 g, 41.45 mmol, 1.00 equiv), N,N-dimethylformamide (50 mL), tert-butyl (R)-3-aminopiperidine-1-carboxylate (8.3 g, 41.44 mmol, 1.00 equiv), and TEA (6.29 g, 62.16 mmol, 1.50 equiv). The resulting solution was stirred overnight at 25° C. The resulting solution was diluted with $H_2O$, extracted with ethyl acetate and the organic layers were combined. The resulting mixture was washed with saturated sodium chloride and dried over anhydrous sodium sulfate and concentrated. The residue was applied onto a silica gel column and eluted with ethyl acetate/petroleum ether (1:1) to give 8 g (51%) of tert-butyl (R)-3-((2-chloro-3-nitropyridin-4-yl)amino)piperidine-1-carboxylate as a yellow oil.

Step 2

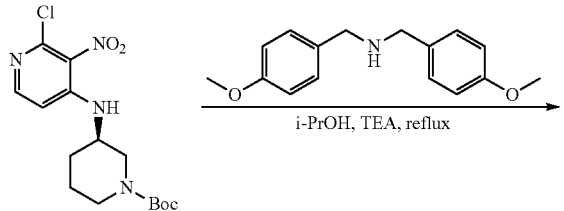

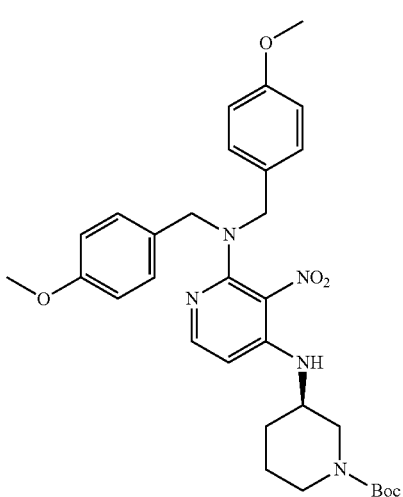

Into a 250-mL round-bottom flask was placed tert-butyl (R)-3-((2-chloro-3-nitropyridin-4-yl)amino)piperidine-1-carboxylate (8 g, 22.42 mmol, 1.00 equiv), i-propanol (100 mL), bis[(4-methoxyphenyl)methyl]amine (5.78 g, 22.46 mmol, 1.00 equiv), and TEA (2.955 g, 29.20 mmol, 1.30 equiv). The resulting solution was stirred overnight at 95° C. The reaction mixture was cooled and concentrated under vacuum. This resulted in 12 g (92%) of tert-butyl (R)-3-((2-(bis(4-methoxybenzyl)amino)-3-nitropyridin-4-yl)amino)piperidine-1-carboxylate as a yellow oil.

Step 3

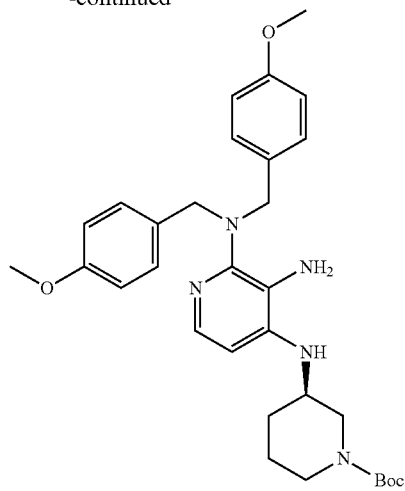

Into a 250-mL round-bottom flask was placed tert-butyl (R)-3-((2-(bis(4-methoxybenzyl)amino)-3-nitropyridin-4-yl)amino)piperidine-1-carboxylate (10 g, 17.31 mmol, 1.00 equiv), AcOH/MeOH (1:1, 100 mL), and Fe (9.69 g, 173.04 mmol, 10.00 equiv). The resulting solution was stirred overnight at 25° C. and then concentrated under vacuum. The pH value of the solution was adjusted to 8.0-9.0 with sodium bicarbonate. The resulting solution was extracted with dichloromethane and the organic layers were washed with sodium bicarbonate, filtered and dried over anhydrous sodium sulfate, then concentrated under vacuum to give 8.8 g (92.8%) of tert-butyl (R)-3-((3-amino-2-(bis(4-methoxybenzyl)-amino)pyridin-4-yl)amino)piperidine-1-carboxylate as a yellow oil.

Step 4

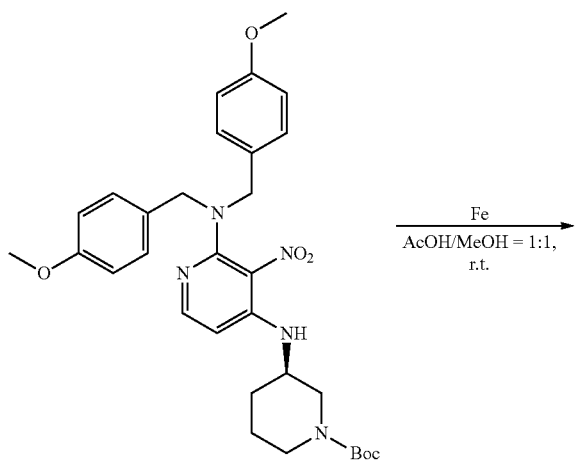

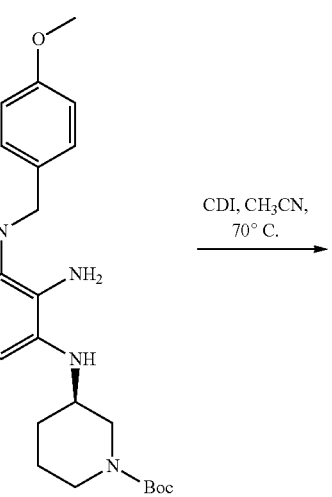

-continued

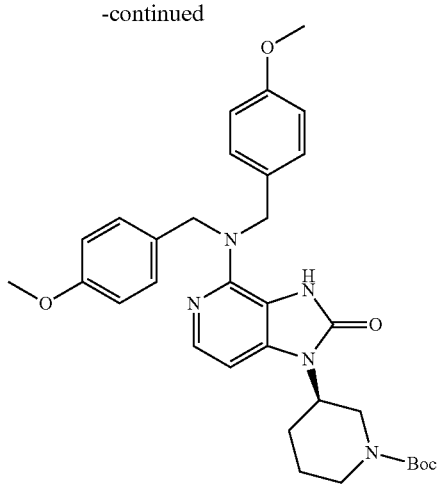

Into a 250-mL round-bottom flask was placed tert-butyl (R)-3-((3-amino-2-(bis(4-methoxy-benzyl)amino)pyridin-4-yl)amino)piperidine-1-carboxylate (12 g, 19.72 mmol, 1.00 equiv, 90%), CH₃CN (100 mL), and CDI (5.336 g, 32.91 mmol, 1.50 equiv). The resulting solution was stirred overnight at 80° C. The reaction mixture was cooled and concentrated. The residue was applied onto a silica gel column and eluted with ethyl acetate/petroleum ether (1:5) to give 11 g (89%) of tert-butyl (R)-3-(4-[bis[(4-methoxyphenyl)methyl]-amino]-2-oxo-1H,2H,3H-imidazo[4,5-c]pyridin-1-yl)piperidine-1-carboxylate as a yellow solid oil.

Step 5

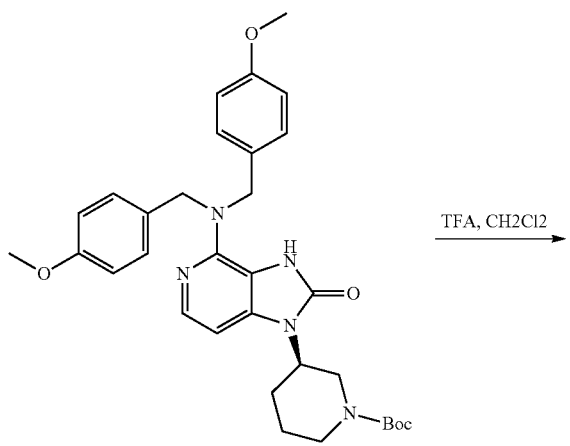

Into a 50-mL round-bottom flask was placed tert-butyl (R)-3-(4-[bis[(4-methoxyphenyl)-methyl]amino]-2-oxo-1H,2H,3H-imidazo[4,5-c]pyridin-1-yl)piperidine-1-carboxylate (1.5 g, 2.61 mmol, 1.00 equiv), dichloromethane (30 mL), and trifluoroacetic acid (30 mL). The resulting solution was stirred for 4 h at 50° C. The pH value of the solution was adjusted to 9 with sodium bicarbonate. The resulting solution was extracted with dichloromethane and the organic layers combined and dried over anhydrous sodium sulfate. The resulting mixture was concentrated under vacuum to give 0.45 g (73.7%) of (R)-4-amino-1-(piperidin-3-yl)-1,3-dihydro-2H-imidazo[4,5-c]pyridin-2-one as a light yellow solid.

Step 6

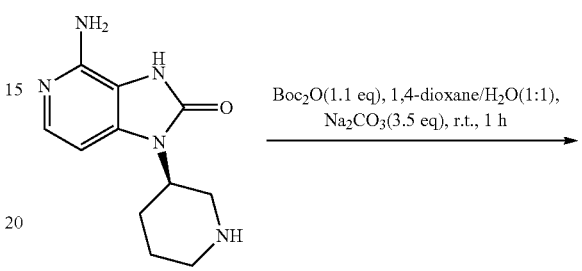

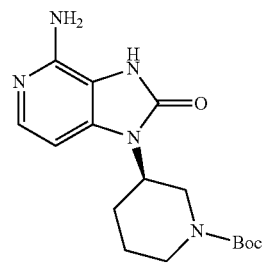

Into a 100-mL round-bottom flask was placed (R)-4-amino-1-(piperidin-3-yl)-1,3-dihydro-2H-imidazo[4,5-c]pyridin-2-one (1 g, 4.29 mmol, 1.00 equiv), 1,4-dioxane/H₂O (1:1, 50 mL), Boc₂O (1.03 g, 4.72 mmol, 1.03 equiv), and sodium carbonate (1.5 g, 14.15 mmol, 1.50 equiv). The resulting solution was stirred for 1 h at 25° C., then extracted with dichloromethane and the organic layers were combined. The resulting organic layer was washed with water and saturated sodium chloride and then concentrated under vacuum. The residue was applied onto a silica gel column and eluted with dichloromethane/methanol (30:1) to give 1.2 g (84%) of tert-butyl (R)-3-(4-amino-2-oxo-2,3-dihydro-1H-imidazo[4,5-c]pyridin-1-yl)piperidine-1-carboxylate as a light yellow solid.

Step 7

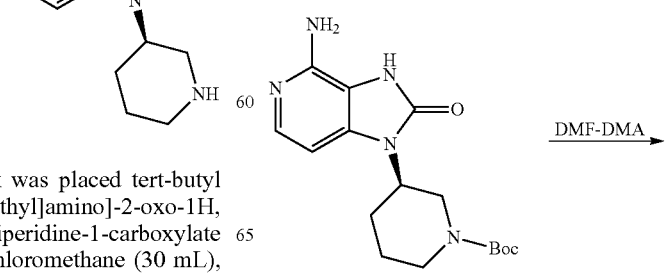

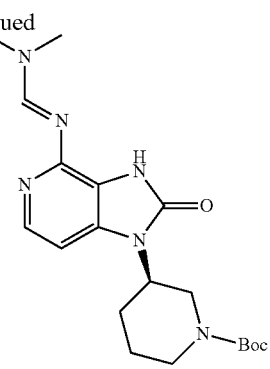

Into a 100-mL round-bottom flask was placed tert-butyl (R)-3-(4-amino-2-oxo-2,3-dihydro-1H-imidazo[4,5-c]pyridin-1-yl)piperidine-1-carboxylate (6.5 g, 19.50 mmol, 1.00 equiv) and DMF-DMA (50 mL). The resulting solution was stirred for 1 h at 40° C. and then concentrated under vacuum. The resulting mixture was then dissolved with CH₂Cl₂ and washed with brine. The organic layers combined and concentrated under vacuum, and washed with hexane. The solids were collected by filtration to give 5.0289 g (66%) of tert-butyl (R,E)-3-(4-((((dimethylamino)methylene)amino)-2-oxo-2,3-dihydro-1H-imidazo[4,5-c]pyridin-1-yl)piperidine-1-carboxylate as a solid.

LC-MS m/z: 389.2 (M+1)

Reference 2

Synthesis of 4-amino-3-(4-phenoxyphenyl)-1-[(3R)-piperidin-3-yl]-1H,2H,3H-imidazo[4,5-c]pyridin-2-one

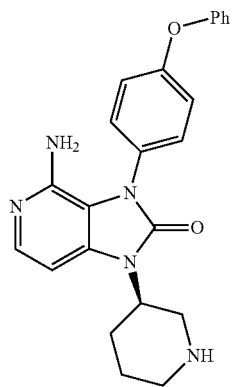 [SMILES: Nc1nccc2c1n(-c1ccc(Oc3ccccc3)cc1)c(=O)n2[C@@H]1CCCNC1]

Step 1

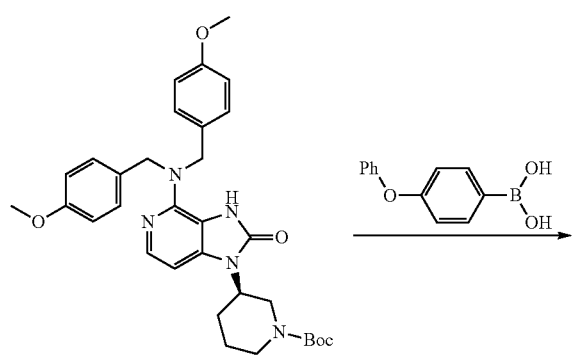

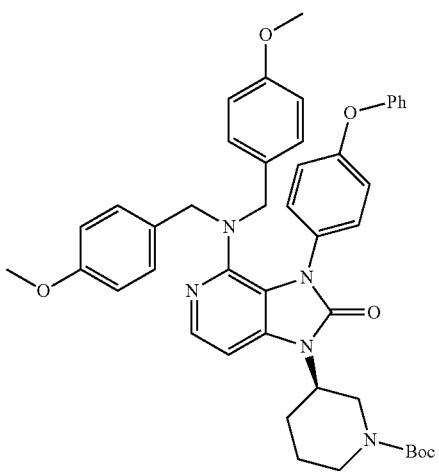

Into a 250-mL round-bottom flask, was placed tert-butyl (R)-3-(4-[bis[(4-methoxyphenyl)-methyl]amino]-2-oxo-1H, 2H,3H-imidazo[4,5-c]pyridin-1-yl)piperidine-1-carboxylate (10 g, 17.43 mmol, 1.00 equiv), dichloromethane (100 mL), (4-phenoxyphenyl)boronic acid (7.5 g, 35.04 mmol, 2.00 equiv), TEMPO (3 g, 19.20 mmol, 1.10 equiv), and TEA (7 g, 69.18 mmol, 4.00 equiv), Cu(OAc)₂ (1.6 g, 8.81 mmol, 0.50 equiv). The resulting solution was stirred overnight at 25° C. under ambient-pressure oxygen atmosphere. (4-Phenoxyphenyl)boronic acid (7.5 g, 35.04 mmol, 2.00 equiv) was added and the resulting solution was allowed to react overnight at 25° C. The residue was applied onto a silica gel column and eluted with ethyl acetate/petroleum ether (1:3) to give 1.5 g (12%) of tert-butyl (R)-3-(4-[bis[(4-methoxyphenyl)methyl]amino]-2-oxo-3-(4-phenoxyphenyl)-1H,2H, 3H-imidazo[4,5-c]pyridin-1-yl)piperidine-1-carboxylate as a yellow solid.

Step 6

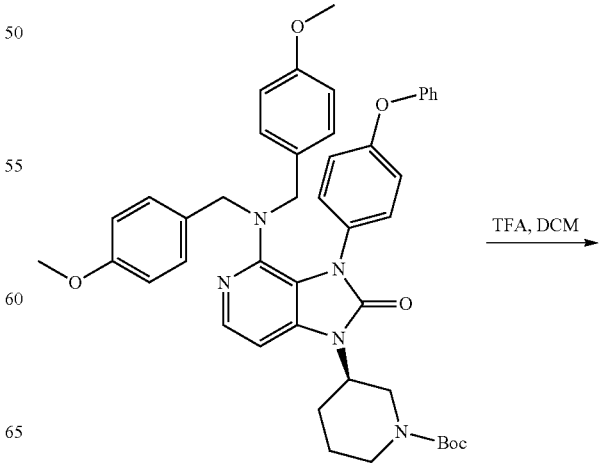

Step 1

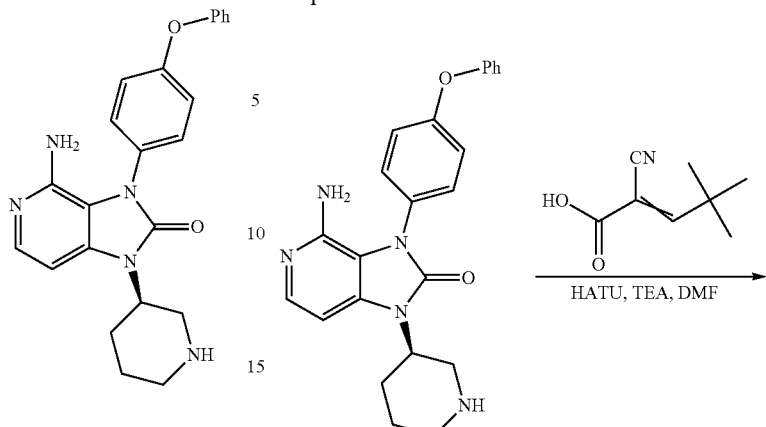

Into a 250-mL round-bottom flask, was placed tert-butyl (R)-3-(4-[bis[(4-methoxyphenyl)-methyl]amino]-2-oxo-3-(4-phenoxyphenyl)-1H,2H,3H-imidazo[4,5-c]pyridin-1-yl) piperidine-1-carboxylate (5 g, 6.07 mmol, 1.00 equiv, 90%), dichloromethane (80 mL), and trifluoroacetic acid (80 mL). The resulting solution was stirred for 5 h at 50° C. The resulting mixture was concentrated under vacuum. The pH value of the solution was adjusted to 9 with sodium bicarbonate. The resulting solution was extracted with of dichloromethane and the organic layers combined and dried over anhydrous sodium sulfate. The residue was applied onto a silica gel column and eluted with dichloromethane/methanol (30:1) to give 1 g (41%) of 4-amino-3-(4-phenoxyphenyl)-1-[(3R)-piperidin-3-yl]-1H,2H,3H-imidazo[4,5-c]pyridin-2-one as a light yellow solid.

Example 1

Synthesis of (R)-2-(3-(4-amino-2-oxo-3-(4-phenoxyphenyl)-2,3-dihydroimidazo[4,5-c]pyridin-1-yl)piperidine-1-carbonyl)-4,4-dimethylpent-2-enenitrile

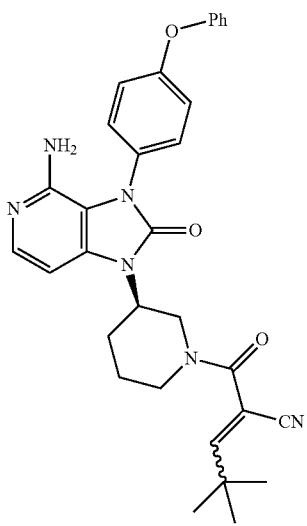 [SMILES: CC(C)(C)C=C(C#N)C(=O)N1CCC[C@@H](n2c(=O)n(-c3ccc(Oc4ccccc4)cc3)c3c(N)nccc32)C1]

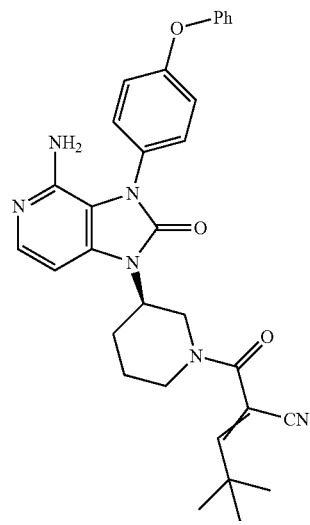

Into a 10-mL round-bottom flask was placed 4-amino-3-(4-phenoxyphenyl)-1-[(3R)-piperidin-3-yl]-1H,2H,3H-imidazo[4,5-c]pyridin-2-one (79 mg, 0.20 mmol, 1.00 equiv), N,N-dimethylformamide (2 mL), TEA (0.082 mL, 1.50 equiv), HATU (113 mg, 0.30 mmol, 1.50 equiv), and 2-cyano-4,4-dimethylpent-2-enoic acid (46 mg, 0.30 mmol, 3.00 equiv). The resulting solution was stirred for 2.5 h at room temperature and then quenched by the addition of water. The resulting solution was extracted with dichloromethane and the organic layers combined and concentrated under vacuum. The crude product was purified by Prep-HPLC with the following conditions (2#-AnalyseHPLC-SHIMADZU (HPLC-10)): Column, Gemini-NX C18 AXAI Packed, 21.2×150 mm 5 um 11 nm; mobile phase, WATER WITH 0.05% TFA and ACN (20.0% ACN up to 50.0% in 8 min); Detector, 254 nm to give 50 mg (47%) of the title compound as a white solid. LC-MS m/z: 537.2 (M+1)

Example 2

Synthesis of (R)-2-(3-(4-amino-2-oxo-3-(4-phenoxyphenyl)-2,3-dihydroimidazo[4,5-c]pyridin-1-yl)piperidine-1-carbonyl)-4-methyl-4-(4-(oxetan-3-yl)piperazin-1-yl)pent-2-enenitrile

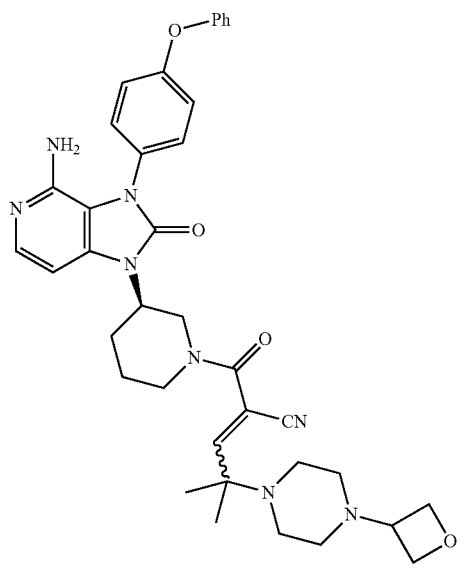 [SMILES: CC(C)(C=C(C#N)C(=O)N1CCC[C@@H](n2c(=O)n(-c3ccc(Oc4ccccc4)cc3)c3c(N)nccc32)C1)N1CCN(C2COC2)CC1]

Step 1

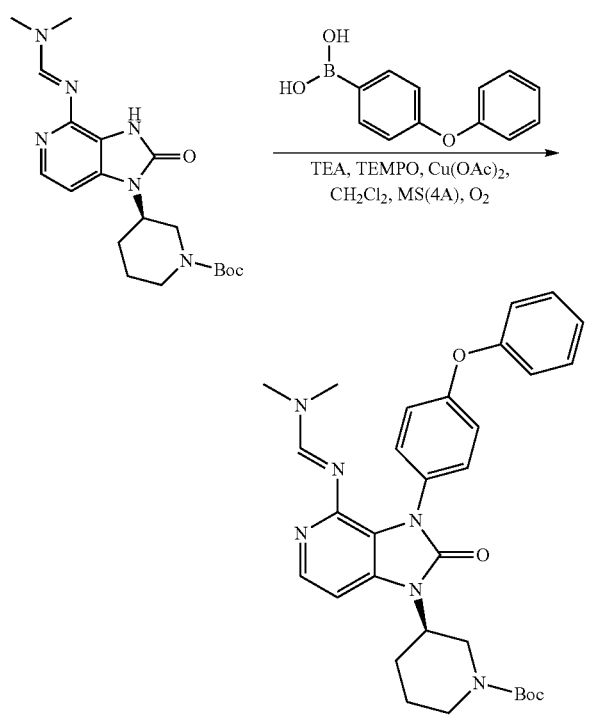

Into a 50-mL round-bottom flask, was placed tert-butyl (R,E)-3-(4-(((dimethylamino)-methylene)amino)-2-oxo-2,3-dihydro-1H-imidazo[4,5-c]pyridin-1-yl)piperidine-1-carboxylate (200 mg, 0.51 mmol, 1.00 equiv), dichloromethane (20 mL), TEA (208 mg, 2.06 mmol, 4.00 equiv), TEMPO (88.5 mg, 0.57 mmol, 1.10 equiv), and Cu(OAc)$_2$ (46.7 mg, 0.26 mmol, 0.50 equiv). The resulting solution was stirred for 0.5 h at 25° C. (4-Phenoxyphenyl)boronic acid (220 mg, 1.03 mmol, 2.00 equiv) was added and the resulting solution was allowed to react overnight at 25° C. The residue was applied onto a silica gel column and eluted with dichloromethane/ethyl acetate (5:1) to give 150 mg (52%) of tert-butyl (R)-3-[4-[(E)-[(dimethylamino)methylidene]amino]-2-oxo-3-(4-phenoxyphenyl)-1H,2H,3H-imidazo[4,5-c]pyridin-1-yl]piperidine-1-carboxylate as a light yellow solid.

Step 2

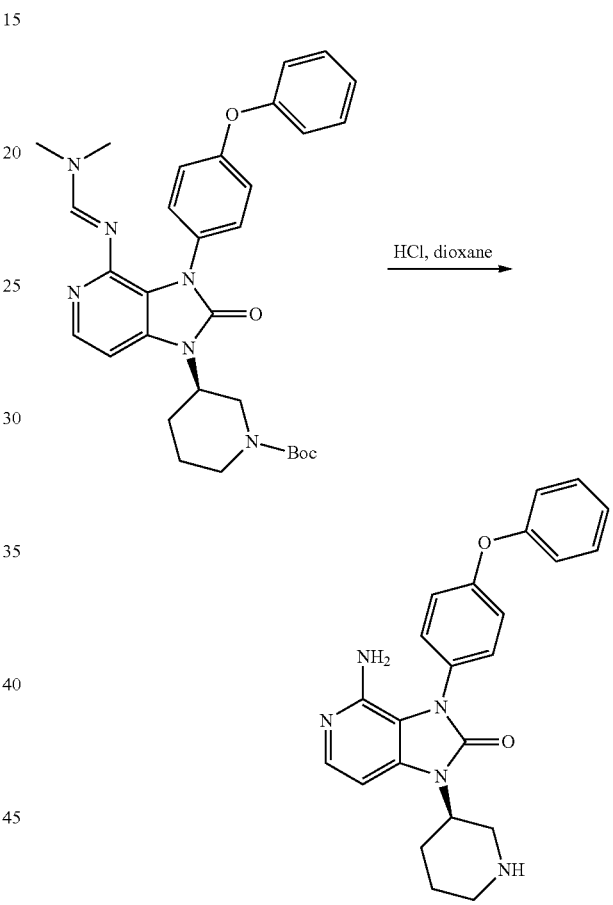

Into a 25-mL round-bottom flask was placed tert-butyl (3R)-3-[4-[(E)-[(dimethylamino)-methylidene]-amino]-2-oxo-3-(4-phenoxyphenyl)-1H,2H,3H-imidazo[4,5-c]pyridin-1-yl]piperidine-1-carboxylate (150 mg, 0.27 mmol, 1.00 equiv), 1,4-dioxane (6 mL), and hydrogen chloride (3 mL). The resulting solution was stirred overnight at 50° C. The reaction mixture was quenched with water. The pH of the solution was adjusted to 9 with sodium bicarbonate. The resulting solution was extracted with dichloromethane:CH$_3$OH=10:1 and the organic layers were combined. The resulting mixture was washed with sodium chloride and the organic layers were combined, dried over anhydrous sodium sulfate and concentrated under vacuum. The residue was applied onto a silica gel column and eluted with dichloromethane/methanol (30:1) to give 80 mg (74%) of 4-amino-3-(4-phenoxyphenyl)-1-[(3R)-piperidin-3-yl]-1H,2H,3H-imidazo[4,5-c]pyridin-2-one as a light yellow solid.

Step 3

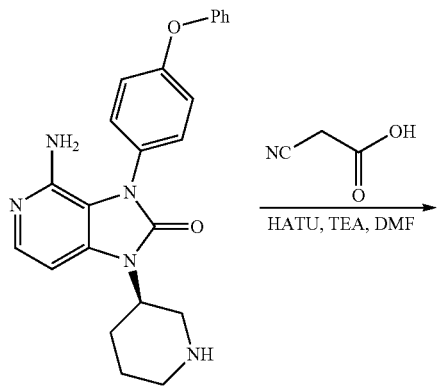

Step 4

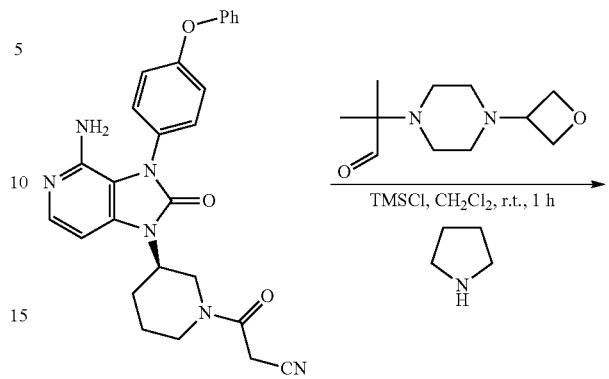

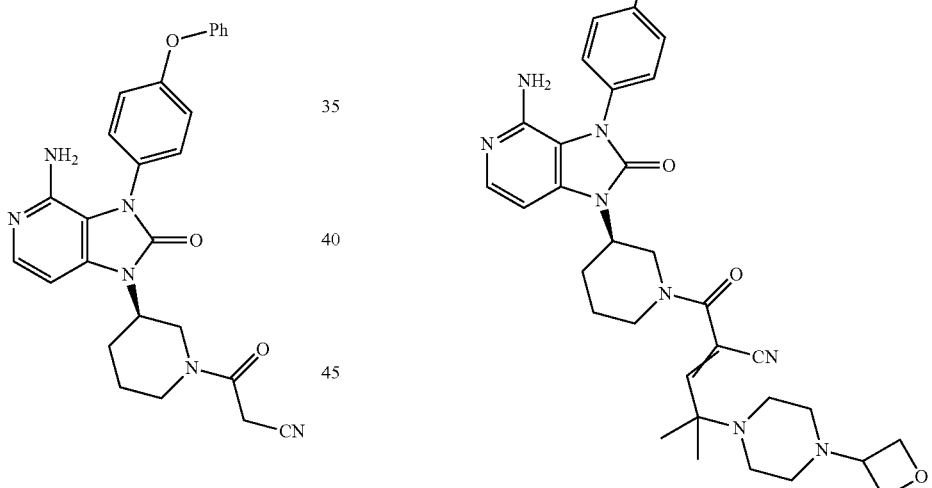

Into a 50-mL round-bottom flask was placed 4-amino-3-(4-phenoxyphenyl)-1-[(3R)-piperidin-3-yl]-1H,2H,3H-imidazo[4,5-c]pyridin-2-one (2 g, 4.98 mmol, 1.00 equiv), N,N-dimethylformamide (20 mL), 2-cyanoacetic acid (402.5 mg, 4.73 mmol, 0.95 equiv), HATU (2.84 g, 7.47 mmol, 1.50 equiv), and TEA (1.51 g, 14.92 mmol, 3.00 equiv). The resulting solution was stirred for 1 h at room temperature and then quenched with water. The resulting solution was extracted with ethyl acetate and the organic layers combined. The organic layer was washed with saturated sodium chloride, dried over anhydrous sodium sulfate and concentrated under vacuum. The residue was applied onto a silica gel column with dichloromethane/methanol (30:1) to give 1.3 g (56%) of 3-[(3R)-3-[4-amino-2-oxo-3-(4-phenoxyphenyl)-1H,2H,3H-imidazo[4,5-c]pyridin-1-yl]piperidin-1-yl]-3-oxopropanenitrile as a light yellow solid.

Into a 50-mL round-bottom flask was placed 3-[(3R)-3-[4-amino-2-oxo-3-(4-phenoxyphenyl)-1H,2H,3H-imidazo[4,5-c]pyridin-1-yl]piperidin-1-yl]-3-oxopropanenitrile (800 mg, 1.71 mmol, 1.00 equiv), dichloromethane (20 mL), 2-methyl-2-[4-(oxetan-3-yl)piperazin-1-yl]propanal (1.0875 g, 5.12 mmol, 3.00 equiv), TMSCl (922 mg, 8.49 mmol, 4.97 equiv), and pyrrolidine (0.607 g). The resulting solution was stirred for 1 h at room temperature. The resulting mixture was concentrated under vacuum. The crude product was purified by Prep-TLC, then purified by Prep-HPLC under the following conditions (2#-AnalyseHPLC-SHI-MADZU (HPLC-10)): Column, Gemini-NX C18 AXAI Packed, 21.2×150 mm 5 um 11 nm; mobile phase, water with 0.05% TFA and ACN (20.0% ACN up to 40.0% in 10 min); Detector, uv 254 nm) to give 0.478 g (42%) of the title compound as a light yellow solid. LC-MS m/z: 663.3 (M+1).

Example 3

Synthesis of (R)-1-(1-acryloylpiperidin-3-yl)-4-amino-3-(4-phenoxyphenyl)-1H-imidazo[4,5-c]pyridin-2(3H)-one

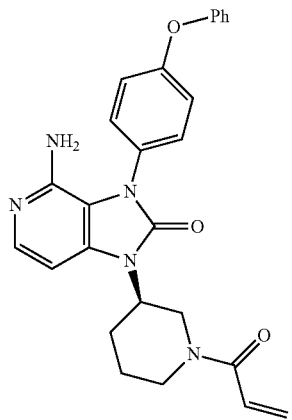 [SMILES: C=CC(=O)N1CCC[C@@H](n2c(=O)n(-c3ccc(Oc4ccccc4)cc3)c3c(N)nccc32)C1]

Into a 100-mL round-bottom flask, was placed (R)-4-amino-3-(4-phenoxyphenyl)-1-(piperidin-3-yl)-1H-imidazo[4,5-c]pyridin-2(3H)-one (150 mg, 0.37 mmol, 1.00 equiv), DCM-CH3OH (6 mL), TEA (113 mg, 1.12 mmol, 3.00 equiv). This was followed by the addition of prop-2-enoyl chloride (40.1 mg, 0.44 mmol, 1.20 equiv) dropwise with stirring at 0° C. in 5 min. The resulting solution was stirred for 2 h at 0° C. The resulting mixture was concentrated under vacuum. The residue was applied onto a silica gel column with dichloromethane/methanol (30:1). The crude product (100 mg) was purified by Prep-HPLC with the following conditions (Column, XBridge Prep C18 OBD Column, 5 um, 19*150 mm; mobile phase, water with 0.05% TFA and ACN (25.0% ACN up to 45.0% in 8 min). 54.5 mg product of (R)-1-(1-acryloylpiperidin-3-yl)-4-amino-3-(4-phenoxyphenyl)-1H-imidazo[4,5-c]pyridin-2(3H)-one was obtained as a white solid. LC-MS m/z: 465.2 (M+1)

Example 4

Synthesis of (R)-4-amino-1-(1-(but-2-ynoyl)piperidin-3-yl)-3-(4-phenoxyphenyl)-1H-imidazo[4,5-c]pyridin-2(3H)-one

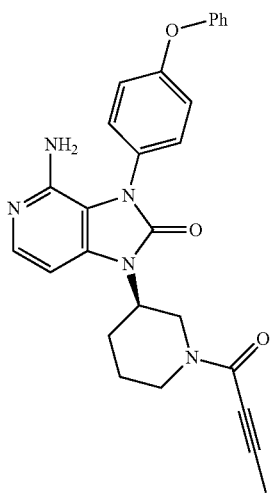 [SMILES: CC#CC(=O)N1CCC[C@@H](n2c(=O)n(-c3ccc(Oc4ccccc4)cc3)c3c(N)nccc32)C1]

Into a 100-mL round-bottom flask, was placed (R)-4-amino-3-(4-phenoxyphenyl)-1-(piperidin-3-yl)-1H-imidazo[4,5-c]pyridin-2(3H)-one (150 mg, 0.37 mmol, 1.00 equiv), N,N-dimethylformamide (15 mL), but-2-ynoic acid (31.42 mg, 0.37 mmol, 1.00 equiv), HATU (213.2 mg, 0.56 mmol, 1.50 equiv), TEA (113.4 mg, 1.12 mmol, 3.00 equiv). The resulting solution was stirred for 2 h at room temperature. The reaction was then quenched by the addition of 50 mL of water. The resulting solution was extracted with 3×50 mL of dichloromethane and the organic layers combined. The resulting mixture was washed with 50 mL of brine. The mixture was dried over anhydrous sodium sulfate and concentrated under vacuum. The residue was applied onto a silica gel column with dichloromethane/methanol (30:1). The crude product (100 mg) was purified by Prep-HPLC as described in ex 3 to obtain 86.5 mg (50%) of (R)-4-amino-1-(1-(but-2-ynoyl)piperidin-3-yl)-3-(4-phenoxyphenyl)-1H-imidazo[4,5-c]pyridin-2(3H)-one as a white solid. LC-MS m/z: 468.2 (M+1).

Example 5

Synthesis of (R)-2-(3-(4-amino-2-oxo-3-(4-phenoxyphenyl)-2,3-dihydro-1H-imidazo[4,5-c]pyridin-1-yl)piperidine-1-carbonyl)-4-methyl-4-(1-methylpiperidin-4-yl)pent-2-enenitrile

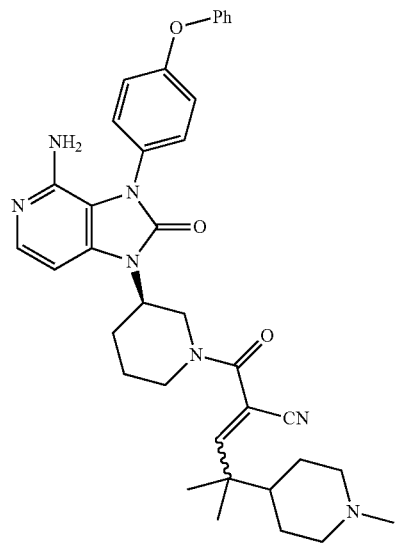 [SMILES: CN1CCC(C(C)(C)C=C(C#N)C(=O)N2CCC[C@@H](n3c(=O)n(-c4ccc(Oc5ccccc5)cc4)c4c(N)nccc43)C2)CC1]

Step 1

Into a 250-mL 3-necked round-bottom flask, was placed methyl 2-(piperidin-4-yl)acetate hydrochloride (10 g, 51.63 mmol, 1.00 equiv), dichloromethane (100 mL), The resulting solution was stirred for 30 min at 0° C. Next was added triethylamine (15.65 g, 154.66 mmol, 3 equiv), Boc$_2$O (12.4 g, 56.82 mmol, 1.1 equiv). The resulting solution was allowed to react, with stirring, for an additional 14 h at 25° C. The pH value of the solution was adjusted to 7.0 with citric acid (3%). The resulting mixture was washed with 2×100 mL of water and 2×100 mL of saturated salt water. The residue was applied onto a silica gel column with ethyl acetate/petroleum ether (1:10). This resulted in 10 g (75.2%) of tert-butyl 4-(2-methoxy-2-oxoethyl)piperidine-1-carboxylate as colorless oil.

Step 2

Into a 250-mL 3-necked round-bottom flask, was placed LDA (46.7 mL, 3.00 equiv), tetrahydrofuran (80 mL), tert-butyl 4-(2-methoxy-2-oxoethyl)piperidine-1-carboxylate (8 g, 31.1 mmol, 1.00 equiv), The resulting solution was stirred for 30 min at −78° C. Then CH₃I (22 g, 155 mmol, 5.00 equiv) was added. The resulting solution was allowed to react, with stirring, for an additional 1 h at −78° C. Additional LDA (46.7 mL, 3.00 equiv) was added at −78° C. and after 0.5 h, CH₃I (22 g, 155 mmol, 5.00 equiv) was added. The reaction was stirred 16 h at r.t. The reaction was then quenched by the addition of 200 mL of NH4Cl. The resulting solution was extracted with 2×200 mL of ethyl acetate and the organic layers combined. The resulting mixture was washed with 2×200 mL of water and 2×200 mL of saturated sodium chloride. The residue was purified by silica gel chromatography using ethyl acetate/petroleum ether (1:35). This resulted in 6 g (68%) of tert-butyl 4-(1-methoxy-2-methyl-1-oxopropan-2-yl)piperidine-1-carboxylate as light yellow oil.

Step 3

Into a 100-mL 3-necked round-bottom flask, was placed LiAlH4 (1.6 g, 42.2 mmol, 4.00 equiv), tetrahydrofuran (50 mL), tert-butyl 4-(1-methoxy-2-methyl-1-oxopropan-2-yl) piperidine-1-carboxylate (3 g, 10.5 mmol, 1.00 equiv). The resulting solution was stirred for 3 h at −78° C. The reaction mixture was warmed to 0° C. The reaction was then quenched by the addition of 1.6 mL of water, then 1.6 mL of 15% NaOH was added followed by 4.8 mL H2O. The solids were filtered to afford in 1.5 g (83%) of 2-methyl-2-(1-methylpiperidin-4-yl)propan-1-ol as a pink oil.

Step 4

Into a 100-mL round-bottom flask, was placed oxalic dichloride (440 mg, 3.47 mmol, 1.20 equiv), dichloromethane (50 mL), At −78° C. put in DMSO (684 mg, 8.75 mmol, 3.00 equiv), 2-methyl-2-(1-methylpiperidin-4-yl)propan-1-ol (500 mg, 2.92 mmol, 1.00 equiv), TEA (1.48 g, 14.6 mmol, 5.00 equiv). The resulting solution was stirred for 30 min at −78° C. The resulting solution was allowed to react, with stirring, for an additional 2 h at 25° C. The reaction was then quenched by the addition of water. The resulting solution was extracted with of dichloromethane and the organic layers combined and dried over anhydrous sodium sulfate and concentrated under vacuum. This resulted in 385 mg (88%) of 2-methyl-2-(1-methylpiperidin-4-yl)propanal as yellow oil.

Step 5

Into a 100-mL round-bottom flask, was placed (R)-3(3-(3-(4-amino-2-oxo-3-(4-phenoxyphenyl)-2,3-dihydro-1H-imidazo[4,5-c]pyridin-1-yl)piperidin-1-yl)-3-oxopropanenitrile (100 mg, 0.19 mmol, 1.00 equiv, 90%), dichloromethane (50 mL), 2-methyl-2-(1-methylpiperidin-4-yl)propanal (108 mg, 0.57 mmol, 3.00 equiv), TMSCl (115 mg, 1.01 mmol, 5.00 equiv, 95%), pyrrolidine (75.8 mg, 1.01 mmol, 5.00 equiv, 95%). The resulting solution was stirred for 16 h at rt. The crude product was purified by Prep-HPLC with the following conditions (Column, Gemini-NX C18 AXAI Packed, 21.2×150 mm 5 um 11 nm; mobile phase, WATER WITH 0.05% TFA and ACN (20.0% ACN up to 50.0% in 8 min); Detector, 254 nm. This resulted in 15.5 mg (12%) of (R)-2-(3-(4-amino-2-oxo-3-(4-phenoxyphenyl)-2,3-dihydro-1H-imidazo[4,5-c]pyridin-1-yl) piperidine-1-carbonyl)-4-methyl-4-(1-methylpiperidin-4-yl) pent-2-enenitrile as a light yellow solid. LC-MS m/z: 620.3 (M+1).

Example 6

Synthesis of (R)-2-(3-(4-amino-2-oxo-3-(4-phenoxyphenyl)-2,3-dihydro-1H-imidazo[4,5-c]pyridin-1-yl)piperidine-1-carbonyl)-6-hydroxy-4-(2-hydroxyethyl)hex-2-enenitrile

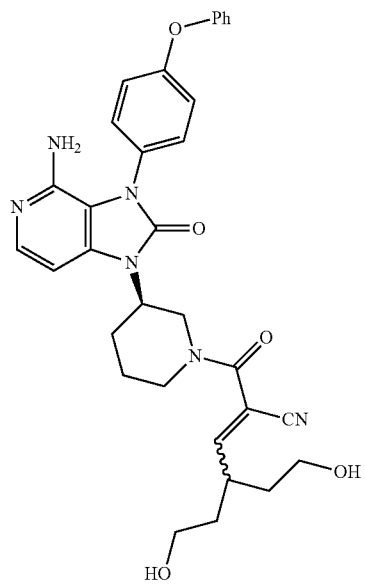 [SMILES: N#CC(=CC(CCO)CCO)C(=O)N1CCC[C@@H](n2c(=O)n(-c3ccc(Oc4ccccc4)cc3)c3c(N)nccc32)C1]

Step 1

Into a 250-mL 3-necked round-bottom flask purged and maintained with an inert atmosphere of nitrogen, HMPA (6.0 mL) and LDA (16.8 mmol) in dry THF (20 mL) at −78° C. was treated with acetonitrile (690 mg, 16.8 mmol). The solution was stirred for 30 min, and (2-bromoethoxy)(tert-butyl)dimethylsilane (3.4 g, 14.3 mmol) in THF (15 mL) was added dropwise. Stirring was continued for 2 h, after which a second portion of LDA (16.8 mmol in 20 mL THF) was added. The solution was stirred for 30 min, and (2-bromoethoxy)(tert-butyl)dimethylsilane (3.4, 14.3 mmol) in THF (15 mL) was added dropwise. The reaction was allowed to proceed for 2 h. Saturated aqueous NH4Cl was added, and the mixture was allowed to reach room temperature. Diethyl ether was added, the phases were separated, and the aqueous layer was extracted with diethyl ether. The combined organic phases were washed with brine, dried over Na2SO4, and concentrated. Column chromatography [silica, petroleum ether] afforded a colorless oil (3.2 g, 53%).

Step 2

Into a 250-mL 3-necked round-bottom flask purged and maintained with an inert atmosphere of nitrogen, was placed 4-[(tert-butyldimethylsilyl)oxy]-2-[2-[(tert-butyldimethylsilyl)oxy]ethyl]butanenitrile (1 g, 2.80 mmol, 1.00 equiv) in toluene (15 mL). DIBAL-H (1M) (3.36 mL, 1.20 equiv) was added at −78° C. and the resulting solution was stirred for 1 h at −78° C. in a liquid nitrogen bath. Water (0.7 mL) was added and the mixture was allowed to reach RT. Aqueous NaOH (0.7 mL, 4M) was added and stirring was continued for 15 min. Water (2.1 mL) was added and the suspension was stirred for a further 15 min. The mixture was dried over with Na2SO4 and concentrated under vacuum. The residue was purified by silica gel column with PE/EA (20:1). This resulted in 900 mg (89%) of 4-[(tert-butyldimethylsilyl) oxy]-2-[2-[(tert-butyldimethylsilyl)oxy]ethyl]butanal as colorless oil.

Step 3

Into a 8-mL vial, was placed 3-[(3R)-3-[4-amino-2-oxo-3-(4-phenoxyphenyl)-1H,2H,3H-imidazo[4,5-c]pyridin-1-yl]piperidin-1-yl]-3-oxopropanenitrile (150 mg, 0.32 mmol, 1.00 equiv), 4-[(tert-butyldimethylsilyl)oxy]-2-2-[(tert-butyldimethylsilyl)oxy]ethylbutanal (346 mg, 0.96 mmol, 3.00 equiv), TMSCl (173 mg, 1.59 mmol, 5.00 equiv), pyrrolidine (114 mg, 1.61 mmol, 5.00 equiv), dichloromethane (2 mL). The resulting solution was stirred for 3 h at rt. The resulting mixture was concentrated under vacuum. The residue was applied onto a silica gel column with dichloromethane/methanol (30:1). This resulted in 120 mg (46%) of 2-[[(3R)-3-[4-amino-2-oxo-3-(4-phenoxyphenyl)-1H,2H,3H-imidazo[4,5-c]pyridin-1-yl]piperidin-1-yl]carbonyl]-6-[(tert-butyldimethylsilyl)oxy]-4-[2-[(tert-butyldimethylsilyl)oxy]ethyl]hex-2-enenitrile as a yellow solid.

Step 4

Into a 25-mL round-bottom flask, was placed 2-[[(3R)-3-[4-amino-2-oxo-3-(4-phenoxyphenyl)-1H,2H,3H-imidazo[4,5-c]pyridin-1-yl]piperidin-1-yl]carbonyl]-6-[(tert-butyldimethylsilyl)oxy]-4-[2-[(tert-butyldimethylsilyl)oxy]ethyl]hex-2-enenitrile (120 mg, 0.15 mmol, 1.00 equiv), trifluoroacetic acid (I mL), dichloromethane (5 mL). The resulting solution was stirred for 2 h at rt. The reaction was then quenched by the addition of saturated sodium bicarbonate. The resulting solution was extracted with 3×20 mL of DCM/MeOH (10:1) and the organic layers combined. The resulting mixture was washed with saturated sodium chloride. The mixture was dried over anhydrous sodium sulfate and concentrated under vacuum. The residue was purified by Prep-TLC with DCM/MeOH (15:1). The crude product was purified by Prep-HPLC with the following conditions (Atlantis Prep T3 OBD Column, 19*150 mm 5 um 10 nm; mobile phase, Water with 0.1% FA and MeCN (20.0% MeCN up to 50.0% in 10 min); Detector, 254 nm. This resulted in 7.9 mg (9%) of (R)-2-(3-(4-amino-2-oxo-3-(4-phenoxyphenyl)-2,3-dihydro-1H-imidazo[4,5-c]pyridin-1-yl)piperidine-1-carbonyl)-6-hydroxy-4-(2-hydroxyethyl)hex-2-enenitrile as a white solid. LC-MS m/z: 583.2 (M+1).

Example 7

Synthesis of (R)-2-(3-(4-amino-3-(4-(2,6-difluorophenoxy)phenyl)-2-oxo-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile

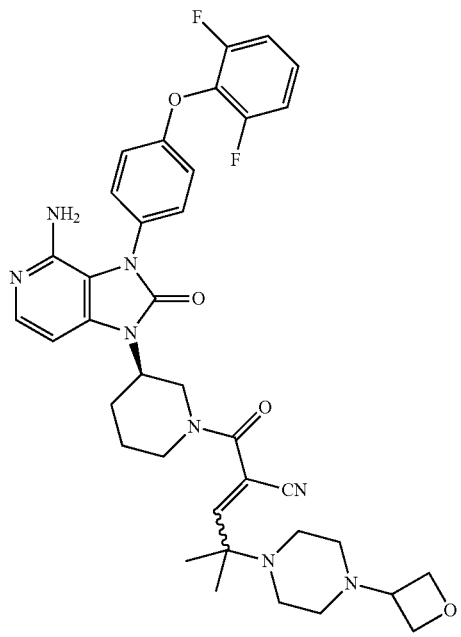 [SMILES: CC(C)(C=C(C#N)C(=O)N1CCC[C@@H](n2c(=O)n(-c3ccc(Oc4c(F)cccc4F)cc3)c3c(N)nccc32)C1)N1CCN(C2COC2)CC1]

Step 1

Into a 250-mL round-bottom flask purged and maintained with an atmosphere of O2, was placed Cu(OAc)2 (6.96 g, 38.3 mmol, 1.00 equiv), pyridine (15.2 g, 192 mmol, 5.00 equiv) and 4 A mol. sieves (5 g) in dichloromethane (100 mL). The resulting solution was stirred for 30 min and then 2,6-difluorophenol (5 g, 38.4 mmol, 1.00 equiv) and (4-bromophenyl)boronic acid (15.4 g, 76.6 mmol, 2.00 equiv) were added. The resulting solution was stirred overnight at rt. The resulting mixture was concentrated under vacuum. The residue was applied onto a silica gel column and eluted with petroleum ether. This resulted in 5.5 g (50%) of 2-(4-bromophenoxy)-1,3-difluorobenzene as yellow oil.

Step 2

Into a 250-mL 3-necked round-bottom flask purged and maintained with an inert atmosphere of nitrogen, was placed 2-(4-bromophenoxy)-1,3-difluorobenzene (5.5 g, 19.3 mmol, 1.00 equiv) in tetrahydrofuran (100 mL). A 2.5 M solution of nBuLi in hexane (11.6 mL, 1.50 equiv) was added at −78° C. and the resulting solution was stirred for 30 min and then trimethyl borate (4.03 g, 38.8 mmol, 2.00 equiv) was added. The reaction was allowed to be warmed to RT and the resulting solution was stirred for 3 h at rt. The reaction was then quenched by the addition of hydrogen chloride (2M). The resulting solution was extracted with 3×150 mL of ether and the organic layers combined. The resulting mixture was washed with 1×200 mL of sodium chloride (saturated). The mixture was dried over anhydrous sodium sulfate and concentrated under vacuum. The residue was applied onto a silica gel column with dichloromethane/methanol (50:1). This resulted in 2.15 g (45%) of [4-(2,6-difluorophenoxy)phenyl]boronic acid as a brown solid.

Step 3

Into a 100-mL round-bottom flask purged and maintained with an atmosphere of O2, was placed (R,E)-tert-butyl 3-(4-(((dimethylamino)methylene)amino)-2-oxo-2,3-dihydro-1H-imidazo[4,5-c]pyridin-1-yl)piperidine-1-carboxylate (500 mg, 1.29 mmol, 1.00 equiv), TEA (521 mg, 5.15 mmol, 4.00 equiv), Cu(OAc)2 (117 mg, 0.64 mmol, 0.50 equiv), TEMPO (221 mg, 1.41 mmol, 1.10 equiv) and Ms (4A) (500 mg) in dichloromethane (50 mL). The resulting solution was stirred for 30 min and then [4-(2,6-difluorophenoxy)phenyl]boronic acid (644 mg, 2.58 mmol, 2.00 equiv) was added. The resulting solution was stirred overnight at room temperature. The resulting mixture was concentrated under vacuum. The residue was applied onto a silica gel column with dichloromethane/methanol (30:1). This resulted in 490 mg of (R,E)-tert-butyl 3-(4-(((dimethylamino)methylene)amino)-2-oxo-3-(4-phenoxyphenyl)-2,3-dihydro-1H-imidazo[4,5-c]pyridin-1-yl)piperidine-1-carboxylate as a brown solid.

Step 4

To a solution of (R,E)-tert-butyl 3-(4-(((dimethylamino)methylene)amino)-2-oxo-3-(4-phenoxyphenyl)-2,3-dihydro-1H-imidazo[4,5-c]pyridin-1-yl)piperidine-1-carboxylate (490 mg, 0.83 mmol, 1.00 equiv) in 30 mL dioxane was added 15 mL of hydrogen chloride (12M). The resulting solution was stirred for 3 h at 85° C. in an oil bath. The reaction was then quenched by the addition of sodium bicarbonate(sat.). The resulting solution was extracted with 3×100 mL of DCM/MeOH (10:1) and the organic layers combined. The resulting mixture was washed with 1×100 mL of sodium chloride(sat.). The mixture was dried over anhydrous sodium sulfate and concentrated under vacuum. This resulted in 360 mg (100%) of 4-amino-3-[4-(2,6-difluorophenoxy)phenyl]-1-[(3R)-piperidin-3-yl]-1H,2H,3H-imidazo[4,5-c]pyridin-2-one as a brown solid.

Step 5

Into a 50-mL round-bottom flask, was placed 4-amino-3-[4-(2,6-difluorophenoxy)phenyl]-1-[(3R)-piperidin-3-yl]-1H,2H,3H-imidazo[4,5-c]pyridin-2-one (360 mg, 0.82 mmol, 1.00 equiv), 2-cyanoacetic acid (70 mg, 0.82 mmol, 1.00 equiv), HATU (470 mg, 1.24 mmol, 1.50 equiv), TEA (250 mg, 2.47 mmol, 3.00 equiv), N,N-dimethylformamide (10 mL). The resulting solution was stirred for 2 h at rt. The resulting solution was extracted with dichloromethane and the organic layers combined. The resulting mixture was washed with 6×100 mL of water. The mixture was dried over anhydrous sodium sulfate and concentrated under vacuum. The residue was applied onto a silica gel column with dichloromethane/methanol (30:1). This resulted in 260 mg (63%) of (R)-3-(3-(4-amino-3-(4-(2,6-difluorophenoxy)phenyl)-2-oxo-2,3-dihydro-1H-imidazo[4,5-c]pyridin-1-yl)piperidin-1-yl)-3-oxopropanenitrile as a brown solid.

Following the protocol in step 4 of example 2 afforded (R)-2-(3-(4-amino-3-(4-(2,6-difluorophenoxy)phenyl)-2-oxo-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile. LC-MS m/z: 699.2 (M+1)

Example 8

Synthesis of (R)-2-(3-(4-amino-3-(4-(2,3-difluorophenoxy)phenyl)-2-oxo-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile Step 1

Into a 250-mL round-bottom flask purged and maintained with an atmosphere of O2, was placed Cu(OAc)2 (6.96 g, 38.3 mmol, 1.00 equiv), pyridine (15.2 g, 192 mmol, 5.00 equiv) and 4 A mol. sieves (5 g) in dichloromethane (100 mL). The resulting solution was stirred for 30 min and then 2,3-difluorophenol (5 g, 38.43 mmol, 1.00 equiv) and (4-bromophenyl)boronic acid (15.4 g, 76.6 mmol, 2.00 equiv) were added. The resulting solution was stirred overnight at rt. The resulting mixture was concentrated under vacuum. The residue was applied onto a silica gel column with petroleum ether. This resulted in 3.17 g (29%) of 1-(4-bromophenoxy)-2,3-difluorobenzene as colorless oil.

Step 2

Into a 250-mL 3-necked round-bottom flask purged and maintained with an inert atmosphere of nitrogen, was placed 1-(4-bromophenoxy)-2,3-difluorobenzene (3.17 g, 11.12 mmol, 1.00 equiv) in tetrahydrofuran (100 mL). A 2.5 M solution of nBuLi (6.7 mL, 1.50 equiv) was added at −78° C. and the resulting solution was stirred for 30 min and then trimethyl borate (2.32 g, 22.3 mmol, 2.00 equiv) was added. The resulting solution was stirred for 3 h at rt. The reaction was then quenched by the addition of HCl (2M). The resulting solution was extracted with 3×150 mL of ether and the organic layers combined. The resulting mixture was washed with 1×200 mL of sodium chloride (sat'd.). The mixture was dried over anhydrous sodium sulfate and concentrated under vacuum. The residue was applied onto a silica gel column with dichloromethane/methanol (50:1). This resulted in 1 g (36%) of [4-(2,3-difluorophenoxy)phenyl]boronic acid as a white solid.

Following the protocols described in Example 2 but using [4-(2,3-difluorophenoxy)phenyl]boronic acid afforded title compound. LC-MS m/z: 699.2 (M+1).

Example 9

Synthesis of (R)-2-(3-(4-amino-3-(3-fluoro-4-phenoxyphenyl)-2-oxo-2,3-dihydro-1H-imidazo[4,5-c]pyridin-1-yl)piperidine-1-carbonyl)-4-methyl-4-(4-(oxetan-3-yl)piperazin-1-yl)pent-2-enenitrile

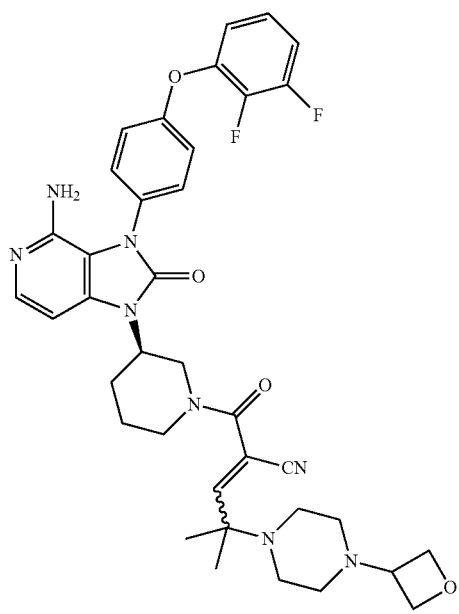 [SMILES: CC(C)(C=C(C#N)C(=O)N1CCC[C@@H](n2c(=O)n(-c3ccc(Oc4cccc(F)c4F)cc3)c3c(N)nccc32)C1)N1CCN(C2COC2)CC1]

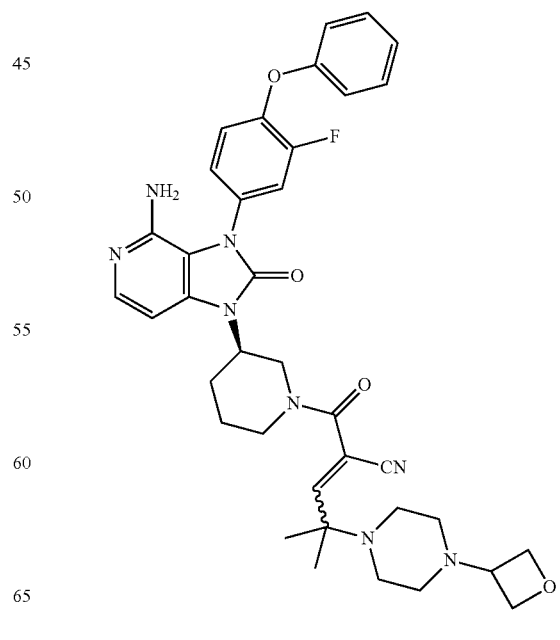

Following the protocols described in example 7 but using (3-fluoro-4-phenoxyphenyl)boronic acid afforded (the title compound using the methods described in Example 2. LC-MS m/z: 681.4 (M+1).

Example 10

Synthesis of (R)-2-(3-(4-amino-3-(2-fluoro-1-phenoxyphenyl)-2-oxo-2,3-dihydro-H-imidazo[4,5-c]pyridin-1-yl)piperidine-carbonyl)-4-methyl-4-(4-(oxetan-3-yl)piperazin-1-yl)pent-2-enenitrile

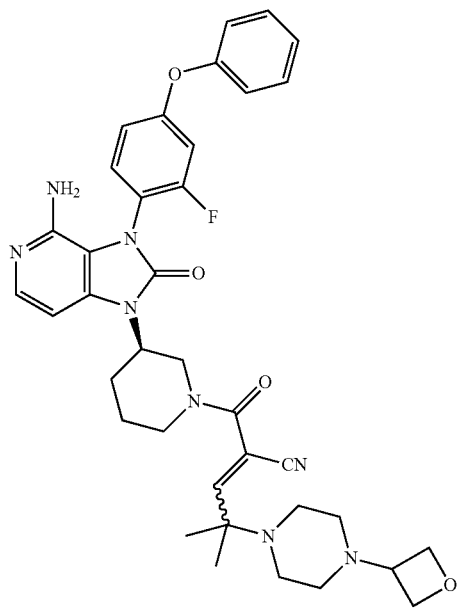 [SMILES: CC(C)(C=C(C#N)C(=O)N1CCC[C@@H](n2c(=O)n(-c3ccc(Oc4ccccc4)cc3F)c3c(N)nccc32)C1)N1CCN(C2COC2)CC1]

Following the protocols described in Example 7 but using (2-fluoro-4-phenoxyphenyl)boronic acid (prepared as described in PCT Int. Appl., 2012158764, 22 Nov. 201 afforded the title compound. LC-MS m/z: 681.2 (M+1).

Example 11

Synthesis of (S)-2-(2-((4-amino-2-oxo-3-(4-phenoxyphenyl)-2,3-dihydro-1H-imidazo[4,5-c]pyridin-1-yl)methyl)pyrrolidine-1-carbonyl)-4-methyl-4-(4-(oxetan-3-yl)piperazin-1-yl)pent-2-enenitrile

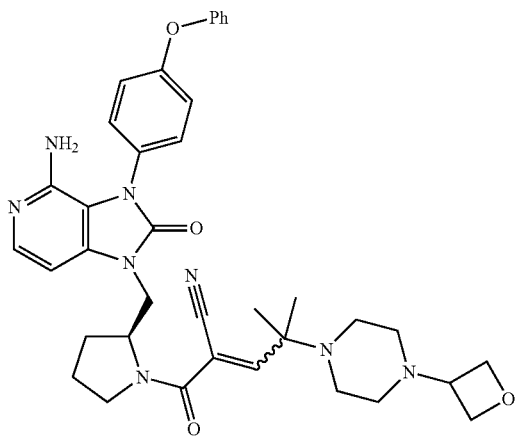 [SMILES: CC(C)(C=C(C#N)C(=O)N1CCC[C@H]1Cn1c(=O)n(-c2ccc(Oc3ccccc3)cc2)c2c(N)nccc21)N1CCN(C2COC2)CC1]

Step 1

To a solution of 2,4-dichloro-3-nitropyridine (5 g, 25.9 mmol) in DMF (50 mL) were added Et$_3$N (5.2 g, 51.8 mmol) and (S)-tert-butyl 2-(aminomethyl)pyrrolidine-1-carboxylate (5.4 g, 27.2 mmol). The resulted mixture was stirred at rt overnight, then filtered and the filtrate was concentrated to dryness. The residue was treated with water (150 mL) and extracted with DCM (30 mL×3). The combined organic phase was washed with brine (40 mL), dried over Na$_2$SO$_4$, and concentrated to dryness. The resulting 6.9 g of (S)-tert-butyl 2-(((2-chloro-3-nitropyridin-4-yl)amino)methyl)pyrrolidine-1-carboxylate was used in next step without further purification.

Step 2

To a solution of (S)-tert-butyl 2-(((2-chloro-3-nitropyridin-4-yl)amino)methyl)pyrrolidine-1-carboxylate (6.9 g, 19.4 mmol) in i-PrOH (100 mL) was added bis(4-methoxybenzyl)amine (7.5 g, 29.1 mmol) and TEA (5.9 g, 58.2 mmol). The mixture was refluxed overnight. After cooling to rt, the mixture was concentrated to dryness. The residue was purified by silica gel chromatography (eluent: petroleum ether/ethyl acetate from 5:1 to 2:1) to give 4.4 g of (S)-tert-butyl 2-(((2-(bis(4-methoxybenzyl)amino)-3-nitropyridin-4-yl)amino)methyl)pyrrolidine-1-carboxylate as a light yellow solid.

Step 3

To a solution of (S)-tert-butyl 2-(((2-(bis(4-methoxybenzyl)amino)-3-nitropyridin-4-yl)amino)methyl)pyrrolidine-1-carboxylate (4.4 g, 7.6 mmol) in EtOH (100 mL) were added NH$_4$Cl (2.0 g, 38.1 mmol) and H$_2$O (10 mL), followed by batch-wise addition of Zn dust (2.5 g, 38.1 mmol) while stirring. The resulted mixture was refluxed for 3 h before filtering through celite. The filtrate was concentrated to afford a residue which was re-dissolved in water (50 mL) and extracted with ethyl acetate (100 mL×3). The combined organic phase was washed with brine (400 mL), dried over Na$_2$SO$_4$, concentrated to give 2.9 g of (S)-tert-butyl 2-(((3-amino-2-(bis(4-methoxybenzyl)amino)pyridin-4-yl)amino)methyl)pyrrolidine-1-carboxylate as a light yellow solid which was used directly in the next step.

Step 4

To a solution of (S)-tert-butyl 2-(((3-amino-2-(bis(4-methoxybenzyl)amino)pyridin-4-yl)amino)methyl)pyrrolidine-1-carboxylate (2.9 g, 5.3 mmol) in anhydrous acetonitrile (30 mL) was added CDI (2.6 g, 15.9 mmol) portion wise. The resulted mixture was refluxed for 2 h before concentration to give a residue which was purified by silica gel chromatography with PE:EtOAc=2:1 to afford 2.6 g of (S)-tert-butyl 2-((4-(bis(4-methoxybenzyl)amino)-2-oxo-2,3-dihydro-1H-imidazo[4,5-c]pyridin-1-yl)methyl)pyrrolidine-1-carboxylate as a light yellow solid which was used directly in the next step.

Step 5

To a solution of (S)-tert-butyl 2-((4-(bis(4-methoxybenzyl)amino)-2-oxo-2,3-dihydro-1H-imidazo[4,5-c]pyridin-1-yl)methyl)pyrrolidine-1-carboxylate (7 g, 12.2 mmol) in anhydrous DCM (100 mL) were added Cu(OAc)$_2$ (2.2 g, 12.4 mmol), TEMPO (2.1 g, 13.4 mmol), 4A molecular sieves (20 g) and Et$_3$N (20 g, 196 mmol), followed by portionwise addition of 4-phenoxyphenylboronic acid (10.5 g, 48.9 mmol) while stirring. The mixture was stirred at rt for 78 h under O$_2$ atmosphere. The solvent was concentrated and the residue was purified by silica gel column with PE:EtOAc=2:1 to yield (S)-tert-butyl 2-((4-(bis(4-methoxybenzyl)amino)-2-oxo-3-(4-phenoxyphenyl)-2,3-dihydro-1H-imidazo[4,5-c]pyridin-1-yl)methyl)pyrrolidine-1-carboxylate (3.2 g, 36%) as a light yellow solid.

Step 5

The (S)-tert-butyl 2-((4-(bis(4-methoxybenzyl)amino)-2-oxo-3-(4-phenoxyphenyl)-2,3-dihydro-1H-imidazo[4,5-c]pyridin-1-yl)methyl)pyrrolidine-1-carboxylate (2 g, 2.7 mmol) was dissolved in TFA (10 mL) and stirred at rt overnight. The reaction was concentrated and the residue was diluted with H2O (50 mL) and extracted with EtOAc. The aqueous phase was adjusted to pH=13 with aqueous NaOH and extracted with EtOAc (2×100 mL), and the organic phase was concentrated to give 870 mg of (S)-4-amino-3-(4-phenoxyphenyl)-1-(pyrrolidin-2-ylmethyl)-1H-imidazo[4,5-c]pyridin-2(3H)-one which was used in next step without further purification.

Step 6

To a solution of (S)-4-amino-3-(4-phenoxyphenyl)-1-(pyrrolidin-2-ylmethyl)-1H-imidazo[4,5-c]pyridin-2(3H)-one (200 mg, 0.5 mmol) in DMF (10 mL) at 0° C. were added Et₃N (150 mg, 1.5 mmol), 2-cyanoacetic acid (47 mg, 0.55 mmol) and HATU (284 mg, 0.75 mmol). After stirring for 30 min at 0° C., the reaction was poured into water (20 mL) and extracted by EtOAc (30 mL for twice), the organic phase was concentrated and the residue was purified by silica gel chromatography eluting with PE:EtOAc=1:1 to afford 70 mg of (S)-3-(2-((4-amino-2-oxo-3-(4-phenoxyphenyl)-2,3-dihydro-1H-imidazo [4,5-c]pyridin-1-yl)methyl)pyrrolidin-1-yl)-3-oxopropanenitrile as a white solid.

Step 7

To a solution of (S)-3-(2-((4-amino-2-oxo-3-(4-phenoxyphenyl-2,3-dihydro H-imidazo[4,5-c]pyridin-1-yl)methyl)pyrrolidin-1-yl)-3-oxopropanenitrile (80 mg, 0.17 mmol), 2-methyl-2-(4-(oxetan-3-yl)piperazin-1-yl)propanal (72 mg, 0.34 mmol) and pyrrolidine (120 mg, 1.7 mmol) in DCM (2 mL) at room temperature was slowly added chloro(trimethyl)silane (69 mg, 0.68 mmol) dropwise. After 30 min, the reaction was diluted with DCM (20 mL) and washed with aq. NaHCO3 (20 mL). The organic layer was dried over anhydrous Na2SO4, filtered and concentrated to give a crude residue, which was purified by Prep-TLC to afford (S)-2-(2-((4-amino-2-oxo-3-(4-phenoxyphenyl)-2,3-dihydro-1H-imidazo[4,5-c]pyridin-1-yl)methyl)pyrrolidine-1-carbonyl)-4-methyl-4-(4-(oxetan-3-yl)piperazin-1-yl) pent-2-enenitrile as white solid (10 mg, 9%). LC-MS m/z: 662.8 (M+1).

Example 12

Synthesis of (S)-1-((1-acryloylpyrrolidin-2-yl)methyl)-4-amino-3-(4-phenoxyphenyl)-1H-imidazo[4,5-c]pyridin-2(3H)-one

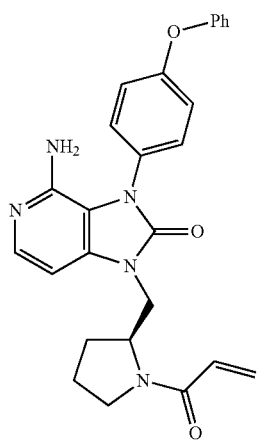 [SMILES: C=CC(=O)N1CCC[C@H]1Cn1c(=O)n(-c2ccc(Oc3ccccc3)cc2)c2c(N)nccc21]

To a solution of (S)-4-amino-3-(4-phenoxyphenyl)-1-(pyrrolidin-2-ylmethyl)-1H-imidazo[4,5-c]pyridin-2(3H)-one (200 mg, 0.17 mmol) and DIPEA (129 mg, 1.0 mmol) in DCM (2 mL) was slowly added acryloyl chloride (45 mg, 0.50 mmol) dropwise at 0° C. After 30 min, the reaction was diluted with DCM (20 mL) and washed with aq. NaHCO₃ (20 mL). The organic layer was dried over anhydrous Na₂SO₄, filtered and concentrated to give a crude residue, which was purified by Prep-TLC to afford 70 mg of (S)-1-((1-acryloylpyrrolidin-2-yl)methyl)-4-amino-3-(4-phenoxyphenyl)-1H-imidazo[4,5-c]pyridin-2(3H)-one as white solid. LC-MS m/z: 455.9 (M+1).

Example 13

Synthesis of (S)-4-amino-1-((1-(but-2-ynoyl)pyrrolidin-2-yl)methyl)-3-(4-phenoxyphenyl)-1H-imidazo[4,5-c]pyridin-2(3H)-one

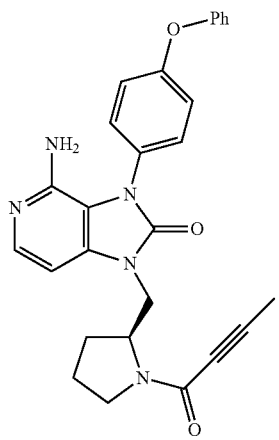 [SMILES: CC#CC(=O)N1CCC[C@H]1Cn1c(=O)n(-c2ccc(Oc3ccccc3)cc2)c2c(N)nccc21]

To a solution of (S)-4-amino-3-(4-phenoxyphenyl)-1-(pyrrolidin-2-ylmethyl)-1H-imidazo[4,5-c]pyridin-2(3H)-one (200 mg, 0.17 mmol) and DIPEA (129 mg, 1.0 mmol) in DCM (10 mL) was slowly added but-2-ynoyl chloride (50 mg, 0.50 mmol) dropwise at 0° C. 0.5 h later, the reaction was diluted with DCM (20 mL) and washed with aq. NaHCO₃ (20 mL). The organic layer was dried over anhydrous Na₂SO₄, filtered and concentrated to give a crude residue, which was purified by Prep-TLC to afford 50 mg of (S)-4-amino-1-((1-(but-2-ynoyl)pyrrolidin-2-yl)methyl)-3-(4-phenoxyphenyl)-1H-imidazo[4,5-c]pyridin-2(3H)-one as white solid. LC-MS m/z: 467.9 (M+1).

Example 14

Synthesis of (R)-4-amino-1-(1-(2-fluoroacryloyl)piperidin-3-yl)-3-(4-phenoxyphenyl)-1H-imidazo[4,5-c]pyridin-2(3H)-one

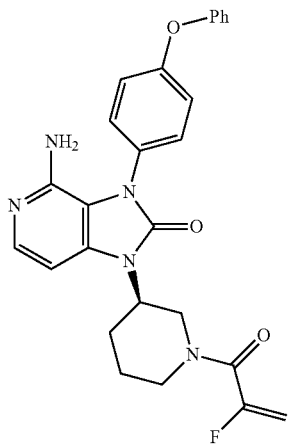 [SMILES: C=C(F)C(=O)N1CCC[C@@H](n2c(=O)n(-c3ccc(Oc4ccccc4)cc3)c3c(N)nccc32)C1]

To a solution of (R)-4-amino-3-(4-phenoxyphenyl)-1-(piperidin-3-yl)-1H-imidazo[4,5-c]pyridin-2(3H)-one (154 mg, 0.38 mmol, 1.0 equiv) in 2 mL of DMF was added diisopropylethylamine (0.2 mL, 1.1 mmol). 2-fluoroprop-2-enoic acid (51.8 mg, 0.580 mmol) was added followed by HATU (97 mg, 1.1 mmol). After stirring 1 h, the material was purified directly by Prep HPLC (Shimadzu, C18 column; mobile phase water with 0.05% TFA and ACN (10% to 90% over 20 min). The purified fractions were diluted with saturated sodium bicarbonate and DCM and the layers separated. The organic layer was dried with $MgSO_4$, filtered and concentrated. It was dissolved in a minimum of water and acetonitrile and lyophilized to obtain 65 mg of (R)-4-amino-1-(1-(2-fluoroacryloyl)piperidin-3-yl)-3-(4-phenoxyphenyl)-1H-imidazo[4,5-c]pyridin-2(3H)-one as a white solid. LC-MS m/z: 474.1 (M+1).

Biological Examples

Example 1

BTX Enzymatic Activity Assay

A Caliper-based kinase assay (Caliper Life Sciences, Hopkinton, Mass.) was used to measure inhibition of BTK kinase activity of a compound of the present disclosure. Serial dilutions of test compounds were incubated with human recombinant BTK (0.5 nM), ATP (16 μM) and a phosphoacceptor peptide substrate FAM-GEEPLYWSF-PAKKK-$NH_2$ (1 μM) at room temperature for 3 h. The reaction was then terminated with EDTA, final concentration 20 mM and the phosphorylated reaction product was quantified on a Caliper Desktop Profiler (Caliper LabChip 3000). Percent inhibition was calculated for each compound dilution and the concentration that produced 50% inhibition was calculated. This value is presented as the $IC_{50}$. The $IC_{50}$ for certain compounds of the disclosure are provided below.

| Compound No. in Compound Table I | $IC_{50}$ (uM) |
|---|---|
| 1 | 0.0082 |
| 2 | 0.0091 |
| 3 | 0.0216 |
| 4 | 0.0078 |
| 5 | 0.0025 |
| 6 | 0.0059 |
| 7 | 0.0018 |
| 8 | 0.0239 |
| 9 | 0.0078 |
| 10 | 0.007 |
| 11 | 0.0786 |
| 12 | 0.0066 |
| 13 | 0.0211 |
| 14 | 0.0172 |
| 15 | 0.0723 |
| 16 | 0.0012 |
| 17 | 0.0133 |
| 18 | 0.0037 |
| 19 | 0.0078 |
| 20 | 0.0145 |
| 21 | 0.0046 |
| 22 | 0.0048 |
| 23 | 0.0259 |
| 24 | 0.0047 |
| 25 | 0.0054 |
| 26 | 0.0035 |
| 27 | 0.0049 |
| 28 | 0.0048 |
| 29 | 0.0018 |
| 30 | 0.0015 |
| 31 | 0.0037 |
| 32 | 0.0029 |
| 34 | 0.0231 |
| 35 | 0.0262 |
| 36 | 0.0157 |
| 37 | 0.0043 |
| 38 | 0.0057 |
| 39 | 0.0053 |
| 40 | 0.0057 |
| 41 | 0.0031 |
| 42 | 0.0041 |
| 43 | 0.0225 |
| 44 | 0.0033 |
| 45 | 0.0251 |
| 46 | 0.0131 |
| 47 | 0.0031 |
| 48 | 0.009 |
| 49 | 0.0128 |
| 50 | 0.0083 |
| 51 | 0.0241 |
| 52 | 0.012 |
| 53 | 0.0042 |
| 54 | 0.0178 |
| 55 | 0.0031 |
| 56 | 0.0078 |
| 57 | 0.0614 |
| 58 | 0.0042 |
| 59 | 0.0026 |
| 60 | 0.0024 |
| 61 | 0.0025 |
| 62 | 0.0059 |
| 63 | 0.0014 |
| 65 | 0.0024 |
| 66 | 0.002 |
| 67 | 0.0012 |

Example 2

Measurement of BTK Occupancy in Human Peripheral Blood Mononuclear Cells

The potency of compounds for inhibition of BTK activity can be assessed by binding of compounds to the target in human peripheral blood mononuclear cells (PBMC) that contain BTK. The extent of BTK occupancy is measured after treating the cells with compounds and detecting unoccupied BTK through binding of occupancy of (R,E)-N-(2-(4-(4-(3-(4-amino-3-(2-fluoro-4-phenoxyphenyl)-1H-pyrazolo[3,4-d]pyrimidin-1-yl)piperidin-1-yl)-4-oxobut-2-en-1-yl)piperazin-1-yl)ethyl)-3-(5,5-difluoro-7,9-dimethyl-5H-4l4,5l4-dipyrrolo[1,2-c:2',1'-f][1,3,2]diazaborinin-2-yl)propanamide as the probe.

Briefly, human blood was obtained from healthy volunteers and distributed 5 ml each in 9 separate 15 ml tubes. Serial dilution of the compound to be tested for potency was added such the final concentrations started at 10 uM and were serially diluted 3-fold for a total of 9 serial dilutions. The compounds were allowed to interact with the blood for 1 h. PBMC were then isolated from each tube using Ficoll. Isolated PBMCs were then resuspended in 1 ml of RPMI1640 media and the occupancy probe was added to a concentration of 1 uM for each sample for 1 h. PBMCs were washed, lysed, and evaluated by SDS-PAGE. In-gel fluorescence was used to measure the extent of inhibition of BTK occupancy probe binding to BTK. Subsequently, total BTK in each sample was determined by Western blotting with a BTK antibody (BD Bioscience Cat#611117).

This assay was also modified to measure the durability of BTK binding in PBMCs. Here, a concentration of 2 uM compound was added to human whole blood for 1 h. PBMCs were isolated using Ficoll, washed, and resuspended in media for either 4 h or 18 h at 37° C. The occupancy probe was added to a concentration of 1 uM for each sample for 1 h, and BTK occupancy was then determined in the same manner as described above.

Example 3

Blockade of CD69 Expression in Human Whole Blood Samples

Activation of the B cell receptor leads to increased BTK activity, calcium mobilization and B cell activation (see Honigberg L. A., el. al., *Proc Natl Acad Sci USA*. 107: 13075-80. 2010). BTK inhibitors have been shown to block B cell activation as measured by CD69 expression (see Karp, R., et. al., Inhibition of BTK with AVL-292 Translates to Protective Activity in Animal Models of Rheumatoid Arthritis. Inflammation Research Association Meeting, September, 2010). CD69 was expressed following B cell activation as a measure of BTK activity in whole blood. Aliquots of whole blood were pre-incubated with serial dilutions of test compound for 30 min followed by activation with anti-IgM (goat Fab'2, 50 μg/ml). Samples were incubated overnight at 37° C. and then stained with PE labeled anti-CD20 and APC labeled anti-CD69 (BD Pharmingen) for 30 min according to the manufacturer's directions. Whole blood was then lysed and cells gated on CD20 expression were quantified for CD 69 expression by FACS. The percent inhibition was calculated based on a DMSO control for no inhibition and plotted as a function of test compound concentration from which an $IC_{50}$ value was calculated.

Example 4

Inhibition of Mouse Collagen-Induced Arthritis

Inhibition of murine collagen-induced arthritis (mCIA) is a standard animal disease model for rheumatoid arthritis. Previous studies have demonstrated that inhibition of BTK is efficacious in blocking mCIA (see Honigberg L. A., et. al., *Proc Natl Acad Sci USA*. 107:13075-80. 2010). Starting on day 0 DBA/1 mice are injected with an emulsion of Type II collagen in Complete Freund's Adjuvant. Mice are boosted 21 days later to synchronize development of disease. After development of mild disease, animals are enrolled in the study and randomized. Dosing is oral, Q.D. typically for 11 days with test compound or dexamethasone (0.2 mg/kg) as control. One group receives vehicle alone. Clinical scoring (0-4) is based on the extent of swelling and severity of arthritis. Scores for all four paws are added for maximum score of 16. Anti-collagen antibodies and total Ig are measured for each animal by Elisa at the end of the study (Bolder BioPath, Boulder, Colo.).

Example 5

Recovery of Kinase Activity Upon Dialysis to Evaluate Irreversible Vs. Reversible Covalent Binding A compound and/or pharmaceutically acceptable salt of the present disclosure at a concentration 10 times greater than its $IC_{50}$ value is added to a solution of protein kinase (5 nM) in a buffer containing 20 mM Hepes [pH 7.5], 5 mM $MgCl_2$, 0.01% Triton X-100, and 1 mM dithiothreitol. After 60 min at 22° C., the reactions are transferred to a dialysis cassette (0.1-0.5 mL Slide-A-Lyzer, MWCO 10 kDa, Pierce) and dialyzed against 1 L of buffer (20 mM Hepes [pH 7.5], 5 mM $MgCl_2$, 0.01% Triton X-100, and 1 mM dithiothreitol.) at 22° C. The dialysis buffer is exchanged twice per day until the end of the experiment. Aliquots are removed from the dialysis cassettes every 24 h and analyzed for protein kinase activity. Kinase activity for each sample is normalized to the DMSO control for that time point and expressed as the mean±SD. It will be observed that the kinase activity will return on dialysis for a compound of the present disclosure where $R^a$ is cyano and will not return for for a compound of the present disclosure where $R^a$ is hydrogen or fluoro.

Example 6

Mass Spectral Analysis

A protein kinase that is inhibited by compound and/or a pharmaceutically acceptable salt of the present disclosure may be subjected to mass spectral analysis to assess the formation of permanent, irreversible covalent adducts. Suitable analytical methods to examine intact full protein or peptide fragments generated upon tryptic cleavage of the protein kinase are generally known in the art (see Lipton, Mary S., Ljiljana, Pasa-Tolic, Eds. Mass Spectrometry of Proteins and Peptides, Methods and Protocols, Second Edition. Humana Press. 2009). Such methods identify permanent, irreversible covalent protein adducts by observing a mass peak that corresponds to the mass of a control sample plus the mass of an irreversible adduct. Two such methods are described below.

Mass Spectral Analysis of Intact Full Kinase Method:

A protein kinase (5 μM) (such as BTK) is incubated with a compound of the present disclosure (25 μM, 5 equiv) for 1 h at room temperature in buffer (20 mM Hepes [pH 8.0], 100 mM NaCl, 10 mM $MgCl_2$). A control sample is also prepared which does not have a compound of the present disclosure. The reaction is stopped by adding an equal volume of 0.4% formic acid, and the samples are analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of the protein kinase and any adducts may be determined with MassLynx deconvolution software (see patent application WO2014 011900, and PCT/US2010/048916).

Results: High-resolution intact mass spectrometry analysis of protein kinase, such as BTK, that is inhibited by a compound of the present disclosure where $R^a$ is cyano will reveal a spectrum similar to the kinase in the absence of inhibitor (e.g. control sample). There will be no formation of a new peak in the mass spectrum corresponding to the molecular mass of the kinase plus the molecular mass of the compound. Conversely, high-resolution intact mass spectrometry analysis of a protein kinase that is inhibited by a a compound of the present disclosure where $R^a$ is hydrogen or fluoro will reveal formation of a new peak (e.g. a peak not present in the control sample without inhibitor) in the mass spectrum corresponding to the molecular mass of the kinase plus the molecular mass of the irreversible kinase inhibitor. On the basis of this experiment, an irreversible protein adduct will be apparent to one skilled in the art.

Mass Spectral Analysis of Kinase Tryptic Digest

Method:

A protein (10-100 pmols) is incubated with a compound and/or a pharmaceutically acceptable salt of the present disclosure (100-1000 pmols, 10 equiv) for 3 h prior to tryptic digestion. Iodoacetamide may be used as the alkylating agent after compound incubation. A control sample is also prepared which does not utilize the compound and/or a pharmaceutically acceptable salt of the present disclosure. For tryptic digests a 1 µl aliquot (3.3 pmols) is diluted with 10 µl of 0.1% TFA prior to micro C18 Zip Tipping directly onto the MALDI target using alpha cyano-4-hydroxy cinnamic acid as the desorption matrix (5 mg/mol in 0.1% TFA:Acetonitrile 50:50) or Sinapinic acid as the desorption matrix (10 mg/mol in 0.1% TFA:Acetonitrile 50:50) (see PCT/US2010/048916).

Results: High-resolution mass spectrometry analysis of the tryptic fragments of a kinase that is inhibited by a compound and/or pharmaceutically acceptable salt of the present disclosure where $R^a$ is cyano, will reveal a spectrum similar to the kinase in the absence of inhibitor (e.g. control sample). There will be no evidence of any modified peptides that are not present in the control sample. On the basis of this experiment, no permanent, irreversible protein adducts will be apparent to one skilled in the art.

On the contrary, High-resolution mass spectrometry analysis of the tryptic fragments of a kinase that is inhibited by compounds of the disclosure where $R^a$ is hydrogen or fluoro, will reveal a spectrum that contains modified peptides that are not present in the control sample. On the basis of this experiment, irreversible protein adducts will be apparent to one skilled in the art. Furthermore, on the basis of the exact mass and MS-MS fragmentation pattern, the sequence of the modified peptide may be ascertained, thereby defining the cysteine residue that is the site of covalent modification.

Example 7

Determination of Drug-Kinase Residence Time

The following is a protocol that can be used to distinguish whether a compound displays a slow or non-existent dissociation rate from BTK, such as typically would occur if a covalent bond is formed between the compound and the target. The read-out for slow dissociation is the ability of the compound of interest to block binding of a high affinity fluorescent tracer molecule to the kinase active site, as detected using time-resolved fluorescence resonance energy transfer (TR-FRET). The experiment was conducted in a buffer consisting of 50 mM Hepes pH 7.5, 10 mM $MgCl_2$, 0.01% Triton X-100, and 1 mM EGTA.

The first step of the procedure was incubation of 500 nM BTK (Invitrogen Cat. #PV3587) with 1.5 µM of a compound of the present disclosure for 30 min in a volume of 10 µL. The mixture was then diluted 5-fold by addition of 40 µL of buffer. A 10 µL volume of the diluted kinase/compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. For BTK, the competition solution contained 1.5 µM Tracer 178 (Invitrogen Cat. #PV5593), which is a proprietary high affinity ligand for BTK coupled to the fluorophore AlexaFluor 647. The competition solution also contained 80 nM of an Anti-polyhistidine antibody coupled to Europium (Invitrogen Cat. #PV5596) which is designed to bind the polyhistidine purification tag in BTK.

After addition of 10 µL of the competition solution to the Greiner plate, the mixture was incubated for one hour or greater to allow time for dissociation of non-covalent inhibitors and binding of the high affinity tracer. It is to be expected that covalent and slow dissociating inhibitors will block binding of the tracer while rapidly dissociating non-covalent inhibitors will not. Binding of the tracer to BTK is detected using TR-FRET between the Europium moiety of the Anti-histidine antibody and the AlexaFluor 647 group of Tracer 178. Binding was evaluated using a Perkin Elmer Envision instrument (Model 2101) equipped with filters and mirrors compatible with LANCE-type TR-FRET experiments. Data were plotted at percentage of signal obtained in the absence of competitor compound. The background signal was obtained by omission of BTK from the reaction. If the compound is an irreversible covalent inhibitor, tracer will be completely blocked from binding to the target throughout the entire course of the experiment. If the compound is a reversible covalent inhibitor, the tracer will bind the target as the compound dissociates from the target. For the durability measurements, the range of occupancy for the compounds disclosed herein at 1, 6, and 24 h of washout is shown below.

| Compound in compound Table I above | % occupany at 1, 6, & 24 h |
|---|---|
| 1 | 97.036 |
|   | 82.199 |
|   | 70.975 |
| 2 | 93.602 |
|   | 85.49 |
|   | 65.826 |
| 3 | 65.626 |
|   | 58.519 |
|   | 46.073 |
| 4 | 90.005 |
|   | 66.344 |
|   | 18.2 |

-continued

| Compound in compound Table I above | % occupany at 1, 6, & 24 h |
|---|---|
| 5 | 93.773 |
|  | 83.103 |
|  | 57.488 |
| 6 | 94.404 |
|  | 86.64 |
|  | 67.505 |
| 7 | 61.932 |
|  | −1.3946 |
|  | −12.344 |
| 8 | 93.335 |
|  | 89.195 |
|  | 80.873 |
| 9 | 93.363 |
|  | 70.733 |
|  | 31.4 |
| 10 | 94.392 |
|  | 77.985 |
|  | 49.145 |
| 12 | 95.906 |
|  | 96.44 |
|  | 90.847 |
| 13 | 91.54 |
|  | 83.963 |
|  | 49.152 |
| 14 | 91.481 |
|  | 76.396 |
|  | 22.922 |
| 15 | 91.927 |
|  | 85.356 |
|  | 50.188 |
| 16 | 96.326 |
|  | 97.673 |
|  | 102.07 |
| 17 | 81.247 |
|  | 78.623 |
|  | 74.744 |
| 18 | 93.065 |
|  | 73.513 |
|  | 31.704 |

Example 8

Reversibility of Binding

The following approach was developed to determine if a compound forms irreversible covalent or reversible covalent bond with its targets. Reactions are prepared with the protein target at a higher concentration than the compounds of interest. Both irreversible and reversible covalent compounds bind the target and became depleted from solution. The reactions are then treated with perturbations including both denaturation with 5 M guanidine hydrochloride and digestion with trypsin, disrupting proper folding of the target. It will be found that the perturbation returns reversible covalent compounds to solution due to dissociation from the target while irreversible covalent compounds remain bound to the target. The concentration of compound in solution is assessed both preceding and following perturbation using high performance liquid chromatography (HPLC) coupled to tandem mass spectrometry. Using this technique, it can be demonstrated that irreversible covalent compound of the disclosure where $R^a$ is hydrogen or fluoro is depleted from solution in both the native and perturbed state, while compounds disclosed herein where $R^a$ is cyano are depleted in the folded state but returned to solution following perturbation of the target evidencing that such compounds form reversible covalent bond.

Formulation Examples

The following are representative pharmaceutical formulations containing a compound of Formula (I).

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL The foregoing disclosure has been described in some detail by way of illustration and example, for purposes of clarity and understanding. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

What is claimed is:
1. The compound
(R)-1-(1-acryloylpiperidin-3-yl)-4-amino-3-(4-phenoxyphenyl)-1H-imidazo[4,5-c]pyridin-2(3H)-one
and/or
a pharmaceutically acceptable salt thereof.
2. A pharmaceutical composition comprising the compound and/or a pharmaceutically acceptable salt thereof of claim 1 and a pharmaceutically acceptable excipient.
3. A method of inhibiting BTK in a mammal in need thereof, wherein the method comprises administering to the mammal in need of such treatment a pharmaceutical composition comprising a therapeutically effective amount of the compound and/or a pharmaceutically acceptable salt thereof of claim 1 and a pharmaceutically acceptable excipient.

* * * * *